(12) United States Patent
Smith et al.

(10) Patent No.: US 11,324,734 B2
(45) Date of Patent: May 10, 2022

(54) COMPOSITIONS AND METHODS FOR TREATING ANEMIA

(71) Applicant: Akebia Therapeutics, Inc., Cambridge, MA (US)

(72) Inventors: Alexander Smith, Apex, NC (US); Gurudatt Ajay Chandorkar, Waltham, MA (US); Ene Ikpong Ette, Framingham, MA (US); Bradley John Maroni, Boston, MA (US); Charlotte Suzanne Hartman, Carmel, IN (US); Ramin Farzaneh-Far, Brookline, MA (US); Jula Kern Inrig, Yorba Linda, CA (US)

(73) Assignee: Akebia Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/563,169

(22) PCT Filed: Mar. 31, 2016

(86) PCT No.: PCT/US2016/025235
§ 371 (c)(1),
(2) Date: Sep. 29, 2017

(87) PCT Pub. No.: WO2016/161094
PCT Pub. Date: Oct. 6, 2016

(65) Prior Publication Data
US 2018/0092892 A1 Apr. 5, 2018

Related U.S. Application Data

(60) Provisional application No. 62/270,168, filed on Dec. 21, 2015, provisional application No. 62/141,420, filed on Apr. 1, 2015.

(51) Int. Cl.
| | |
|---|---|
| *A61K 31/4418* | (2006.01) |
| *A61K 9/20* | (2006.01) |
| *A61K 9/28* | (2006.01) |
| *A61K 31/16* | (2006.01) |
| *C07D 213/81* | (2006.01) |

(52) U.S. Cl.
CPC ........ *A61K 31/4418* (2013.01); *A61K 9/2009* (2013.01); *A61K 9/2013* (2013.01); *A61K 9/2054* (2013.01); *A61K 9/2059* (2013.01); *A61K 9/2866* (2013.01); *A61K 31/16* (2013.01); *C07D 213/81* (2013.01)

(58) Field of Classification Search
CPC combination set(s) only.
See application file for complete search history.

(56) References Cited

U.S. PATENT DOCUMENTS

| | | | |
|---|---|---|---|
| 3,655,679 | A | 4/1972 | Tsung-Ing et al. |
| 3,703,582 | A | 11/1972 | Shen et al. |
| 3,894,920 | A | 7/1975 | Kondo et al. |
| 4,016,287 | A | 4/1977 | Eberhardt et al. |
| 5,397,799 | A | 4/1995 | Weidmann et al. |
| 5,405,613 | A | 4/1995 | Rowland |
| 5,607,954 | A | 3/1997 | Weidmann et al. |
| 5,610,172 | A | 4/1997 | Weidmann et al. |
| 5,620,995 | A | 4/1997 | Weidmann et al. |
| 5,620,996 | A | 8/1997 | Weidmann et al. |
| 5,658,933 | A | 8/1997 | Weidmann et al. |
| 5,719,164 | A | 3/1998 | Weidmann et al. |
| 5,726,305 | A | 3/1998 | Weidmann et al. |
| 6,020,350 | A | 7/2000 | Weidmann et al. |
| 6,093,730 | A | 7/2000 | Weidmann et al. |
| 6,159,379 | A | 12/2000 | Means et al. |
| 6,420,427 | B1 | 7/2002 | Takahashi et al. |
| 6,566,088 | B1 | 7/2003 | Zhu et al. |
| 6,589,758 | B1 | 7/2003 | Zhu et al. |
| 7,183,287 | B2 | 2/2007 | Durley |
| 7,323,475 | B2 | 1/2008 | Arend et al. |
| 7,588,924 | B2 | 9/2009 | Evdokimov et al. |
| 7,811,595 | B2 | 10/2010 | Kawamoto et al. |
| 8,050,873 | B2 | 11/2011 | Evdokimov et al. |
| 8,124,582 | B2 | 2/2012 | Guenzler-Pukall et al. |
| 8,273,773 | B2 | 9/2012 | Brameld et al. |
| 8,323,671 | B2 | 12/2012 | Wu et al. |
| 8,343,952 | B2 | 1/2013 | Kawamoto et al. |
| 8,512,972 | B2 | 8/2013 | Evdokimov et al. |
| 8,530,404 | B2 | 9/2013 | Seeley et al. |
| 8,598,210 | B2 | 12/2013 | Kawamoto et al. |
| 8,722,895 | B2 | 5/2014 | Kawamoto et al. |
| 8,865,748 | B2 | 12/2014 | Shalwitz et al. |

(Continued)

FOREIGN PATENT DOCUMENTS

| | | |
|---|---|---|
| AU | 2007265460 B2 | 1/2008 |
| CA | 2098158 | 6/1993 |

(Continued)

OTHER PUBLICATIONS

U.S. Appl. No. 15/875,495, filed Jan. 19, 2018, Kawamoto et al.
U.S. Appl. No. 15/994,348, filed May 31, 2018, Copp et al.
U.S. Appl. No. 16/119,146, filed Aug. 31, 18, Kawamoto et al.
"Akebia closes $41 million series C—Proceeds to support phase 2b trial and phase 3 prepartions for promising anemia candidate", 2013, retrieved from the internet: <http://files.shareholder.com/downloads/AMDA-2MD7AT/0x0x733748/5e5822e6-2bcd-4969-ab79-0d298fee5066/733748.pdf.

(Continued)

*Primary Examiner* — Kathrien A Cruz
(74) *Attorney, Agent, or Firm* — Proskauer Rose LLP; Fangli Chen

(57) ABSTRACT

Provided herein are specific doses of, and dosing regimens for, using a HIF prolyl hydroxylase inhibitor in treating or preventing anemia, such as anemia secondary to or associated with chronic kidney disease, anemia secondary to or associated with non-dialysis dependent chronic kidney disease anemia associated with or resulting from chemotherapy, or anemia associated with AIDS.

8 Claims, 4 Drawing Sheets

(56) References Cited

U.S. PATENT DOCUMENTS

Figure 1A:
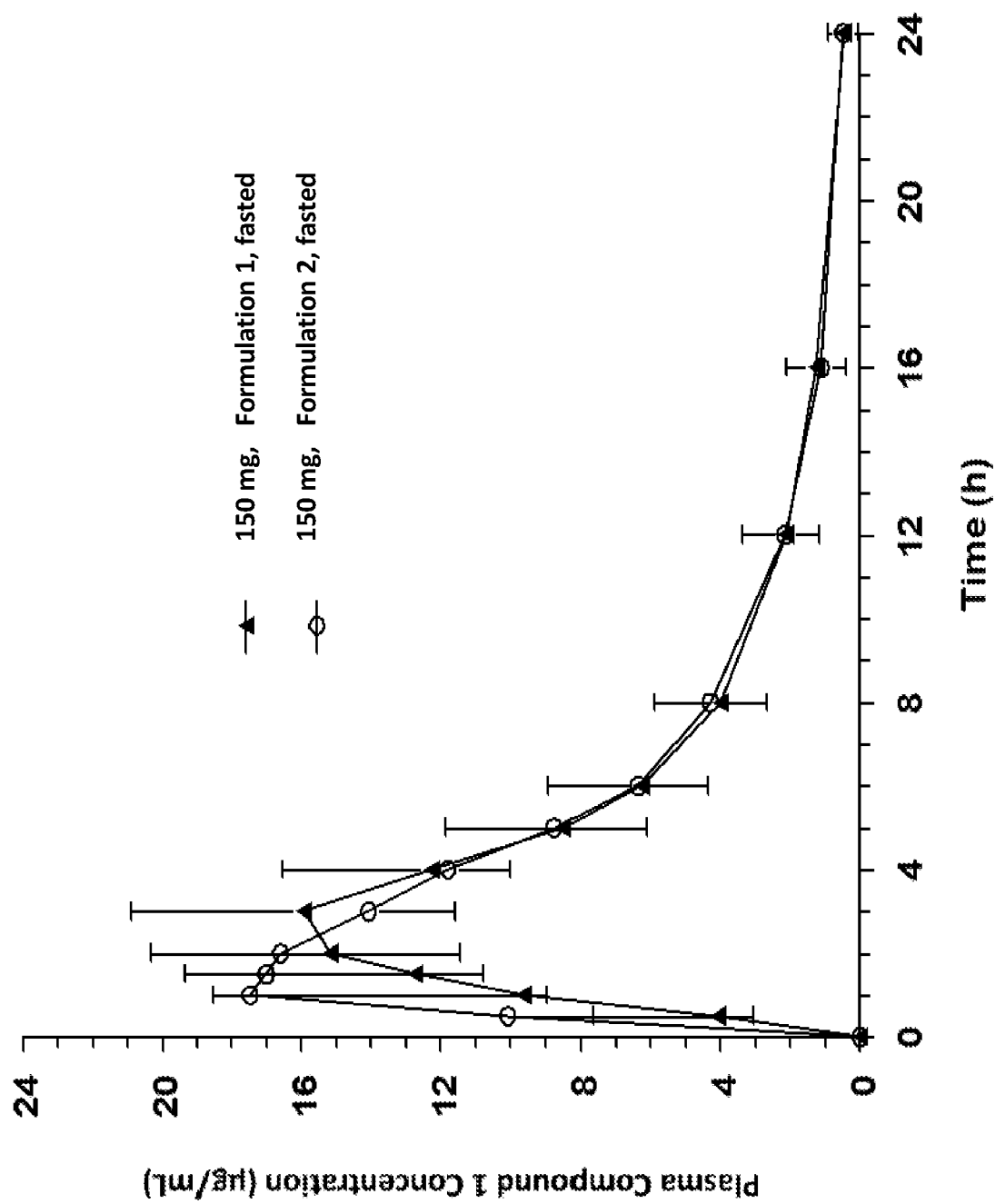

| | | | |
|---|---|---|---|
| 8,940,773 B2 | 1/2015 | Kawamoto et al. |
| 9,145,366 B2 | 9/2015 | Lanthier et al. |
| 9,598,370 B2 | 3/2017 | Kawamoto et al. |
| 9,701,636 B2 | 7/2017 | Copp et al. |
| 9,776,969 B2 | 10/2017 | Lanthier et al. |
| 9,987,262 B2 | 6/2018 | Copp et al. |
| 2002/0192737 A1 | 12/2002 | Kaelin, Jr. et al. |
| 2003/0153503 A1 | 8/2003 | Klaus et al. |
| 2003/0176317 A1 | 9/2003 | Guenzler-Pukall |
| 2004/0235082 A1 | 11/2004 | Fourncy et al. |
| 2004/0254215 A1 | 12/2004 | Arend et al. |
| 2006/0142389 A1 | 6/2006 | Aurell et al. |
| 2006/0276477 A1 | 12/2006 | Klaus et al. |
| 2007/0105899 A1 | 5/2007 | Suzuki et al. |
| 2007/0154482 A1 | 7/2007 | Sukhatme et al. |
| 2007/0203174 A1 | 8/2007 | Klimko et al. |
| 2007/0213335 A1 | 9/2007 | Fitch et al. |
| 2007/0299086 A1 | 12/2007 | Kawamoto et al. |
| 2008/0124740 A1 | 5/2008 | Evdokimov et al. |
| 2008/0213404 A1 | 9/2008 | Johnson et al. |
| 2009/0023666 A1 | 1/2009 | Gardiner et al. |
| 2009/0082357 A1 | 3/2009 | Fitch et al. |
| 2010/0021423 A1 | 1/2010 | Brameld et al. |
| 2011/0305776 A1 | 12/2011 | Ho et al. |
| 2012/0282627 A1 | 11/2012 | Evdokimov et al. |
| 2012/0309977 A1 | 12/2012 | Lanthier et al. |
| 2012/0316204 A1 | 12/2012 | Shalwitz et al. |
| 2012/0329836 A1 | 12/2012 | Marsh et al. |
| 2013/0022974 A1 | 1/2013 | Chinnaiyan et al. |
| 2014/0045899 A1 | 2/2014 | Kawamoto et al. |
| 2014/0057892 A1 | 2/2014 | Kawamoto et al. |
| 2014/0171465 A1 | 6/2014 | Yu |
| 2015/0119425 A1 | 4/2015 | Kawamoto et al. |
| 2015/0141467 A1 | 5/2015 | Copp et al. |
| 2015/0361043 A1 | 12/2015 | Lanthier et al. |
| 2016/0009648 A1 | 1/2016 | Kawamoto et al. |
| 2016/0143891 A1 | 5/2016 | Shalwitz et al. |
| 2016/0199434 A1 | 7/2016 | Eubank et al. |
| 2016/0214939 A1 | 7/2016 | Hanselmann et al. |
| 2016/0339005 A1 | 11/2016 | Shalwitz et al. |
| 2017/0362178 A1 | 12/2017 | Lanthier et al. |
| 2018/0065933 A1 | 3/2018 | Hanselmann et al. |

FOREIGN PATENT DOCUMENTS

| | | |
|---|---|---|
| CA | 2253282 | 11/1997 |
| CA | 2659682 A1 | 1/2008 |
| CN | 103429239 A | 12/2013 |
| EP | 0650960 | 5/1995 |
| EP | 0650961 | 5/1995 |
| EP | 2044005 | 10/2010 |
| JP | H09221476 | 8/1997 |
| JP | 2001-48786 | 2/2001 |
| JP | 2003527424 A | 9/2003 |
| JP | 2007-194072 | 8/2007 |
| JP | 2010-527378 | 11/2009 |
| WO | WO 1996/022021 | 7/1996 |
| WO | WO 1997/041103 | 11/1997 |
| WO | WO 1997/044333 | 11/1997 |
| WO | WO 1999/048870 | 11/1999 |
| WO | WO 2001/070225 A2 | 9/2001 |
| WO | WO 2002/074980 | 9/2002 |
| WO | WO 2002/074981 | 9/2002 |
| WO | WO 2002/083688 | 10/2002 |
| WO | WO 2003/028663 | 4/2003 |
| WO | WO 2003/032972 | 4/2003 |
| WO | WO 2003/049686 | 6/2003 |
| WO | WO 2003/053997 | 7/2003 |
| WO | WO 2003/097040 | 11/2003 |
| WO | WO 2004/019868 | 3/2004 |
| WO | WO 2004/035812 | 4/2004 |
| WO | WO 2004/048383 | 6/2004 |
| WO | WO 2004/108121 | 12/2004 |
| WO | WO 2005/007192 | 1/2005 |
| WO | WO 2005/115984 | 12/2005 |
| WO | WO 2005/118836 | 12/2005 |
| WO | WO 2006/019831 | 2/2006 |
| WO | WO 2006/030977 | 3/2006 |
| WO | WO 2006/114213 | 11/2006 |
| WO | WO 2007/047194 | 4/2007 |
| WO | WO 2007/070359 | 6/2007 |
| WO | WO 2007/082899 | 7/2007 |
| WO | WO 2007/084667 | 7/2007 |
| WO | WO 2007/088571 | 8/2007 |
| WO | WO 2007/103905 | 9/2007 |
| WO | WO 2007/128495 A2 | 11/2007 |
| WO | WO 2007/136990 | 11/2007 |
| WO | WO 2007/150011 | 12/2007 |
| WO | WO 2008/002576 | 1/2008 |
| WO | WO 2008/089051 | 7/2008 |
| WO | WO 2008/089052 | 7/2008 |
| WO | WO 2009/020119 | 8/2008 |
| WO | WO 2008/130508 | 10/2008 |
| WO | WO 2008/130527 | 10/2008 |
| WO | WO 2008/137060 | 11/2008 |
| WO | WO 2008/141731 | 11/2008 |
| WO | WO 2008/144266 | 11/2008 |
| WO | WO 2009/019656 | 2/2009 |
| WO | WO 2009/035534 | 3/2009 |
| WO | WO 2009/037570 | 3/2009 |
| WO | WO 2009/039321 | 3/2009 |
| WO | WO 2009/039323 | 3/2009 |
| WO | WO 2007/038571 | 4/2009 |
| WO | WO 2009/043093 | 4/2009 |
| WO | WO 2009/049112 | 4/2009 |
| WO | WO 2009/067790 | 4/2009 |
| WO | WO 2009/070644 | 6/2009 |
| WO | WO 2009/073497 | 6/2009 |
| WO | WO 2009/073669 | 6/2009 |
| WO | WO 2009/086044 | 7/2009 |
| WO | WO 2009/086592 | 7/2009 |
| WO | WO 2009/089547 | 7/2009 |
| WO | WO 2009/111337 | 9/2009 |
| WO | WO 2010/029577 | 3/2010 |
| WO | WO 2010/113942 | 10/2010 |
| WO | WO 2011/057112 | 11/2010 |
| WO | WO 2012/170377 | 12/2012 |
| WO | WO 2012/170439 | 12/2012 |
| WO | WO 2012/170442 | 12/2012 |
| WO | WO 2013/013609 | 1/2013 |
| WO | WO 2013/070908 A1 | 5/2013 |
| WO | WO 2014075692 A1 | 5/2014 |
| WO | WO 2014/168986 | 10/2014 |
| WO | 2014197660 A1 | 12/2014 |
| WO | WO 2014/200773 | 12/2014 |
| WO | WO 2015/023967 | 2/2015 |
| WO | WO 2015/073779 | 5/2015 |
| WO | WO 2015/112831 | 7/2015 |
| WO | WO 2016/118858 | 7/2016 |
| WO | WO 2016/153996 | 9/2016 |
| WO | WO 2016/161094 | 10/2016 |
| WO | WO 2016160668 A1 | 10/2016 |
| WO | WO 2006/13 8511 | 12/2016 |

OTHER PUBLICATIONS

"Hippuric acid sodium salt", Science Lab.com: Chemicals & Laboratory Equipment (*http://web.archive.org/web/20041107121553/http://www.sciencelab.com/page/S/PVAR/10415/SLH2620 accessed Mar. 11, 2010).

"Standards of Medical Care in Diabetes—2006," Diabetes Care, 29:s4-s42 (2006).

Acker et al., 2005, "Genetic evidence for a tumor suppressor role of HIF-2α", Cancer Cell, 8:131-141.

Alesso et al., "Improving resins for solid phase synthesis: incorporation of 1-[2-(2-methoxyethoxy)ethoxy]4-vinyl-benzene" Tetrahedron: 59,7163-7169 (2003).

Altschul et al., "Gapped BLAST and PSI-BLAST: A New Generation of Protein Database Search Programs," Nucleic Acids Res., 25(27):3389-3402 (1997).

Anderson et al., "Antileukemic Activity of Derivatives of 1,2-Dimethyl-3,4-bis(hydroxymethyl)-5-phenylpyrrole Bis(N-methylcarbamate)" J. Med. Chem.: vol. 22(8). 977-980 (1979).

(56) References Cited

OTHER PUBLICATIONS

Anderson, 2012, "Practical process research and development: a guide for organic chemists", p. 331.
Annex et al., "Growth Factor-Induced Therapeutic Angiogenesis in the Heart: Protein Therapy," Cardiovascular Research, 65(3):649-655 (2005).
Ardelt et al. "Estradiol Regulates Angiopoietin-1 mRNA Expression Through Estrogen Receptor-α in a Rodent Experimental Stroke Model," Stroke, 36: 337-341 (2005).
Auerbach et al., "Angiogenesis Assays: A Critical Overview." Clinical Chemistry. 49:32-40 (2003).
Barany et al., "Solid-phase Peptide Synthesis: A Silver Anniversary Report" Int. J. Peptide Protein Res., 30(6):705-739 (1987).
Bartlett et al., "Molecular Recognition in Chemical and Biological Problems," Special Pub., Royal Chem. Soc., 78, 182-196 Caveat: A Program to Facilitate the Structure-derived Design of Biologically Active Molecules (Apr. 1989).
Bohm, "The Computer Program LUDI: A New Method for the Novo Design of Enzyme Inhibitors," J. Computer-Aided Molecular Design, 6:61-78 (1992).
Branden et al., "Introduction to Protein Structure Second Edition," Garland Publishing. Inc., New York, 1999, pp. 374-375.
Brittain et al., 2009, "Polymorphism in Pharmaceutical Solids." Drugs and the Pharmaceutical Sciences, 2nd Edition, Edited by Brittain H.G., 192: 333-335.
Burger, 1991, Isosterism and biososterism in drug design, Progress in Drug Research, Birkhauser Verlag.
Bussolino, "Molecular Mechanisms of Blood Vessel Formation" Trends Biochem. Sci., 22(7):251-256 (1997).
Byrn et al., 1995, "Pharmaceutical Solids: A Strategic Approach to Regularity Considerations", Pharmaceutical Research, 12(7): 945-954.
CAS Registry Nos. 1261813-98-2, 1261613-86-8, and 1261518-21-1. Chemcats, 2011.
Carey, FA., 2006, Organic Chemistry $6^{th}$ Ed. Mcgraw Hill. Chapter 1, p. 9, chapter 19, pp. 839-840 and chapter 27, pp. 1182-1183.
Catrina et al., 2004, "Hyperglycemia Regulates Hypoxia-Inducible Factor-la Protein Stability and Function," Diabetes 53:3226-3232.
Cheeseright, 2009, "The Identification of Bioisosteres as Drug Development Candidates", Innovations in Pharmaceutical Technology, issue 28.
Cherng, 2002, "Synthesis of substituted pryidines by the reactions of halopyridines with sulfur, oxygen and carbon nucleophiles under focused microwave irradition". Tetrahedron, Jun. 10, 2002, 58(24): 4931-4935.
Clinicaltrials.gov: archive: NCT01235936 Nn 2012_09_30[online], U.S. National Institute of Health, Aug. 30, 2012; retrieved from the internet <http:clinicaltrials.gov/archive/NCT01235936/2012_09_30>.
Cousins, "Retina Today", Oct. 2009, 2 pages; retrieved from the internet at http://reinatoday.com/2009/10/1009_12.php.
Costello et al., 2012, "Evidence for changes in RREB-1, ZIP3, and zinc in the early developmentof pancreatic adenocarcinoma", J Gastrointest Canc, 43: 570-578.
Cunliffe et al., "Novel Inhibitors of Prolyl 4-Hydroxylase. 3. Inhibition by the Substrate Analogue N-Oxaloglycine and Its Derivatives." J. Med. Chem. 35:2652-2658 (1992).
Demetriades et al., 2012, "Dynamic combinatinatorial chemistry employing embryonic boronic acids/boronate esters leads to potent oxygenase inhibitors", Angewandte Chemie, International Edition, May 25, 2012, 51(27): 6672-6675.
Designation of Inventors filed on entry into EP Regional Phase of EP Pat. No. 2044005.
Dranoff, 2003, "GM-CSF-secreting melanoma vaccines", Oncogene, 22: 3188-3192.
Elson et al., "Induction of Hypervascularity Without Leakage or Inflammation in Transgenic Mice Overexpressing Hypoxia-Indicible Factor-1α," Genes & Dev., 15:2520-2532 (2001).

El Vidge et al., 2006, "Concordant Regulation of Gene Expression by Hypoxia and 2-Oxoglutarate-dependent Dioxygenase Inhibition", J. Biol. Chem., 281(22): 15215-15226.
Enoch et al., 2006, "ABC of wound healing. Non-surgical and drug treatments", BMJ, 332(7546):332:900-3.
European Patent Office, Interlocutory Decision in Opposition Proceedings for European patent No. 2044005, mailed May 3, 2013, 76 pages.
European Patent Office, Minutes of the Oral Proceedings Before the Opposition Division for European patent No. 2044005, mailed May 3, 2013, 6 pages.
Extract from USPTO patent assignment database regarding U.S. Appl. No. 11/821,936.
Favier et al., 2007, "HIF2α reduces growth rate but promotes angiogenesis in a mouse model of neuroblastoma", BMC Cancer, 7:139: 1-10.
Flower, "Modelling G-protein-coupled receptors for drug design," Biochimica et Biophysica Acta, 1422:207-234 (1999).
Folkman et al., "Tumor Angiogenesis," The Molecular Basis of Cancer, Mendelsohn et al., eds., W.B. Saunders. Chapter 10, pp. 206-232 (1995).
Franklin et al., "Approaches to the Design of Anti-Fibrotic Drugs," Biochem. Soc. Trans., 19(4):812-5 (Nov. 1991).
Gaunt, 1998, "Rational Design of Benzyl-Type Protecting Groups Allows Sequential Deprotection of Hydroxyl Groups by Catalytic Hydrogenolysis", 63(13): 4172-4173.
Gavhane et al., 2011, "Solid tumors: Facts, challenges, and solutions", International Journal of Pharma Sciences and Research, 2(1): 1-12.
Goodford, "A Computational Procedure for Determining Energetically Favorable Binding Sites on Biologically Important Macromolecules," J. Med. Chem., 28(7):849-857 (1985).
Goodsell et al., "Automated Docking of Substrates to Proteins by Simulated Annealing," Proteins: Structure, Function, and Genetics, 8: 195-202 (1990).
Greer et. al., 2012 "The updated biology of hypoxia inducible factor", EMBO J. 31: 2448-2460.
Guillory, 1999, "Generation of polymorphs, hydrates, solvates, and amorphous solids", HG Brittain (Ed.), Polymorphism in Pharmaceutical Solids, V. 95, Marcel Dekker, New York: 183-226.
Hardcastle et al., 2005, "Discovery of Potent Chromen-4-one Inhibitors of the DNA-Dependent Protein Kinase (DNA-PK) Using a Small-Molecule Library Approach", J. of Medicinal Chem., 48(24): 7829-7846.
Hoesksema et al., 1982, "Structure of Rubradirin", J. of American Chem. Society, 104(19): 5173-5181.
Hu et al., 2003, "Differential Roles of Hypoxia-Inducible Factor 1α(HIF-1α) and HIF-2α in Hypoxic Gene Regulation", Mol. Cell. Biol., 23: 9361-9374.
Ingersoll et al. "Hippuric Acid", Organic Syntheses, CV 2, 328; retrieved from the internet at <http:web.archive.org/web20020724135719/http://orgsyn.org/orgsy n/prepContent.asp?prep=cv2p0328> on Mar. 11, 2010.
International Preliminary Report on Patentability dated Dec. 10, 2013 for PCT/2012/40833.
International Search Report dated May 8, 2008 for PCT/US2007/014832.
International Search Report and Written Opinion dated Aug. 29, 2012 for PCT/2012/40833.
International Search Report and Written Opinion date Apr. 20, 2015 for PCT/US2015/12634.
International Union of Pure and Applied Chemistry; Glossary of Class Names of Organic Compounds and Reactive Intermediates Based on Structure: Pure & D Appl. Chern., vol. 67, Nos. 8/9, pp. 1307-1375, (1995).
Ivan el al., "Biochemical purification and pharmacological inhibition of a mammalian prolyl hydroxylase acting on hypoxia-inducible factor," Proceedings of the National Academy of Science; 99(21) 13459-13464 (2002).
Ivan et al., "HIFa Targeted for VHL-Mediated Destruction by Praline Hydroxylation: Implications for 02 Sensing." Science 292, 464-468 (2001).

(56) References Cited

OTHER PUBLICATIONS

Ivanisevic et al., 2011, "Uses of X-Ray Powder Diffraction in the Pharmaceutical Industry." Pharmaceutical Formulation & Quality. Aug./Sep. 2011, pp. 30-33.
Iyoda et al., 1990, "Homocoupling of aryl halides using nickel(II) complex and zinc in the presence of Et4NI. An efficient method for the synthesis of biaryls and bipyridines", Bull. Chem. Soc. Jpn, 63(1): 80-87.
Jaakkola el al., "Targeting of HIF-α to the von Hippel-Lindau Ubiquitylation Complex by $O_2$-Regulated Prolyl Hydroxylation," Science 292, 468-472 (2001).
Jones el al., "Molecular Recognition of Receptor Sites Using a Genetic Algorithm with a Description of Desolvation," J. Mol. Biol., 245:43-53 (1995).
Kaelin, "Proline Hydroxylation and Gene Expression," Annu. Rev. Biochem., 74:115-125 (2005).
Karuppagounder et. al., 2012 "Hypoxia-inducible factor prolyl hydroxylase inhibition: robust new target or another big bust for stroke therapeutics?", J. Cereb. Blood F. Met., 32: 1347-1361.
Kawashima el al., Suppressive effect of quinolinic acid and hippuric acid on bone marrow erythroid growth and lymphocyte blast formation in uremia, Advances in Experimental Medicine and Biology, (1987), vol. 223, p. 69-72.
Ke and Costa, 2006, "Hypoxia-Inducible Factor-1 (HIF-1)", Molecular Pharmacology, 70(5): 1469-1480.
Khandhadia et al., 2012, "Neurodegenerative Diseases", edited by Shamim I. Ahmed, Published by Landes Biosciences and Springer Science + Business Media, Chapter 2: 15-36.
Kietzmann et al., 2001, "Perivenous expression of the mRNA of the three hypoxia-inducible factor α-subunits, HIF1α, HIF2α and HIF3α, in rat liver", Biochem. J., 354: 531-537.
Kim et al., 2015, "Recent advances in developing inhibitors for hypoxia-inducible factor prolyl hydroxylases and their therapeutic implications", Molecules, 20: 20551-20568.
Krantz, "Erythropoietin," Blood, 77:419-434 (1991).
Kuntz et al., A Geometric Approach to Macromolecule-Ligand Interactions, J. Mol. Biol., 161:269-288 (1982).
Kurti et al., 2005, "Strategic applications of named reactions in organic synthesis", El Sevior: 448-449 and p. 484-485.
Langsetmo, 2006, "Inhibition of HIF-Prolyl Hydroxylases with FG-4539 is Neuroprotective in a Mouse Model of Permanent Focal Ischemia," International Stroke Conference, Kissimmee Florida, Presentation No. 427.
Lee et al., "Structure of Human FIH-1 Reveals a Unique Active Site Pocket and Interaction Sites for HIF-1 and von Hippel Lindau," JBC, 278:7558-7563 (2003).
Li et al., "PR39, A Peptide Regulator of Angiogenesis," Nat Med., 6(1):49-55 (2000).
Lima and Barreiro, 2005, "Bioisosterism: A Useful Strategy for Molecular Modification and Drug Design", Current Medicinal Chemistry, 12:23-49.
Liu et al., Jun. 2011, "Hypoxia Induces Genomic DNA Demethylation through the Activation of HIF-1alpha and Transcriptional Upregulation of MAT2A in Hepatoma Cells", Mol. Cancer Ther., 10: 1113-1123.
Mancini et al., "Effect of Erythropoietin on Exercise Capacity in Patients with Moderate to Severe Chronic Heart Failure," Circulation, 107:294-299 (2003).
McDonough et al., "Cellular Oxygen Sensing: Crystal Structure of Hypoxia-Inducible Factor Prolyl Hydroxylase (PHD2)," PNAS, 103(26):9814-9819 (2006).
Miranker et al., "Functionality Maps of Binding Sites: A Multiple Copy Simultaneous Search Method," Proteins: Structure, Function and Genetics, 11:29-34 (1991).
Morissette et al., 2004, "High-throughput crystallization: polymorphs, salts, co-crystals and solvates of pharmaceutical solids", Advanced Drug Delivery Reviews, 56: 275-300.
Myerson, 2002, Handbook of Industrial Crystallization, p. 249.
Nielsen et. al., 2010, "Antiangiogenic therapy for Breast Cancer", Breast Cancer Res. 12:209-227.

Nguyen et al., "Cellular Interactions in Vascular Growth and Differentiation" Int. Review of Cytology. 204:1-48 (2001).
Nishibata et al., "Automatic Creation of Drug Candidate Structures Based on Receptor Structure. Starting Point for Artificial Lead Generation," Tetrahedron. 47( 43):8985-8990 (1991).
Nowak et al., 2006, "Age-related macular degeneration (AMD): pathogenesis and therapy", Pharmacological Reports, 58: 353-363.
O'Reilly et al., "Angiostatin: A Novel Angiogenesis Inhibitor that Mediates the Suppression of Metastases by a Lewis Lung Carcinoma," Cell, 79:315-328 (1994).
O'Reilly et al., "Endostatin: An Endogenous Inhibitor of Angiogenesis and Tumor Growth," Cell, 88:277-285 (1997).
Online Abstract showing publication date of McDonough et al. (2006) as Jun. 16, 2006.
Pasqualetti et al., 2000, "Circadian rhythm of serum erythropoietin in myelodysplastic syndromes", European Review for Medical and Pharmacological Sciences, 4: 111-115.
PCT Request Form dated Jun. 26, 2007 for PCT/US2007/014832.
Pergola et al., 2016, "Vadadustat, a novel oral HIF stabilizer, provides effective anemia treatement in nondialysis-dependent chronic kidney disease", 90: 1115-1122.
Peyssonnaux et al., "HIF-1α Expression Regulates the Bactericidal Capacity of Phagocytes," J. Clinical Invest., 115(7): 1806-1815 (2005).
Piyamongkol et al., 2010, "Amido-3-hydroxypyridin-4-ones as Iron (III) Ligands", Chemistry A European Journal, vol. 16: 6374-6381.
Prabhakar et. al., 2012 "Adaptive and Maladaptive Cardiorespiratpry Responses to Continuous and Intermittent Hypoxia Mediated by Hypoxia-Inducible Factors 1 and 2", Physiol. Rev. , 92: 967-1003.
PubChem Open Chemistry Database Compound Name: SCHEMBL3484399 (CID 49848485); Retrieved on from the internet: <https://pubchem.ncbi.nlm.nih.gov/compound/49848485> on Mar. 15, 2016.
"PubChem Open Chemistry Database Compound Name: ZEADCOHJERWFOI-UHFFFAOYSA-M (CID 71491828); retrieved from the internet: <https://pubchem.ncbi.nlm.nih.gov/compound/71491828> on Mar. 21, 2016".
Qian et al., "A Randomized, Double-Blind, Placebo Controlled Trial of FG-4592 for Correction of Anemia in Subjects with Chronic Kidney Disease in China," Oral Abstract FR-ORO011, J. Am. Soc. Nephrol. 24:38A (2013).
Qunibi et al., 2011, "A randomized controlled trial comparing intravenous ferric carboxymaltose with oral iron for treatment of iron deficiency of non-dialysis-dependent chronic kidney disease patients", Nephrol Dial Transplant, 26(5): 1599-1607.
Rahtu-Korpela, 2014, "HIF Prolyl 4-Hydroxylase-2 Inhibition Improves Glucose and Lipid Metabolism and Protects Against Obesity and Metabolic Dysfunction," Diabetes 63:3324-:3333 (2014).
Rankin et. al., 2007, "Hypoxia-inducible factor-2 (HIF-2) regulates hepatic erythropoietin in vivo" J. Clin. Invest. 117: 1069-1076.
Ratcliffe et al., 2007 "HIF-1 and HIF-2: working alone or together in hypoxia?" J. Clin. Inv., 2007, 117(4): 862-865.
Redondo et al., 2000, "Vascular endothelial growth factor (VEGF) and melanoma. N-Acetylcysteine downregulates VEGF production in vitro", Cytokine, 12(4): 374-378.
Request for Correction of Inventorship at USPTO regarding U.S. Appl. No. 11/821,936.
Roda et al., 2012, "Stabilization of HIF-2a induces sVEGFR-1 production from tumor-associated macrophages and decreases tumor growth in a murine melanoma model", J. Immunology, 189: 3168-3177.
Schelass and Waldmann, 1996, "Protecting Group Strategies in Organic Synthesis". Chem. Int. Ed. Engl., 36:2056-2083.
Schoneberg et al., "Structural Basis of G Protein-Coupled Receptor Function," Molecular and Cellular Endocrinology, 151:181-193 (1999).
Search Report dated Apr. 28, 2011 for European Pat. App. No. 11000872.9.
Semenza et al., "Transcriptional Regulation of Genes Encoding Glycolytic Enzymes by Hypoxia-Inducible Factor 1," J. Biol. Chem., 269:23757-23763 (1994).

(56) References Cited

OTHER PUBLICATIONS

Semenza, "Regulation of Erythropoietin Production: New Insights into Molecular Mechanisms of Oxygen Homeostasis," Hematol. Oncol. Clin. North Am., 8:863-884 (1994).
Semenza, 2000, "HIF-1 and human disease: one highly involved factor", Genes & Development, 14: 1983-1991.
Semenza, "Signal Transduction to Hypoxia-inducible Factor 1," Biochem. Pharmacol, 64:993-998 (2002).
Sexton, "Recent advances in our understanding of peptide hormone receptors and RAMPS," Current Opinion in Drug Discovery and Development, 2(5):440-448 (1999).
Seymour et al., 2011, "Decision T 0777/08 of the Boards of Appeal of the European Patent Office", retrieved from the internet: <http://www.epo.org/law-practice/case-law-appeals/pdf/t080777exl.pdf> on Dec. 19, 2017.
Sheehan, "3-Hydroxypicolinic Acid and Some of its Derivatives," J. Organic Chemistry 31(1):636-6:38 (1996).
Siddiq, 2005, "Hypoxia-inducible factor prolyl 4-hydroxylase inhibition", Journal of Biological Chemistry, 280(50): 41732-41743.
Sowter et al., 2003 "Predominant Role of Hypoxia-Inducible Transcription Factor (Hif)-1α versus (Hif)-2α in Regulation of the Transcriptional Response to Hypoxia", Cancer Res., 63: 6130-6134.
Sporn and Suh, 2000, "Chemoprevention of cancer", Carcinogenesis, 21(3): 525-530.
Stille et. Al., 1986, Angew. Chem., Int. ED. Engl., vol. 25: 508.
Stohlawetz et al., 2000, "Effects of erythropoietin on platelet reactivity and thrombopoiesis in humans", Blood, 95(9): 2983-2989.
Sutter, 2000, "Hypoxia-inducible factor 1 alpha protein expression is controlled by oxygen-regulated ubiquitination that is disrupted by deletions and missense mutations", PNAS, 97(9): 4748-4753.
Teicher et al., "Potentiation of Cytotoxic Cancer Therapies by TNP-470 Alone and with Other Anti-Angiogenic Agents," Int. J. Cancer, 57:920-925 (1994).
Thornber, 1979, "Isosterism and Molecular Modification in Drug Design", Progress Drug Res., vol. 37: 563-580.
Thoppil and Bishayee, 2011, "Terpenoids as potential chemopreventitive and therapeutic agents in liver cancer", World J. Hepatol., 3(9): 228-249.
Tzschucke et al., "Fluorous-Silica-Supported Perfluoro-Tagged Palladium Complexes Catalyze Suzuki Coupling in Water" Helvetica Chimica Acta: vol. 87 2882-2889 (2004).
Ullman, F., 1901, J. Bielecki, Ber. Deutsch. Chem. Ges. P2174, 34.
Variankaval et al., 2008, "From form to unction: crystallization of active pharmaceutical ingredients", AICHE Journal, Jul. 2008, 54(7): 1682-1688.
Vickerstaffe et al., "Fully Automated Polymer-Assisted Synthesis of 1,5-Biaryl Pyrazoles," J. Comb. Chem., 2004, 6, 332-33.
Vippagunta et al., 2001, "Crystalline solids." Adv Drug Deliv Rev. 48(1):3-26.
Vincent et al., "Angiogenesis is Induced in a Rabbit Model of Hindlimb Ischemia by Naked DNA Encoding an HIF-1a/VP16 Hybrid Transcription Factor," Circulation, 102:2255-2261 (2000).
Wade et al., 2006, "Organic Chemistry", 6th ED., Pearson Prentice Hall, US: 780-781.
Warnecke et al., "Activation of the Hypoxia-Inducible Factor Pathway and Stimulation of Angiogenesis by Application of Prolyl Hydroxylase Inhibitors," FASEB Journal, 17: 1186-1188 (2003).
Warshakoon et al., "Design and synthesis of substituted pyridine derivatives as HIF-1alpha prolyl hydroxylase inhibitors," Bioorganic & Medicinal ChemisLiy Letters, 16 (2006) 5616-5620.
Wax el al., "SM-20 is a Novel20-kd Protein Whose Expression in the Arterial Wall is Restricted to Smooth Muscle," Lab. Invest., 74(4):797-808 (1996).
Weidner et al., "Tumor Angiogenesis and Metastasis—Correlation in Invasive Breast Carcinoma," New Eng. J. Med., 324(l):1-8 (1991).

Wiesener et al., 2003 "Widespread hypoxia-inducible expression of HIF-2alpha in distinct cell populations of different organs." FASEB J.17(2): 271-3.
Wright et al., "Activation of the Prolyl Hydroxylase Oxygen-Sensor Results in Induction of GLUTI, Heme Oxygenase-1, and Nitric-Oxide Synthase Proteins and Confers Protection from Metabolic Inhibition to Cardiomyocytes," J. Bio. Chem., 278(22):20235-20239 (2003).
Wu et. al., 2010 "A systems biology perspective on sVEGFRl: its biological function, pathogenic role and therapeutic use" J. Cell. Mol. Med. 14:528-552.
Yang et al., 2012, "Desmoplakin acts as a tumor suppressor by inhibition of the Wnt/beta-catenin signaling pathway in human lung cancer", Carcinogenesis, 33(10): 1863-1870.
Leuenberger et al., "Pharmaceutical powder technology—from art to science: the challenge of the FDA's Process Analytical Technology initiative", Advanced Powder Technol., vol. 16, No. 1, pp. 3-25 (2005) (Exhibit A).
Sun et al., "Development of a High Drug Load Tablet Formulation Based on Assessment of Powder Manufacturability: Moving Towards Quality by Design", Journal of Pharmaceutical Sciences, vol. 98, No. 1, pp. 239-247 (2009) (Exhibit B).
Wilson C. et al., Reprint of poster presentation at American Association of Pharmaceutical Scientists Meeting, 2003.
Exhibit C: Lee et al., "6.1 Pharmaceutical Preformulation: Physicochemical Properties of Excipients and Powders and Table Characterization," In: Pharmaceutical Manufacturing Handbook: Production and Processes (Ed. Shayne Cox Gad), pp. 881-931, John Wiley & Sons, 2008.
Exhibit D: Perumal et al., "6.2 Role of Preformulation In Development of Solid Dosage Forms," In: Pharmaceutical Manufacturing Handbook: Production and Processes (Ed. Shayne Cox Gad), pp. 933-975, John Wiley & Sons, 2008.
Exhibit E: Cavatur et al., "Chapter 14. Preformulation Studies for Tablet Formulation Development," In: Pharmaceutical Dosage Forms—Tablet: Unit Operations and Mechanical Properties (ed. Larry L. Ausberger and Stephen W. Hoag), Taylor & Francis Group, 2008, pp. 465-483.
Exhibit F: *Endo Pharms. Sols., Inc. v. Custopharm Inc.* 894 F.3d 1374 (Fed. Cir. 2018).
Exhibit G: *Genetics Inst., LLC v. Novartis Vaccines & Diagnostics, Inc.* 655 F.3d 1291 (Fed. Cir. 2011).
Hartman, C. S. el al. "Controlled hemoglobin response in a double-blind, placebo controlled trial of AKB-6548 in subjects with chronic kidney disease" Nephrology Dialysis Transplantation (2014-) vol. 29 Supplement 3, iii21-iii22, abstract SO051.
Besarab, A, et al. "Evaluation of hypoxia-inducible factor prolyl hydroxylase inhibitor FG-4592 for hemoglobin correction and maintenance in nondialysis chronic kidney disease patients for 16 and 24 weeks" Nephrology Dialysis Transplantation (2012) vol. 27 Supplement 2, 11144-11145, abstract FP215.
Yapa, S. W. S. et al. "Steady-state pharmacokinetics of GSK 1278863 and metabolites with normal and impaired renal function" Clinical Pharmacology & Therapeutics (Feb. 2015) vol. 97 Supplement 1, p. S92, abstract PII-106.
Steinmetz et al., "The basics of preclinical drug development for neurodegenerative disease indications," BMC Neurol. 2009;9 Suppl 1 (Suppl 1):S2, published Jun. 12, 2009, doi:10.1186/1471-2377-9-S1-S2.
Reprint of Crowley et al., "Drug-Excipient Interactions," Pharmaceutical Technology, 13:26-34, 2001.
Haywood et al., "Pharmaceutical excipients—where do we begin?" Australian Prescriber, 34(4):112-114, 2011.
Krapf et al. "Arterial Hypertension Induced by Erythropoietin and Erythropoiesis-Stimulating Agents (ESA)," Clin. J. Am. Soc. Nephrol., 4:470-80, 2009.
Waknine "Black Box Warning for Erythropoiesis-Stimulating Agents," Medscape, Mar. 12, 2017.

COMPOSITIONS AND METHODS FOR TREATING ANEMIA

This application is a national stage entry of International Patent Application No. PCT/US2016/025235, filed on Mar. 31, 2016, which claims the priority of and the benefit of the filing date of U.S. Provisional Application No. 62/270,168, filed Dec. 21, 2015, and U.S. Provisional Application No. 62/141,420, filed Apr. 1, 2015, which are herein incorporated in their entireties.

1 FIELD OF THE INVENTION

The present disclosure relates to uses of a HIF prolyl hydroxylase inhibitor in treating or preventing anemia, such as anemia secondary to or associated with chronic kidney disease, non-dialysis dependent chronic kidney disease, anemia associated with or resulting from chemotherapy, or anemia associated with AIDS. Further, the present disclosure relates to HIF prolyl hydroxylase inhibitor compounds and pharmaceutically acceptable salts thereof, compositions comprising the HIF prolyl hydroxylase inhibitor compounds, and to methods for treating or preventing diseases such as, Peripheral Vascular Disease (PVD), Coronary Artery Disease (CAD), heart failure, ischemia, hypoxia and anemia. In addition, the present disclosure relates to specific doses of, and dosing regimens for, uses of a HIF prolyl hydroxylase inhibitor in treating or preventing anemia, such as anemia secondary to or associated with chronic kidney disease, anemia associated with or resulting from chemotherapy, or anemia associated with AIDS.

2 BACKGROUND OF THE INVENTION

Hypoxia-inducible factor (HIF) is a transcription factor that is a key regulator of responses to hypoxia. In response to hypoxic conditions, i.e., reduced oxygen levels in the cellular environment, HIF upregulates transcription of several target genes, including those encoding erythropoietin. HIF is a heteroduplex comprising an alpha and beta subunit. While the beta subunit is normally present in excess and is not dependent on oxygen tension, the HIF-alpha subunit is only detectable in cells under hypoxic conditions. In this regard, the accumulation of HIF-alpha is regulated primarily by hydroxylation at two proline residues by a family of prolyl hydroxylases known as HIF prolyl hydroxylases, wherein hydroxylation of one or both of the proline residues leads to the rapid degradation of HIF-alpha. Accordingly, inhibition of HIF prolyl hydroxylase results in stabilization and accumulation of HIF-alpha (i.e., the degradation of HIF-alpha is reduced), thereby leading to an increase in the amount of HIF-alpha available for formation of the HIF heterodimer and upregulation of target genes, such as the Erythropoietin gene. Conversely, activation of HIF prolyl hydroxylase results in destabilization of HIF-alpha (i.e., the degradation of HIF-alpha is increased), thereby leading to a decrease in the amount of HIF-alpha available for formation of the HIF heterodimer and downregulation of target genes, such as VEGF.

The family of hypoxia inducible factors includes HIF-1-alpha, HIF-2-alpha, and HIF-3-alpha.

A new class of prolyl hydroxylase inhibitors and their use to treat or prevent diseases ameliorated by modulation of hypoxia-inducible factor (HIF) prolyl hydroxylase are described in U.S. Pat. No. 7,811,595, which is incorporated herein by reference in its entirety. The synthesis of such prolyl hydroxylase inhibitors is described in U.S. Patent Publication No. 2012/0309977, which is incorporated herein by reference in its entirety. Such compounds inhibit HIF prolyl hydroxylase, thereby stabilizing HIF-alpha. As a consequence of stabilizing HIF-alpha, endogenous erythropoietin (EPO) production is increased. As with all drugs, proper doses and dosing regimens for treating patients having diseases such as anemia are essential for achieving a desired or optimal therapeutic effect without adverse effects or unwanted side-effects. Indeed, many active compounds fail in clinical trials because an effective and safe dosing regimen cannot be found.

The use of prolyl hydroxylase inhibitors and their use to treat or prevent diseases ameliorated by modulation of hypoxia-inducible factor (HIF) prolyl hydroxylase using certain dosing regimens is described in the International Publication No. WO/2014/200773, which is incorporated herein by reference in its entirety. Described therein are also treatment regimens that modulate EPO so as to raise the total iron binding capacity (TIBC) relative to a baseline TIBC in a patient, without significantly increasing the serum iron level relative to a baseline serum iron level, and methods of administration of prolyl hydroxylase inhibitors so as to raise the serum hemoglobin levels relative to a baseline serum hemoglobin level in a patient, without significantly decreasing hepcidin expression relative to a baseline hepcidin expression level.

3 SUMMARY OF THE INVENTION

Described herein is an oral dosage formulation comprising intra-granular components, extra-granular components, and film coating components, wherein the intra-granular components comprise Compound 1, an insoluble diluent or carrier, a disintegrant, and a diluent or filler; wherein the extra-granular components comprise a disintegrant, a glidant, and/or a lubricant; and wherein the film coating components comprise a tablet coating.

Described herein is an oral dosage formulation comprising intra-granular components, extra-granular components, and film coating components, wherein the intra-granular components comprise Compound 1, microcrystalline cellulose, sodium starch glycolate, and hydroxypropyl methylcellulose, wherein the extra-granular components comprise sodium starch glycolate, colloidal silicon dioxide, and magnesium stearate, and wherein the film-coating components comprise Opadry®.

Described herein is a method for treating anemia comprising administering to a patient a formulation comprising intra-granular components, extra-granular components, and film coating components, wherein the intra-granular components comprise Compound 1, an insoluble diluent or carrier, a disintegrant, and a diluent or filler; wherein the extra-granular components comprise a disintegrant, a glidant, and/or a lubricant; and wherein the film coating components comprise a tablet coating.

Described herein is a method for treating anemia comprising administering to a patient a formulation comprising intra-granular components, extra-granular components, and film coating components, wherein the intra-granular components comprise Compound 1, microcrystalline cellulose, sodium starch glycolate, and hydroxypropyl methylcellulose, wherein the extra-granular components comprise sodium starch glycolate, colloidal silicon dioxide, and magnesium stearate, and wherein the film-coating components comprise Opadry®.

Described herein is a method for treating anemia secondary to non-dialysis dependent chronic kidney disease, comprising administering to a patient having anemia secondary to non-dialysis dependent chronic kidney disease an effective amount of a compound which is {[5-(3-chlorophenyl)-3-hydroxypyridine-2-carbonyl]amino}acetic acid or a pharmaceutically acceptable salt, solvate, or hydrate thereof, wherein a daily dose comprises about 150 mg, about 300 mg, about 450 mg, about 600 mg, or about 750 mg of the compound.

Described herein is a method of treating a anemia secondary to non-dialysis dependent chronic kidney disease, comprising administering a sufficient number of successive doses of a HIF prolyl hydroxylase inhibitor or a HIF-alpha stabilizer to a patient having anemia secondary to non-dialysis dependent chronic kidney disease wherein the patient has at least 2, 3, 4, 5 or all of (i) an estimated glomerular filtration rate (eGFR) of less than 60 mL/min/1.73 m$^2$, wherein the subject is not on dialysis and not expected to start dialysis within 3 months of beginning of treatment, (ii) a hemoglobin level of less than 10.0 g/dL prior to commencement of treatment, (iii) a ferritin level equal to or above 100 ng/mL within 4 weeks of commencement of treatment, (iv) a transferrin saturation (TSAT) level equal to or above 20% within 4 weeks commencement of treatment, (v) a folate measurement equal to or above the lower limit of normal within 4 weeks commencement of treatment, (vi) a vitamin B12 measurement equal to or above the lower limit of normal within 4 weeks commencement of treatment, and (vii) an age of at least 18 years.

Described herein is a method of treating a anemia secondary to non-dialysis dependent chronic kidney disease, comprising administering a sufficient number of successive doses of a HIF prolyl hydroxylase inhibitor or a HIF-alpha stabilizer to a patient having anemia secondary to non-dialysis dependent chronic kidney disease wherein the patient has at least 2, 3, 4, 5 or all of (i) an estimated glomerular filtration rate (eGFR) of less than 65 mL/min/1.73 m$^2$, wherein the subject is not on dialysis and not expected to start dialysis within 3 months of beginning of treatment, (ii) a hemoglobin level of less than 10.0 g/dL prior to commencement of treatment, (iii) a ferritin level equal to or above 50 ng/mL within 4 weeks of commencement of treatment, (iv) a transferrin saturation (TSAT) level equal to or above 15% within 4 weeks commencement of treatment, (v) a folate measurement equal to or above the lower limit of normal within 4 weeks commencement of treatment, (vi) a vitamin B12 measurement equal to or above the lower limit of normal within 4 weeks commencement of treatment, and (vii) an age of at least 18 years.

Described herein is a method for treating anemia in a patient having non-dialysis dependent chronic kidney disease comprising: (i) administering to the patient an initial daily dose of Compound 1; (ii) if the Hgb has not increased by more than 0.5 g/dL above the baseline value after 4 weeks of daily administration at the initial daily dose of Compound 1, increasing the daily dose by 150 mg/day of Compound 1, and increasing the daily dose by 150 mg/day every 4 weeks until Hgb is above 10.0 g/dL; (iii) if the Hgb rises rapidly during treatment, reducing the daily dose by 150 mg/day; (iv) if the Hgb falls below 10.0 g/dL, increasing the daily dose by 150 mg/day; (v) if the Hgb level exceeds 11.0 g/dL, interrupting treatment until the Hgb decreases to 10.5 g/dL or less, and thereafter resuming dosing with a daily dose reduced by 150 mg/day; and (vi) if a dose adjustment is required to maintain Hgb at the desired level, adjusting the daily dose by 150 mg/day.

Described herein is a method for treating anemia in a patient having non-dialysis dependent chronic kidney disease comprising: (i) administering to the patient an initial daily dose of Compound 1; (ii) if the Hgb has not increased by more than 0.5 g/dL above the baseline value after 4 weeks of daily administration at the initial daily dose of Compound 1, increasing the daily dose by 150 mg/day of Compound 1, and increasing the daily dose by 150 mg/day every 4 weeks until Hgb is above 10.0 g/dL; (iii) if the Hgb rises rapidly during treatment, reducing the daily dose by 150 mg/day; (iv) if the Hgb falls below 10.0 g/dL, increasing the daily dose by 150 mg/day; (v) if the Hgb level exceeds 12.0 g/dL, reducing the daily dose by 150 mg/day, and if Hgb level exceeds 13.0 g/dL, interrupting treatment until the Hgb decreases to 12.5 g/dL or less, and thereafter resuming dosing with a daily dose reduced by 150 mg/day; and (vi) if a dose adjustment is required to maintain Hgb at the desired level, adjusting the daily dose by 150 mg/day.

Described herein is a method for treating anemia in a patient having non-dialysis dependent chronic kidney disease comprising: (i) administering to the patient an initial daily dose of Compound 1; (ii) if a dose adjustment is required to maintain Hgb at the desired level, adjusting the daily dose by 150 mg/day; (iii) if the Hgb rises rapidly during treatment, reducing the daily dose by 150 mg/day; (iv) if the Hgb falls below 10.0 g/dL, increasing the daily dose by 150 mg/day; and (v) if the Hgb level exceeds 11.0 g/dL, interrupting treatment until the Hgb decreases to 10.5 g/dL or less, and thereafter resuming dosing with a daily dose reduced by 150 mg/day.

Described herein is a method for treating anemia in a patient having non-dialysis dependent chronic kidney disease comprising: (i) administering to the patient an initial daily dose of Compound 1; (ii) if a dose adjustment is required to maintain Hgb at the desired level, adjusting the daily dose by 150 mg/day; (iii) if the Hgb rises rapidly during treatment, reducing the daily dose by 150 mg/day; (iv) if the Hgb falls below 10.0 g/dL, increasing the daily dose by 150 mg/day; and (v) if the Hgb level exceeds 12.0 g/dL, reducing the daily dose by 150 mg/day, and if Hgb level exceeds 13.0 g/dL, interrupting treatment until the Hgb decreases to 12.5 g/dL or less, and thereafter resuming dosing with a daily dose reduced by 150 mg/day.

In certain embodiments, the baseline value is determined immediately prior to the first administration of Compound 1.

In certain embodiments, the Hgb rises rapidly if the Hgb rises more than 1.0 g/dL in any 2-week period.

In certain embodiments, the maximum daily dose is 600 mg/day.

In certain embodiments, the daily dose is not increased more frequently than once every 4 weeks during the course of treatment.

In certain, more specific embodiments, decrease in daily dose can occur more frequently than once every 4 weeks during the course of treatment.

In certain embodiments, the initial daily dose is 300 mg/day.

In certain embodiments, the initial daily dose is administered in form of two tablets of 150 mg of Compound 1 each.

In certain embodiments, the initial daily dose is 450 mg/day.

In certain embodiments, the initial daily dose is administered in form of three tablets of 150 mg of Compound 1 each.

In certain embodiments, the initial daily dose is administered in the morning.

In certain embodiments, the initial daily dose is administered between 7 am and 2 pm.

In certain embodiments, Compound 1 is administered in the form of Formulation 1.

In certain embodiments, Compound 1 is administered in the form of Formulation 2.

4 BRIEF DESCRIPTION OF THE FIGURES

FIG. 1A: Relative Bioavailability Results—Plasma concentration of Compound 1 administered as tablet Formulation 1 and Formulation 2 as described in Section 6.2, shown as linear plot.

Figure 1B:
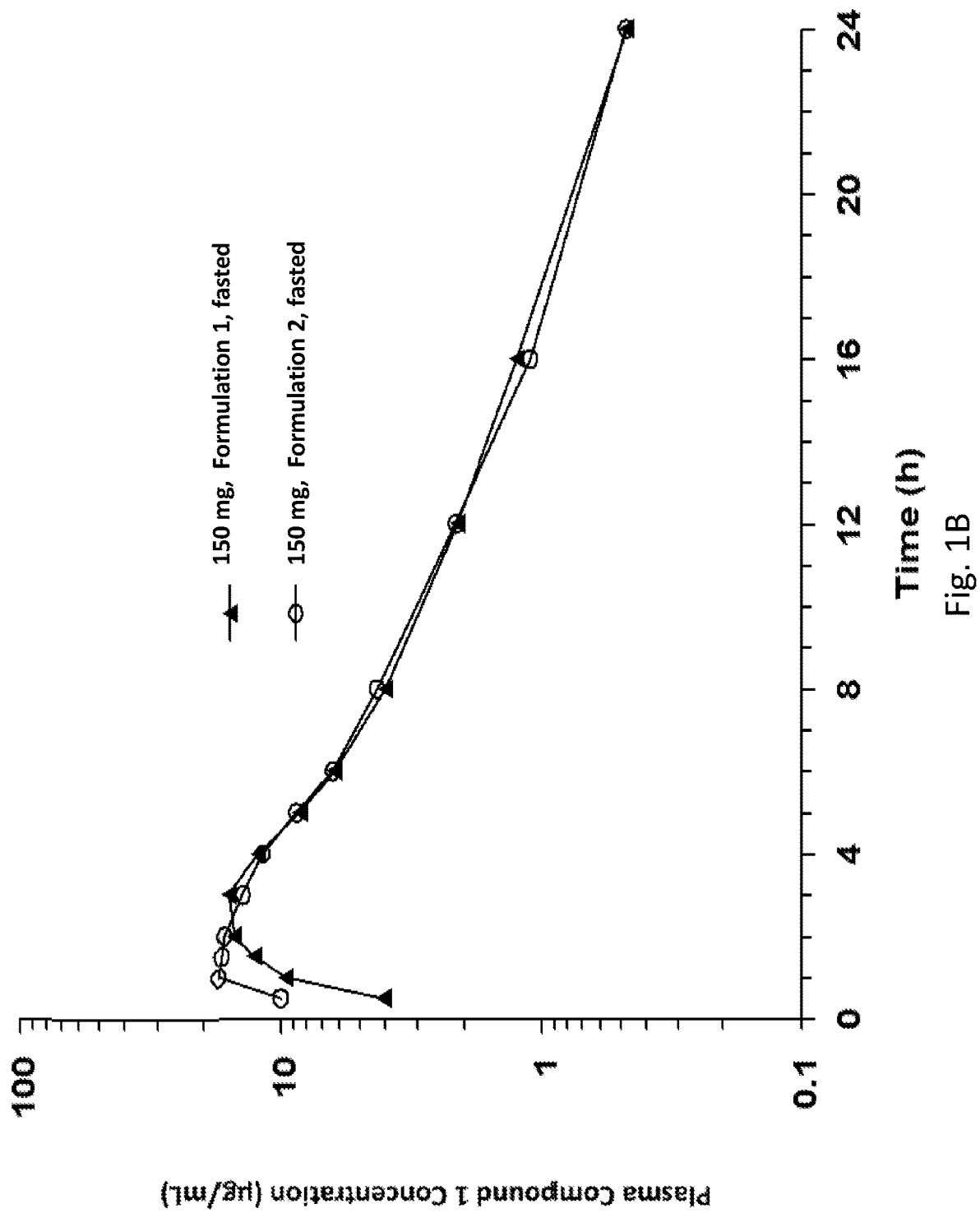

FIG. 1B: Relative Bioavailability Results—Plasma concentration of Compound 1 administered as tablet Formulation 1 and Formulation 2 as described in Section 6.2, shown as semi-log plot.

Figure 2A:
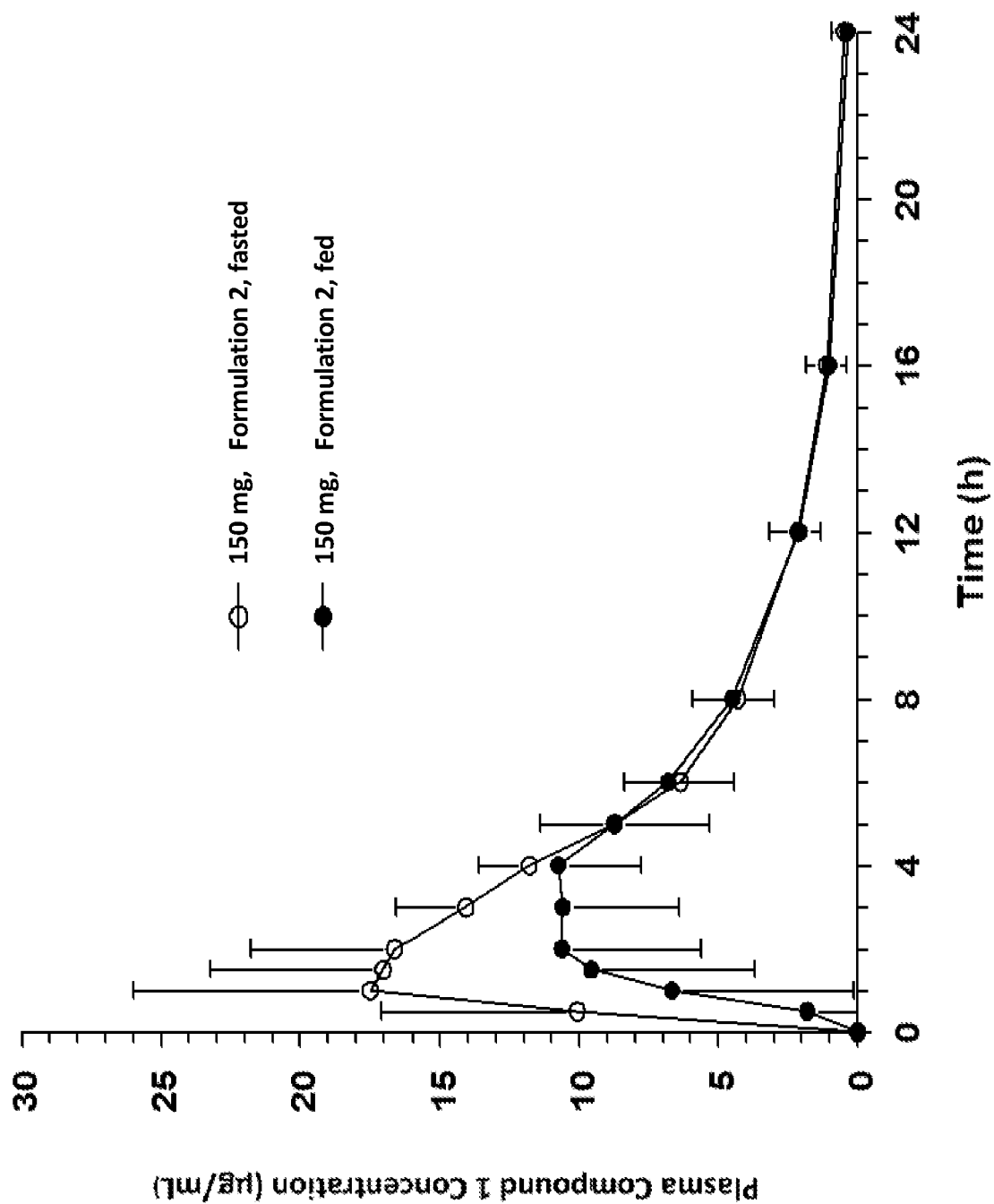

FIG. 2A: Food Effect Results—Plasma concentration of Compound 1 administered as tablet Formulation 2 as described in Section 6.2 under fed and fasted conditions, shown as linear plot.

Figure 2B:
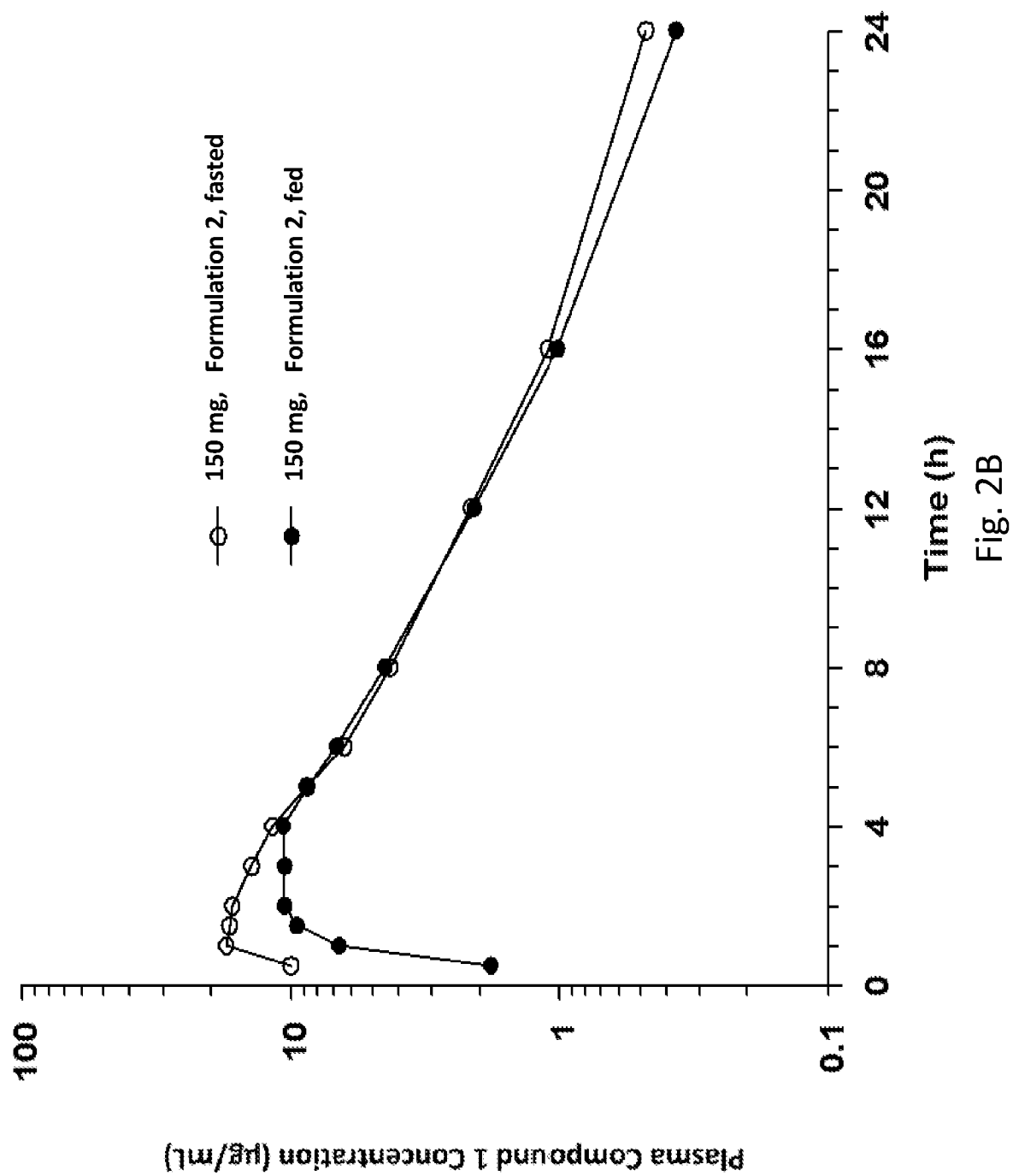

FIG. 2B: Food Effect Results—Plasma concentration of Compound 1 administered as tablet Formulation 2 as described in Section 6.2 under fed and fasted conditions, shown as semi-log plot.

5 DETAILED DESCRIPTION

In certain embodiments, provided herein is a method for treating or preventing anemia in a patient, wherein the method comprises administering to the patient a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 or a pharmaceutically acceptable salt, solvate, or hydrate thereof. In certain embodiments, the patient has anemia secondary to non-dialysis dependent chronic kidney disease. In certain embodiments, the pharmaceutically effective amount is suitable to increase the level of hemoglobin by at least about 0.2 g/dL, 0.3 g/dL, 0.4 g/dL, 0.5 g/dL, by at least about 0.6 g/dL, by at least about 0.7 g/dL, by at least about 0.8 g/dL, by at least about 0.9 g/dL, by at least about 1.0 g/dL, by at least about 1.2 g/dL, or by at least about 1.5 g/dL relative to a baseline hemoglobin level in the patient while: a) restoring or maintaining the diurnal pattern of EPO serum levels; and/or b) increasing the total iron binding capacity; and/or c) increasing the total iron binding capacity without increasing significantly the total iron levels; and/or d) not significantly decreasing hepcidin levels.

General methods of treatment are described in Section 5.5. Diseases treatable with the compounds and methods described herein are described in Section 5.6. Treatment and dosing regimens using these compounds are described in Section 5.7. Combination therapies using the compositions described herein are described in Section 5.8. The specific patient populations to be treated with the compounds and methods described herein are described in Section 5.4. Specific formulations to be used in the dosing regimens for the patient populations described herein are described in Section 5.3.

5.1 Definitions and Abbreviations

In certain embodiments, as used throughout the description and claims of this specification the word "comprise" and other forms of the word, such as "comprising" and "comprises," means including but not limited to, and is not intended to exclude, for example, other additives, components, integers, or steps. In certain embodiments, as used in the description and the appended claims, the singular forms "a," "an," and "the" include plural referents unless the context clearly dictates otherwise. Thus, for example, reference to "a composition" includes mixtures of two or more such compositions. In certain embodiments, "optional" or "optionally" means that the subsequently described event or circumstance can or cannot occur, and that the description includes instances where the event or circumstance occurs and instances where it does not As used herein, an "alkyl" group is a saturated straight chain or branched non-cyclic hydrocarbon having, for example, from 1 to 12 carbon atoms, 1 to 9 carbon atoms, 1 to 6 carbon atoms, 1 to 4 carbon atoms, or 2 to 6 carbon atoms. Representative alkyl groups include -methyl, -ethyl, -n-propyl, -n-butyl, -n-pentyl and -n-hexyl; while branched alkyls include -isopropyl, -sec-butyl, -iso-butyl, -tert-butyl, -iso-pentyl, 2-methylpentyl, 3-methylpentyl, 4-methylpentyl, 2,3-dimethylbutyl and the like.

$C_{1-6}$ alkyl units include the following non-limiting examples: methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), tert-pentyl ($C_5$), neo-pentyl ($C_5$), iso-pentyl ($C_5$), sec-pentyl ($C_5$), 3-pentyl ($C_5$), n-hexyl ($C_6$), iso-hexyl ($C_6$), neo-hexyl ($C_6$), 3-methylpentyl ($C_6$), 4-methylpentyl ($C_6$), 3-methylpentan-2-yl ($C_6$), 4-methylpentan-2-yl ($C_6$), 2,3-dimethylbutyl ($C_6$), 3,3-dimethylbutan-2-yl ($C_6$), 2,3-dimethylbutan-2-yl ($C_6$), and the like.

As used herein, an "alkenyl" group is a partially unsaturated straight chain or branched non-cyclic hydrocarbon containing at least one carbon-carbon double bond and having, for example, from 1 to 6 carbon atoms. Representative alkenyl groups include propenyl and the like.

As used herein, an "alkynyl" group is a partially unsaturated straight chain or branched non-cyclic hydrocarbon containing at least one carbon-carbon triple bond and having, for example, from 2 to 6 carbon atoms. Representative alkynyl groups include propynyl, butynyl and the like.

As used herein, an "alkoxy" group is an alkyl-O— group in which the alkyl group is as defined herein. Representative alkoxy groups include methoxy, ethoxy, n-propoxy, iso-propoxy and n-butoxy.

As used herein, a "cycloalkyl" group is a saturated cyclic alkyl group of from 3 to 6 carbon atoms having a single cyclic ring. Representative cycloalkyl groups include cyclopropyl, cyclobutyl, cyclopentyl, and cyclohexyl.

As used herein, a "cycloalkenyl" group is a partially unsaturated cyclic alkyl group containing at least one carbon-carbon double bond and from 3 to 6 carbon atoms having a single cyclic ring. Representative cycloalkenyl groups include cyclopropenyl and cyclobutenyl.

As used herein, a "cycloalkoxy" group is a cycloalkyl-O— group in which the cycloalkyl group is as defined herein. Representative cycloalkoxy groups include cyclopropyloxy, cyclobutyloxy, cyclopentyloxy, and cyclohexyloxy.

As used herein, a "haloalkyl" group is an alkyl group as defined herein above with one or more (e.g., 1 to 5) hydrogen atoms are replaced by halogen atoms. Representative haloalkyl groups include $CF_3$, $CHF_2$, $CH_2F$, $CCl_3$, $CF_3CH_2CH_2$ and $CF_3CF_2$.

As used herein, a "halocycloalkyl" group is a cycloalkyl group as defined herein above with one or more (e.g., 1 to 5) hydrogen atoms are replaced by halogen atoms. Representative halocycloalkyl groups include 2,2-difluorocyclopropyl, 2,2-dichlorocyclopropyl, 2,2-dibromocyclopropyl, tetrafluorocyclopropyl, 3,3-difluorocyclobutyl and 2,2,3,3-tetrafluorocyclobutyl.

As used herein, a "heterocycloalkyl" group is a saturated ring of 4 to 7 atoms, preferably 5 or 6 ring atoms, wherein 1 or 2 ring members are selected from the group consisting of O, S and NR" and the remaining atoms are carbon. There are no adjacent oxygen and/or sulfur atoms in the rings. Representative heterocycloalkyl groups are piperidyl, pyrrolidinyl, piperazinyl, morpholinyl, thiomorpholinyl, thiazolidinyl, 1,3-dioxolanyl, 1,4-dioxanyl, oxazolinyl, tetrahydrofuranyl, tetrahydrothiophenyl and tetrahydrothiopyranyl.

As used herein, an "aryl" group is an aromatic monocyclic or multi-cyclic ring system comprising 6 to 10 carbon atoms. Representative aryl groups include phenyl and naphthyl.

As used herein, a "heteroaryl" is a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Representative single-ring heteroaryl groups include pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Representative bicyclic heteroaryl groups are naphthyridyl (e.g., 1,5 or 1, 7), imidazopyridyl, pyridopyrimidinyl and 7-azaindolyl. Representative benzofused heteroaryl groups include indolyl, quinolyl, isoquinolyl, phthalazinyl, benzothienyl (i.e., thianaphthenyl), benzimidazolyl, benzofuranyl, benzoxazolyl, benzisoxazolyl, benzothiazolyl and benzofurazanyl. All positional isomers are contemplated, e.g., 2-pyridyl, 3-pyridyl and 4-pyridyl.

For the purposes of the present disclosure the terms "compound," "analog," and "composition of matter" stand equally well for the HIF prolyl hydroxylase enzyme inhibitors described herein, including all enantiomeric forms, diastereomeric forms, salts, tautomers, and the like. The compounds disclosed herein include all salt forms, for example, salts of both basic groups, inter alia, amines, as well as salts of acidic groups, inter alia, carboxylic acids. The following are non-limiting examples of anions that can form pharmaceutically acceptable salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form pharmaceutically acceptable salts of the anionic form of acidic substituent groups on the compounds described herein: sodium, lithium, potassium, calcium, magnesium, zinc, bismuth, and the like. The following are non-limiting examples of cations that can form pharmaceutically acceptable salts of the anionic form of phenolic, aryl alcohol, or heteroaryl alcohol substituent groups on the compounds described herein: sodium, lithium, and potassium. In certain embodiments, terms "compound," "analog," and "composition of matter" are used interchangeably throughout the present specification.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As used herein, the term "anemia" is art-recognized and is defined by hemoglobin threshold as follows:

| Age or Gender Group | Hemoglobin Threshold (g/dL) |
| --- | --- |
| Children (0.50-4.99 yrs.) | 11.0 |
| Children (5.00-11.99 yrs.) | 11.5 |
| Children (12.00-14.99 yrs.) | 12.0 |
| Non-pregnant Women (≥15.00 yrs) | 12.0 |
| Pregnant Women | 11.0 |
| Men (≥15.00 yrs) | 13.0 |

Anemia may be chronic (e.g., anemia secondary to chronic kidney disease, anemia secondary to chronic heart failure, idiopathic anemia of aging, anemia of chronic disease, such as inflammatory bowel disease or rheumatoid arthritis, myelodysplastic syndrome, bone marrow fibrosis, and other aplastic or dysplastic anemias), subacute (e.g., chemotherapy induced anemia, such as chemotherapy for treating cancer, hepatitis C, or other chronic disease that reduces bone marrow production), acute (e.g., blood loss from injury or surgery), nutrition related (e.g., iron deficiency or vitamin B12 deficiency), or hemaglobinpathies (e.g., sickle cell disease, thalassemia, etc.), or anemia due to prematurity, or anemia due to autologous blood donation.

As used herein the term "non-severe anemia" refers to a patient having anemia wherein the hemoglobin is at least 9.0 g/dL. In certain such embodiments, non-severe anemia refers to anemia in a patient, wherein the patient does not require a transfusion.

As used herein, the term "dose(s)" means a quantity of the compound or a pharmaceutically acceptable salt, solvate, or hydrate thereof to be administered at one time. A dose may comprise a single unit dosage form, or alternatively may comprise more than a single unit dosage form (e.g., a single dose may comprise two tablets), or even less than a single unit dosage form (e.g., a single dose may comprise half of a tablet). Accordingly, if the compound is administered at a daily dose of 450 mg, once daily, then the dose of compound may be three tablets, each comprising 150 mg of compound administered once daily.

As used herein, the term "daily dose" means a quantity of the compound, or a pharmaceutically acceptable salt, solvate, or hydrate thereof that is administered in a 24 hour period. Accordingly, a daily dose may be administered all at once (i.e., once daily dosing) or alternatively the daily dosing may be divided such that administration of the compound is twice daily, three times daily, or even four times daily. When a daily dose is administered every day without interruption, the dosing is referred to as "continuous" dosing.

As used herein, the term "unit dosage form(s)" includes tablets; caplets; capsules, such as soft elastic gelatin capsules; sachets; cachets; troches; lozenges; dispersions; powders; solutions; gels; liquid dosage forms suitable for oral or mucosal administration to a patient, including suspensions (e.g., aqueous or non-aqueous liquid suspensions), emulsions (e.g., oil-in-water emulsions, or a water-in-oil liquid emulsion), solutions, and elixirs; and sterile solids (e.g., crystalline or amorphous solids) that can be reconstituted to provide liquid dosage forms suitable for oral or parenteral administration to a patient. The unit dosage form does not necessarily have to be administered as a single dose nor does a single unit dosage form necessarily constitute an entire dose.

As used herein, an "effective amount" refers to that amount of a compound or a pharmaceutically acceptable salt, solvate or hydrate thereof sufficient to provide a therapeutic benefit in the treatment of the disease or to delay or minimize symptoms associated with the disease. Certain preferred effective amounts are described herein. In certain embodiments, the compound is a compound disclosed herein.

As used herein, the terms "prevent," "preventing" and "prevention" are art-recognized, and when used in relation to a condition, such as a local recurrence (e.g., pain), a disease such as cancer, a syndrome complex such as heart failure or any other medical condition, is well understood in the art, and includes administration of a compound provided herein or a pharmaceutically acceptable salt, solvate or hydrate thereof, which reduces the frequency of, or delays the onset of, symptoms of a medical condition in a subject relative to a subject which does not receive the composition. In certain embodiments, the compound is a compound that is not disclosed herein. In certain embodiments, the condition is a disease or condition related to diminished endogenous production of erythropoietin (EPO) or a disease or condition related to deficiencies in endogenous hemoglobin production, such as anemia or anemia secondary to chronic kidney disease.

As used herein, the terms "treat," "treating" and "treatment" refer to the reversing, reducing, or arresting the symptoms, clinical signs, and underlying pathology of a condition in manner to improve or stabilize a subject's condition. The terms "treat" and "treatment" also refer to the eradication or amelioration of the disease or symptoms associated with the disease. In certain embodiments, such terms refer to minimizing the spread or worsening of the disease resulting from the administration of a compound provided herein or a pharmaceutically acceptable salt, solvate or hydrate thereof to a patient with such a disease.

As used herein, the term "pharmaceutically acceptable salt" refers to a salt prepared from pharmaceutically acceptable non-toxic acids or bases including inorganic acids and bases and organic acids and bases. Suitable pharmaceutically acceptable base addition salts for a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, and Metabolite 2 include, but are not limited to, sodium, lithium, potassium, calcium, magnesium, zinc, bismuth, ammonium (including alkyl substituted ammonium), amino acids (e.g., lysine, ornithine, arginine, or glutamine), tromethamine, and meglumine. Suitable non-toxic acids include, but are not limited to, inorganic and organic acids such as acetic, alginic, anthranilic, benzenesulfonic, benzoic, camphorsulfonic, citric, ethanesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Other examples of salts are well known in the art, see, e.g., Remington's Pharmaceutical Sciences, 22nd ed., Pharmaceutical Press, (2012).

In certain embodiments, "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

As used herein, the term "hydrate" means a compound provided herein or a pharmaceutically acceptable salt thereof, that further includes a stoichiometric or non-stoichiometric amount of water bound by non-covalent intermolecular forces.

As used herein, the term "solvate" means a compound provided herein or a pharmaceutically acceptable salt thereof, that further includes a stoichiometric or non-stoichiometric amount of a solvent, other than water, bound by non-covalent intermolecular forces.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range. In certain embodiments, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In certain embodiments, the term subject or patient can refer to a mammal, such as a human, mouse, dog, donkey, horse, rat, guinea pig, or monkey. In specific embodiments, a subject or a patient is a human subject or patient.

In certain embodiments, a compound provided herein is Compound 1, namely {[5-(3-chlorophenyl)-3-hydroxypyridine-2-carbonyl]amino}acetic acid having the structure

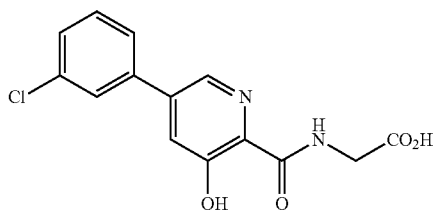 [SMILES: O=C(O)CNC(=O)c1ncc(-c2cccc(Cl)c2)cc1O]

In certain embodiments, the compound may be {[5-(3-chlorophenyl)-3-hydroxypyridine-2-carbonyl]amino}acetic acid, while in certain alternative embodiments, the compound may be a pharmaceutically acceptable salt of {[5-(3-chlorophenyl)-3-hydroxypyridine-2-carbonyl]amino}acetic acid. In certain alternative embodiments, the compound may be a solvate of {[5-(3-chlorophenyl)-3-hydroxypyridine-2-carbonyl]amino}acetic acid. In certain alternative embodiments, the compound may be a hydrate of {[5-(3-chlorophenyl)-3-hydroxypyridine-2-carbonyl]amino}acetic acid. In certain preferred embodiments, the invention relates to the compound in its parent form (i.e., not a salt, solvate, or hydrate). In certain alternative preferred embodiments, the invention relates to the compound or a pharmaceutically acceptable salt thereof.

In certain embodiments, a compound provided herein is Compound 7, namely {[5-(3-fluorophenyl)-3-hydroxypyridine-2-carbonyl]amino}acetic acid having the structure

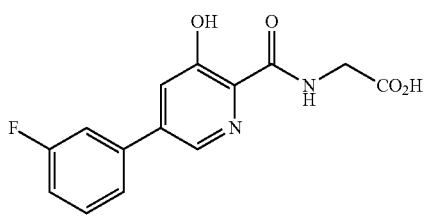

In certain embodiments, the compound may be {[5-(3-fluorophenyl)-3-hydroxypyridine-2-carbonyl]amino}acetic acid, while in certain alternative embodiments, the compound may be a pharmaceutically acceptable salt of {[5-(3-fluorophenyl)-3-hydroxypyridine-2-carbonyl]amino}acetic acid. In certain alternative embodiments, the compound may be a solvate of {[5-(3-fluorophenyl)-3-hydroxypyridine-2-carbonyl]amino}acetic acid. In certain alternative embodiments, the compound may be a hydrate of {[5-(3-fluorophenyl)-3-hydroxypyridine-2-carbonyl]amino}acetic acid. In certain preferred embodiments, the invention relates to the compound in its parent form (i.e., not a salt, solvate, or hydrate). In certain alternative preferred embodiments, the invention relates to the compound or a pharmaceutically acceptable salt thereof.

As used herein, the term "HIF prolyl hydroxylase" is art-recognized and may be abbreviated as "PHD." HIF prolyl hydroxylase is also known as "prolyl hydroxylase domain-containing protein" which may be abbreviated as "PHD." In this regard, there are three different PHD isoforms, PHD1, PHD2, and PHD3, also referred to as EGLN2, EGLN1, and EGLN3, or HPH3, HPH2, and HPH1, respectively. In certain embodiments, HIF prolyl hydroxylase may refer to a particular target of the enzyme (e.g., HIF-1α prolyl hydroxylase, HIF-2a prolyl hydroxylase, and/or HIF-3a prolyl hydroxylase).

As used herein, "Formulation 1" and "Formulation 2" are pharmaceutical formulations of Compound 1 as described in Section 6.2.

Further abbreviations and acronyms are given in the table below.

| | |
|---|---|
| ACTH | adrenocorticotropic hormone |
| AE | adverse event |
| ALT | alanine aminotransferase (SGPT) |
| ANOVA | analysis of variance |
| AST | aspartate aminotransferase (SGOT) |
| BUN | blood urea nitrogen |
| C | Celsius |
| CBC | complete blood count |
| CHF | congestive heart failure |
| CKD | chronic kidney disease |
| CKD-EPI | Chronic Kidney Disease Epidemiology Collaboration |
| CMH | Cochran-Mantel-Haenszel |
| CPK | creatine phosphokinase |
| CRF | case report form |
| CRO | contract research organization |
| CS | clinically significant |
| CV | cardiovascular |
| CVD | cardiovascular disease |
| dL | deciliter |
| DVT | deep venous thrombosis |
| EAC | Endpoint Adjudication Committee |
| ECG | electrocardiogram |
| EDC | electronic data capture |
| eGFR | estimated glomerular filtration rate |
| EOT | end of treatment |
| EPO | erythropoietin |
| ESA | erythropoiesis-stimulating agent |
| ESRD | end-stage renal disease |
| EU | European Union |
| F | Fahrenheit |
| FDA | Food and Drug Administration |
| g | gram |
| GCP | Good Clinical Practice |
| GFR | glomerular filtration rate |
| GMP | Good Manufacturing Practice |
| HA | health authority |
| HDL | high-density lipoprotein |
| Hgb | hemoglobin |
| HIF | hypoxia-inducible factor |
| HIFPH | hypoxia-inducible factor prolyl-hydroxylase |
| HIF-PHI | hypoxia-inducible factor prolyl-hydroxylase inhibitor |
| $IC_{50}$ | 50% inhibitory concentration |
| ICH | International Conference on Harmonization |
| IDMC | Independent Data Monitoring Committee |
| IDMS | isotope dilution mass spectrometry |
| IEC | independent ethics committee |
| INR | international normalized ratio |
| IRB | institutional review board |
| IV | intravenous(ly) |
| IWR | interactive web response |
| JSDT | Japanese Society for Dialysis Therapy |
| JSN | Japanese Society of Nephrology |
| KDIGO | Kidney Disease: Improving Global Outcomes |
| kg | kilogram |
| LDH | lactate dehydrogenase |
| LDL | low-density lipoprotein |
| LLN | lower limit of normal |
| MACE | major adverse cardiovascular events |
| MCH | mean corpuscular (cell) hemoglobin |
| MCHC | mean corpuscular (cell) hemoglobin concentration |
| MCV | mean corpuscular (cell) volume |
| MedDRA | Medical Dictionary for Regulatory Activities |
| μM | micromolar |
| mg | milligram |
| mL | milliliter |
| mRNA | messenger ribonucleic acid |
| MTD | maximum tolerated dose |
| NDD-CKD | non-dialysis dependent chronic kidney disease |
| ng | nanogram |
| PD | pharmacodynamics(s) |
| PE | pulmonary embolism |
| PHD | prolyl 4-hydroxylase domain |
| PK | pharmacokinetic(s) |
| PP | per protocol |

-continued

| | |
|---|---|
| PT | prothrombin time |
| PTT | partial thromboplastin time |
| QA | quality assurance |
| QC | quality control |
| RBC | red blood cell |
| RDW | red cell distribution width |
| ROW | rest of world |
| SAE | serious adverse event |
| SAP | Statistical Analysis Plan |
| SC | subcutaneous(ly) |
| SGOT | serum glutamic oxaloacetic transaminase (AST) |
| SGPT | serum glutamic pyruvic transaminase (ALT) |
| SmPC | summary of product characteristics |
| SV | Screening visit |
| TIBC | total iron binding capacity |
| TREAT | Trial to Reduce Cardiovascular Events with Aranesp Therapy |
| TSAT | transferrin saturation |
| uACR | urine albumin-to-creatinine ratio |
| ULN | upper limit of normal |
| US | United States |
| VEGF | vascular endothelial growth factor |
| WBC | white blood cell |
| WHO | World Health Organization |

5.2 Compounds

In certain embodiments, a compound for use with the methods and formulations provided herein is a modulator of a HIF prolyl hydroxylase. In more specific embodiments, a compound for use with the methods provided herein is a modulator of a HIF-1-alpha prolyl hydroxylase. In other, more specific embodiments, a compound for use with the methods provided herein is a modulator of a HIF-2-alpha prolyl hydroxylase. In certain, even more specific embodiments, a compound for use with the methods provided herein is a modulator of a HIF-2-alpha prolyl hydroxylase that is more active against HIF-2-alpha prolyl hydroxylase than HIF-1-alpha prolyl hydroxylase by at least 10%, 20%, 25%, 30%, 40%, 50%, 60%, 70%, 75%, 80%, 90%, 100%, 125%, 150%, 175%, 200%, 250%, 500%, 750%, or at least 1000%. Thus, in certain embodiments, a compound provided herein for use with the methods provided herein preferentially stabilizes HIF-2-alpha over HIF-1-alpha. To determine preferential stabilization of HIF-2-alpha over HIF-1-alpha, the concentrations of HIF-1-alpha and HIF-2-alpha in a subject with and without test compound can be determined using a HIF-1-alpha and a HIF-2-alpha ELISA kit. Care should be taken that the primary antibodies in the respective kits are not cross-reactive with the other HIF (i.e., the primary antibody against HIF-1-alpha reacts immunospecifically with HIF-1-alpha and does not cross-react with HIF-2-alpha; the primary antibody against HIF-2-alpha reacts immunospecifically with HIF-2-alpha and does not cross-react with HIF-1-alpha).

In certain embodiments, a compound of the invention which is a HIF prolyl hydroxylase inhibitor or a HIF-alpha stabilizer is a heterocyclic carboxamide. In certain such embodiments, the heterocyclic carboxamide is selected from a pyridyl carboxamide, a quinoline carboxamide, and an isoquinoline carboxamide.

In certain embodiments, the HIF prolyl hydroxylase inhibitor or HIF-alpha stabilizer has a structure of Formula (I):

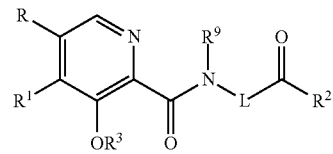

Formula (I)

or a pharmaceutically acceptable salt, solvate or hydrate thereof, wherein
  R and $R^1$ are each independently:
    (i) hydrogen
    (ii) substituted or unsubstituted phenyl; or
    (iii) substituted or unsubstituted heteroaryl;
    said substitution selected from:
      (i) $C_1$-$C_4$ alkyl;
      (ii) $C_3$-$C_4$ cycloalkyl;
      (iii) $C_1$-$C_4$ alkoxy;
      (iv) $C_3$-$C_4$ cycloalkoxy;
      (v) $C_1$-$C_4$ haloalkyl;
      (vi) $C_3$-$C_4$ halocycloalkyl;
      (vii) halogen;
      (viii) cyano;
      (ix) NHC(O)$R^4$;
      (x) C(O)N$R^{5a}R^{5b}$; and
      (xi) heteroaryl; or
      (xii) two substituents are taken together to form a fused ring having from 5 to 7 atoms;
  $R^4$ is a $C_1$-$C_4$ alkyl or $C_3$-$C_4$ cycloalkyl;
  $R^{5a}$ and $R^{5b}$ are each independently selected from:
    (i) hydrogen;
    (ii) $C_1$-$C_4$ alkyl;
    (iii) $C_3$-$C_4$ cycloalkyl; or
    (iv) $R^{5a}$ and $R^{5b}$ are taken together to form a ring having from 3 to 7 atoms;
  $R^2$ is selected from:
    (i) $OR^6$
    (ii) $NR^{7a}R^{7b}$; and
  $R^6$ is selected from hydrogen and $C_1$-$C_4$ alkyl or $C_3$-$C_4$ cycloalkyl;
  $R^{7a}$ and $R^{7b}$ are each independently selected from:
    (i) hydrogen;
    (ii) $C_1$-$C_4$ alkyl or $C_3$-$C_4$ cycloalkyl; or
    (iii) $R^{7a}$ and $R^{7b}$ are taken together to form a ring having from 3 to 7 atoms;
  $R^3$ is selected from hydrogen, methyl, and ethyl;
  L is a linking unit having a structure —[C($R^{8a}R^{8b}$)]$_n$—
  $R^{8a}$ and $R^{8b}$ are each independently selected from hydrogen, methyl and ethyl;
  n is an integer from 1 to 3; and
  $R^9$ is selected from hydrogen and methyl.

In certain, more specific embodiments, in Formula (I) R and $R^1$ are not both hydrogen.

In certain embodiments, the HIF prolyl hydroxylase inhibitor or HIF-alpha stabilizer has a structure of Formula (II):

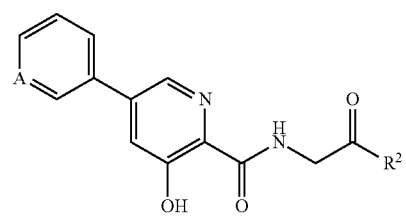

Formula (II)

or a pharmaceutically acceptable salt, solvate or hydrate thereof, wherein

A is selected from the group consisting of CR', N, N⁺—O⁻ and N+(C₁-C₆ alkyl);

R' is selected from the group consisting of H, C₁-C₆ alkyl, C₃-C₆ cycloalkyl, C₂-C₆ alkenyl, C₃-C₆ cycloalkenyl, C₂-C₆ alkynyl, C₄-C₇ heterocycloalkyl, C₆-C₁₀ aryl, C₅-C₁₀ heteroaryl, NH₂, NHR", N(R")₂, NHC(O)R", NR"C(O)R", F, Cl, Br, I, OH, OR", SH, SR", S(O)R", S(O)₂R", S(O)NHR", S(O)₂NHR", S(O)NR"₂, S(O)₂NR"₂, C(O)R", CO₂H, CO₂R", C(O)NH₂, C(O)NHR", C(O)NR"₂, CN, CH₂CN, CF₃, CHF₂, CH₂F, NH(CN), N(CN)₂, CH(CN)₂, C(CN)₃; and R" is independently selected from the group consisting of C₁-C₆ alkyl, C₃-C₆ cycloalkyl, C₄-C₇ heterocycloalkyl, C₆-C₁₀ aryl and C₅-C₁₀ heteroaryl; and wherein C₁-C₆ alkyl, C₃-C₆ cycloalkyl, or C₄-C₇ heterocycloalkyl are optionally substituted with oxo, NH₂, NHR", N(R")₂, F, Cl, Br, I, OH, OR", SH, SR", S(O)R", S(O)₂R", S(O)NHR", S(O)₂NHR", S(O)NR"₂, S(O)₂NR"₂, C(O)R", CO₂H, CO₂R", C(O)NH₂, C(O)NHR", C(O)NR"₂, CN, CH₂CN, CF₃, CHF₂, CH₂F, NH(CN), N(CN)₂, CH(CN)₂, C(CN)₃; and wherein C₆-C₁₀ aryl or C₅-C₁₀ heteroaryl are optionally substituted with C₁-C₆ alkyl, C₃-C₆ cycloalkyl, C₂-C₆ alkenyl, C₃-C₆ cycloalkenyl, C₂-C₆ alkynyl, C₄-C₇ heterocycloalkyl, C₆ aryl, C₅-C₆ heteroaryl, NH₂, NHR", N(R")₂, NHC(O)R", NR"C(O)R", F, Cl, Br, I, OH, OR", SH, SR", S(O)R", S(O)₂R", S(O)NHR", S(O)₂NHR", S(O)NR"₂, S(O)₂NR"₂, C(O)R", CO₂H, CO₂R", C(O)NH₂, C(O)NHR", C(O)NR"₂, CN, CH₂CN, CF₃, CHF₂, CH₂F, NH(CN), N(CN)₂, CH(CN)₂, or C(CN)₃; and wherein two R" groups on a nitrogen can be taken together to form a ring having from 2 to 7 carbon atoms and from 1 to 3 heteroatoms chosen from nitrogen, oxygen and sulfur including the nitrogen atom to which the two R" groups are bonded;

R² is selected from:
(i) OR⁶;
(ii) NR⁷ᵃR⁷ᵇ; and

R⁶ is selected from hydrogen and C₁-C₄ alkyl or C₃-C₄ cycloalkyl;

R⁷ᵃ and R⁷ᵇ are each independently selected from:
(i) hydrogen;
(ii) C₁-C₄ alkyl or C₃-C₄ cycloalkyl; or
(iii) R⁷ᵃ and R⁷ᵇ are taken together to form a ring having from 3 to 7 atoms.

In certain embodiments, the HIF stabilizer is a compound having a structure of Formula (III)

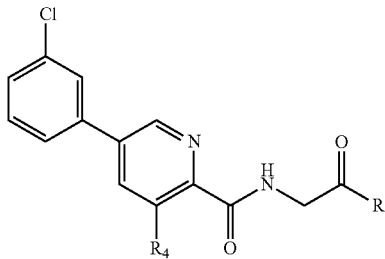

Formula (III)

or a pharmaceutically acceptable salt, solvate or hydrate thereof, wherein

R is chosen from
(i) —OR¹; or
(ii) —NR²R³; or
(iii) —OM¹;

R¹ is:
(i) hydrogen; or
(ii) C₁-C₆ alkyl or C₃-C₆ cycloalkyl;

R² and R³ are each independently selected from:
(i) hydrogen;
(ii) C₁-C₄ alkyl or C₃-C₄ cycloalkyl; or
(iii) R² and R³ can be taken together to form a ring having from 2 to 7 carbon atoms and from 1 to 3 heteroatoms chosen from nitrogen, oxygen and sulfur including the nitrogen atom to which R² and R³ are bonded; and M¹ is a cation; and R⁴ is:
(i) —OH; or
(ii) —OM²; and M² is a cation.

In certain embodiments, the HIF stabilizer is a compound having a structure of Formula (IV)

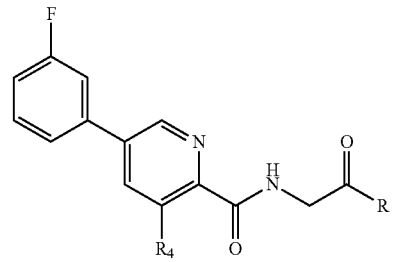

Formula (IV)

or a pharmaceutically acceptable salt, solvate or hydrate thereof, wherein

R is chosen from
(i) —OR¹; or
(ii) —NR²R³; or
(iii) —OM¹;

R¹ is:
(i) hydrogen; or
(ii) C₁-C₆ alkyl or C₃-C₆ cycloalkyl;

R² and R³ are each independently selected from:
(i) hydrogen;
(ii) C₁-C₄ alkyl or C₃-C₄ cycloalkyl; or
(iii) R² and R³ can be taken together to form a ring having from 2 to 7 carbon atoms and from 1 to 3 heteroatoms chosen from nitrogen, oxygen and sulfur including the nitrogen atom to which R² and R³ are bonded; and M¹ is a cation; and R⁴ is:
(i) —OH; or
(ii) —OM²; and M² is a cation.

HIF prolyl hydroxylase inhibitor compounds described herein are unsubstituted or substituted 3-hydroxy-pyridine-2-carboxamides, having the structure shown in Formula (V) below:

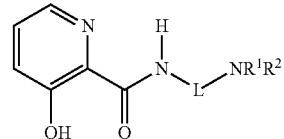

Formula (V)

and pharmaceutically acceptable salts and tautomers thereof, wherein: L is $C_{1-6}$ alkyl; and wherein $R^1$ and $R^2$ are independently H or $C_{1-6}$ alkyl.

In certain embodiments, the HIF prolyl hydroxylase inhibitor or HIF-alpha stabilizer is {[5-(3-chlorophenyl)-3-hydroxypyridine-2-carbonyl]amino}acetic acid (Compound 1):

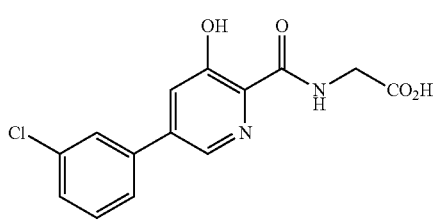

Compound 1 or a pharmaceutically acceptable salt, solvate or hydrate thereof.

In certain embodiments, the HIF stabilizer is Compound 2 having the structure:

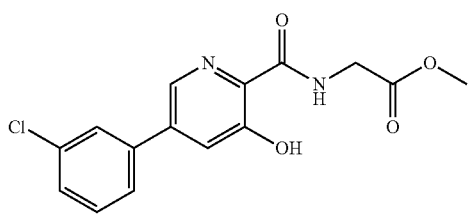

Compound 2 or a pharmaceutically acceptable salt, solvate or hydrate thereof.

In certain embodiments, the HIF stabilizer is Compound 3 having a structure

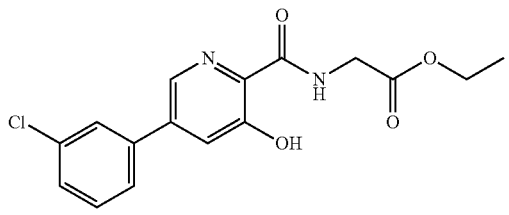

Compound 3 or a pharmaceutically acceptable salt, solvate or hydrate thereof.

In certain embodiments, the HIF stabilizer is Compound 4 having a structure

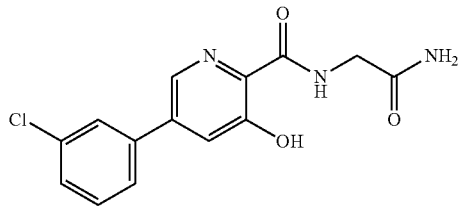

Compound 4 or a pharmaceutically acceptable salt, solvate or hydrate thereof.

In certain embodiments, the HIF stabilizer is Compound 5 having the structure

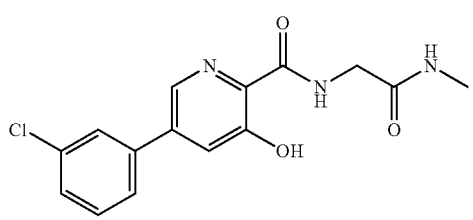

Compound 5 or a pharmaceutically acceptable salt, solvate or hydrate thereof.

In certain embodiments, the HIF stabilizer is Compound 6 having the structure

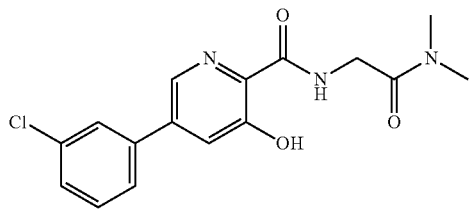

Compound 6 or a pharmaceutically acceptable salt, solvate or hydrate thereof.

In certain embodiments, the HIF prolyl hydroxylase inhibitor or HIF-alpha stabilizer is Compound 7 having the structure:

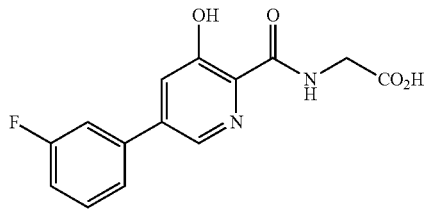 [SMILES: O=C(O)CNC(=O)c1ncc(-c2cccc(F)c2)cc1O]

Compound 7 or a pharmaceutically acceptable salt, solvate or hydrate thereof.

In certain embodiments, the HIF stabilizer is Compound 8 having the structure:

Compound 8

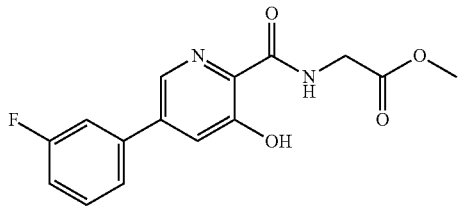

or a pharmaceutically acceptable salt, solvate or hydrate thereof.

In certain embodiments, the HIF stabilizer is Compound 9 having a structure

Compound 9

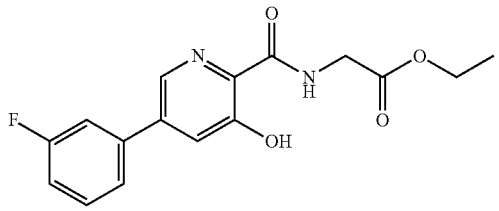

or a pharmaceutically acceptable salt, solvate or hydrate thereof.

In certain embodiments, the HIF stabilizer is Compound 10 having a structure

Compound 10

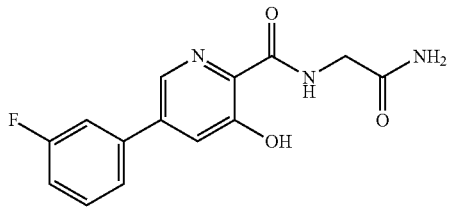

or a pharmaceutically acceptable salt, solvate or hydrate thereof.

In certain embodiments, the HIF stabilizer is Compound 11 having the structure

Compound 11

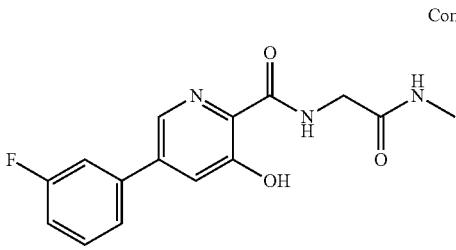

or a pharmaceutically acceptable salt, solvate or hydrate thereof.

In certain embodiments, the HIF stabilizer is Compound 12 having the structure

Compound 12

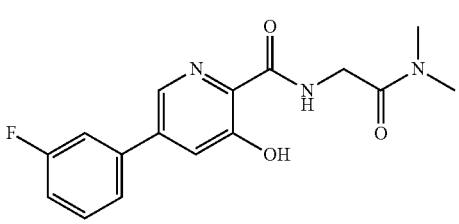

or a pharmaceutically acceptable salt, solvate or hydrate thereof.

In certain embodiments, the HIF stabilizer is Compound 13 having the structure

Compound 13

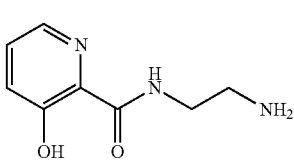

having a name N-(2-aminoethyl)-3-hydroxy-pyridine-2-carboxamide, including pharmaceutically acceptable salts and tautomers thereof. Tautomers of Compound 13 include the following:

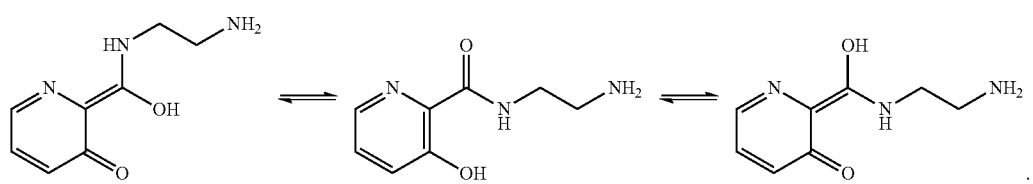 [SMILES: NCCN/C(O)=C1\N=CC=CC1=O ; NCCNC(=O)c1ncccc1O ; NCCN/C(O)=C1/N=CC=CC1=O]

In certain embodiments, a metabolite of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, or Compound 13 can be used with the methods provided herein. In certain more specific embodiments, such a metabolite is a phenolic glucuronide or an acyl-glucuronide.

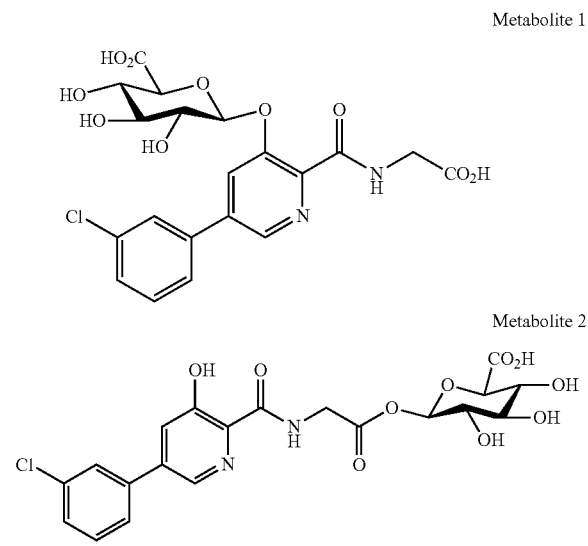

Metabolite 1

Metabolite 2

Compound 13 can be prepared using reagents and methods known in the art, including the methods provided in Chinese Patent Application Publication No. CN 85107182 A, published on Apr. 8, 1987, and German Patent Application Publication No. DE 3530046 A1, published on Mar. 13, 1986, the entire contents of each of which are incorporated herein by reference.

5.3 Formulations 5.3.1 Compound 1 Formulations

In certain embodiments, provided herein are formulations comprising intra-granular components, extra-granular components, and film coating components, wherein the intra-granular components comprise Compound 1, an insoluble diluent or carrier, a disintegrant, and a diluent or filler; wherein the extra-granular components comprise a disintegrant, a glidant, and/or a lubricant; and wherein the film coating components comprise a tablet coating.

In certain embodiments, provided herein are oral dosage formulations that comprise about 10%, about 15%, about 20%, about 25%, about 30%, about 35%, about 40%, about 45%, about 50%, about 55%, about 60%, about 65%, about 70%, about 75%, about 80%, about 85%, or about 90% by weight of Compound 1, wherein the weight is the total weight of all intra-granular and extra-granular components of a tablet.

In certain embodiments, provided herein are oral dosage formulations that comprise about 5%, about 10%, about 15%, about 20%, about 25%, about 30%, about 35%, about 40%, about 45%, or about 50%, by weight of an insoluble diluent or carrier, wherein the weight is the total weight of all intra-granular and extra-granular components of a tablet.

In certain embodiments, provided herein are oral dosage formulations that comprise about 1%, about 1.5%, about 2.0%, about 2.5%, about 3%, about 3.5%, about 4%, about 4.5%, about 5.0%, about 5.5%, about 6.0%, about 6.5%, about 7%, about 7.5%, about 8%, about 8.5%, about 9.0%, about 9.5%, or about 10%, by weight of a disintegrant, wherein the weight is the total weight of all intra-granular and extra-granular components of a tablet.

In certain embodiments, provided herein are oral dosage formulations that comprise about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, or about 0.8%, by weight of a glidant, wherein the weight is the total weight of all intra-granular and extra-granular components of a tablet.

In certain embodiments, provided herein are oral dosage formulations that comprise about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, or about 0.8%, about 0.85%, about 0.9%, about 0.95%, about 1.0%, about 1.05%, about 1.1%, about 1.15%, about 1.2%, about 1.2%, about 1.25%, about 1.3%, about 1.35%, about 1.4%, about 1.45%, or about 1.5%, by weight of a lubricant, wherein the weight is the total weight of all intra-granular and extra-granular components of a tablet.

In certain embodiments, provided herein are formulations comprising intra-granular components, extra-granular components, and film coating components, wherein the intra-granular component comprises about 50% to about 80% by weight of Compound 1, about 10% to about 40% by weight of an insoluble diluent or carrier, about 1.5% to about 4.5% by weight of a disintegrant, and about 1% to about 5% by weight of a diluent or filler; wherein the extra-granular component comprises about 1.5% to about 4.5% by weight of a disintegrant, about 0.1% to about 0.4% by weight of a glidant, and about 0.15% to about 1.35% by weight of a lubricant; and wherein the film coating component comprises about 1.0% to about 8% by weight of a tablet coating; and wherein the weight is the total weight of all intra-granular and extra-granular components.

In certain embodiments, provided herein are formulations comprising intra-granular components, extra-granular components, and film coating components, wherein the intra-granular component comprises about 55% to about 75% by weight of Compound 1, about 15% to about 35% by weight of an insoluble diluent or carrier, about 2.0% to about 4.0% by weight of a disintegrant, and about 1.8% to about 3.8% by weight of a diluent or filler; wherein the extra-granular component comprises about 2.0% to about 4.0% by weight of a disintegrant, about 0.15% to about 0.35% by weight of a glidant, and about 0.35% to about 1.15% by weight of a lubricant; and wherein the film coating component comprises about 1.0% to about 8% by weight of a tablet coating; and wherein the weight is the total weight of all intra-granular and extra-granular components.

In certain embodiments, provided herein are formulations comprising intra-granular components, extra-granular components, and film coating components, wherein the intra-granular component comprises about 60% to about 70% by weight of Compound 1, about 20% to about 30% by weight of an insoluble diluent or carrier, about 2.5% to about 3.5% by weight of a disintegrant, and about 2.3% to about 3.3% by weight of a diluent or filler; wherein the extra-granular component comprises about 2.5% to about 3.5% by weight of a disintegrant, about 0.2% to about 0.3% by weight of a glidant, about 0.55% to about 0.95% by weight of a lubricant; and wherein the film coating component comprises about 1.0% to about 8% by weight of a tablet coating; and wherein the weight is the total weight of all intra-granular and extra-granular components.

In certain embodiments, provided herein are formulations comprising intra-granular components, extra-granular components, and film coating components, wherein the intra-granular component comprises about 65% by weight of Compound 1, about 25% by weight of an insoluble diluent or carrier, about 3% by weight of a disintegrant, and about 2.8% by weight of a diluent or filler; wherein the extra-granular component comprises about 3% by weight of a disintegrant, about 0.25% by weight of a glidant, about 0.75% by weight of a lubricant; and wherein the film coating component comprises about 2.0% to about 6.0% by weight of a tablet coating; and wherein the weight is the total weight of all intra-granular and extra-granular components.

In certain embodiments, provided herein are formulations comprising intra-granular components, extra-granular components, and film coating components, wherein the intra-granular components comprise Compound 1, microcrystalline cellulose, sodium starch glycolate, and hydroxypropyl methylcellulose, wherein the extra-granular components comprise sodium starch glycolate, colloidal silicon dioxide, and magnesium stearate; and wherein the film-coating components comprise Opadry®.

In certain embodiments, provided herein are formulations comprising intra-granular components, extra-granular components, and film coating components, wherein the intra-granular component comprises about 50% to about 80% by weight of Compound 1, about 10% to about 40% by weight of microcrystalline cellulose, about 1.5% to about 4.5% by weight of sodium starch glycolate, and about 1% to about 5% by weight of a hydroxypropyl methylcellulose; wherein the extra-granular component comprises about 1.5% to about 4.5% by weight of a sodium starch glycolate, about 0.1% to about 0.4% by weight of colloidal silicon dioxide, and about 0.15% to about 1.35% by weight of magnesium stearate; wherein the film coating component comprises about 1.0% to about 8% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 55% to about 75% by weight of Compound 1, about 15% to about 35% by weight of microcrystalline cellulose, about 2.0% to about 4.0% by weight of sodium starch glycolate, and about 1.8% to about 3.8% by weight of a hydroxypropyl methylcellulose; wherein the extra-granular component comprises about 2.0% to about 4.0% by weight of a sodium starch glycolate, about 0.15% to about 0.35% by weight of colloidal silicon dioxide, and about 0.35% to about 1.15% by weight of magnesium stearate; wherein the film coating component comprises about 1.0% to about 8% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 60% to about 70% by weight of Compound 1, about 20% to about 30% by weight of microcrystalline cellulose, about 2.5% to about 3.5% by weight of sodium starch glycolate, and about 2.3% to about 3.3% by weight of a hydroxypropyl methylcellulose; wherein the extra-granular component comprises about 2.5% to about 3.5% by weight of a sodium starch glycolate, about 0.2% to about 0.3% by weight of colloidal silicon dioxide, and about 0.55% to about 0.95% by weight of magnesium stearate; wherein the film coating component comprises about 1.0% to about 8% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 60% by weight of Compound 1, about 30% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 65% by weight of Compound 1, about 25% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 70% by weight of Compound 1, about 20% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 75% by weight of Compound 1, about 15% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 80% by weight of Compound 1, about 10% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain other embodiments, provided herein are unit dosage forms that comprise between about 100 mg and about 1,200 mg, about 200 mg and about 1,000 mg, about 400 mg and about 800 mg, or about 450 mg and about 600 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid).

In certain other embodiments, provided herein are unit dosage forms that comprise about 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150, or even about 1,200 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain embodiments, the unit dosage form comprises about 40 mg, about 120 mg, about 150 mg, about 185 mg, about 200 mg, about 250 mg, about 300 mg, or even about 315 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the unit dosage form is a capsule comprising about 40 mg, about 120 mg, about 185 mg, about 200 mg, about 200, about 250 mg, or even about 300 mg of the compound. In certain such embodiments, the unit dosage form is a tablet comprising about 150 mg of the compound. In certain such embodiments, the unit dosage form is a tablet comprising about 315 mg of the compound.

5.3.2 Compound 7 Formulations

In certain embodiments, provided herein are formulations comprising intra-granular components, extra-granular components, and film coating components, wherein the intra-granular components comprise Compound 7, an insoluble diluent or carrier, a disintegrant, and a diluent or filler; wherein the extra-granular components comprise a disintegrant, a glidant, and/or a lubricant; and wherein the film coating components comprise a tablet coating.

In certain embodiments, provided herein are oral dosage formulations that comprise about 10%, about 15%, about 20%, about 25%, about 30%, about 35%, about 40%, about 45%, about 50%, about 55%, about 60%, about 65%, about 70%, about 75%, about 80%, about 85%, or about 90% by weight of Compound 7, wherein the weight is the total weight of all intra-granular and extra-granular components of a tablet.

In certain embodiments, provided herein are oral dosage formulations that comprise about 5%, about 10%, about 15%, about 20%, about 25%, about 30%, about 35%, about 40%, about 45%, or about 50%, by weight of an insoluble diluent or carrier, wherein the weight is the total weight of all intra-granular and extra-granular components of a tablet.

In certain embodiments, provided herein are oral dosage formulations that comprise about 1%, about 1.5%, about 2.0%, about 2.5%, about 3%, about 3.5%, about 4%, about 4.5%, about 5.0%, about 5.5%, about 6.0%, about 6.5%, about 7%, about 7.5%, about 8%, about 8.5%, about 9.0%, about 9.5%, or about 10%, by weight of a disintegrant, wherein the weight is the total weight of all intra-granular and extra-granular components of a tablet.

In certain embodiments, provided herein are oral dosage formulations that comprise about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, or about 0.8%, by weight of a glidant, wherein the weight is the total weight of all intra-granular and extra-granular components of a tablet.

In certain embodiments, provided herein are oral dosage formulations that comprise about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, or about 0.8%, about 0.85%, about 0.9%, about 0.95%, about 1.0%, about 1.05%, about 1.1%, about 1.15%, about 1.2%, about 1.2%, about 1.25%, about 1.3%, about 1.35%, about 1.4%, about 1.45%, or about 1.5%, by weight of a lubricant, wherein the weight is the total weight of all intra-granular and extra-granular components of a tablet.

In certain embodiments, provided herein are formulations comprising intra-granular components, extra-granular components, and film coating components, wherein the intra-granular component comprises about 50% to about 80% by weight of Compound 7, about 10% to about 40% by weight of an insoluble diluent or carrier, about 1.5% to about 4.5% by weight of a disintegrant, and about 1% to about 5% by weight of a diluent or filler; wherein the extra-granular component comprises about 1.5% to about 4.5% by weight of a disintegrant, about 0.1% to about 0.4% by weight of a glidant, and about 0.15% to about 1.35% by weight of a lubricant; and wherein the film coating component comprises about 1.0% to about 8% by weight of a tablet coating; and wherein the weight is the total weight of all intra-granular and extra-granular components.

In certain embodiments, provided herein are formulations comprising intra-granular components, extra-granular components, and film coating components, wherein the intra-granular component comprises about 55% to about 75% by weight of Compound 7, about 15% to about 35% by weight of an insoluble diluent or carrier, about 2.0% to about 4.0% by weight of a disintegrant, and about 1.8% to about 3.8% by weight of a diluent or filler; wherein the extra-granular component comprises about 2.0% to about 4.0% by weight of a disintegrant, about 0.15% to about 0.35% by weight of a glidant, and about 0.35% to about 1.15% by weight of a lubricant; and wherein the film coating component comprises about 1.0% to about 8% by weight of a tablet coating; and wherein the weight is the total weight of all intra-granular and extra-granular components.

In certain embodiments, provided herein are formulations comprising intra-granular components, extra-granular components, and film coating components, wherein the intra-granular component comprises about 60% to about 70% by weight of Compound 7, about 20% to about 30% by weight of an insoluble diluent or carrier, about 2.5% to about 3.5% by weight of a disintegrant, and about 2.3% to about 3.3% by weight of a diluent or filler; wherein the extra-granular component comprises about 2.5% to about 3.5% by weight of a disintegrant, about 0.2% to about 0.3% by weight of a glidant, about 0.55% to about 0.95% by weight of a lubricant; and wherein the film coating component comprises about 1.0% to about 8% by weight of a tablet coating; and wherein the weight is the total weight of all intra-granular and extra-granular components.

In certain embodiments, provided herein are formulations comprising intra-granular components, extra-granular components, and film coating components, wherein the intra-granular component comprises about 65% by weight of Compound 7, about 25% by weight of an insoluble diluent or carrier, about 3% by weight of a disintegrant, and about 2.8% by weight of a diluent or filler; wherein the extra-granular component comprises about 3% by weight of a disintegrant, about 0.25% by weight of a glidant, about 0.75% by weight of a lubricant; and wherein the film coating component comprises about 2.0% to about 6.0% by weight of a tablet coating; and wherein the weight is the total weight of all intra-granular and extra-granular components.

In certain embodiments, provided herein are formulations comprising intra-granular components, extra-granular components, and film coating components, wherein the intra-granular components comprise Compound 7, microcrystalline cellulose, sodium starch glycolate, and hydroxypropyl methylcellulose, wherein the extra-granular components comprise sodium starch glycolate, colloidal silicon dioxide, and magnesium stearate; and wherein the film-coating components comprise Opadry®.

In certain embodiments, provided herein are formulations comprising intra-granular components, extra-granular components, and film coating components, wherein the intra-granular component comprises about 50% to about 80% by weight of Compound 7, about 10% to about 40% by weight of microcrystalline cellulose, about 1.5% to about 4.5% by weight of sodium starch glycolate, and about 1% to about 5% by weight of a hydroxypropyl methylcellulose; wherein the extra-granular component comprises about 1.5% to about 4.5% by weight of a sodium starch glycolate, about 0.1% to about 0.4% by weight of colloidal silicon dioxide, and about 0.15% to about 1.35% by weight of magnesium stearate; wherein the film coating component comprises about 1.0% to about 8% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 55% to about 75% by weight of Compound 7, about 15% to about 35% by weight of microcrystalline cellulose, about 2.0% to about 4.0% by weight of sodium starch glycolate, and about 1.8% to about 3.8% by weight of a hydroxypropyl methylcellulose; wherein the extra-granular component comprises about 2.0% to about 4.0% by weight of a sodium starch glycolate, about 0.15% to about 0.35% by weight of colloidal silicon dioxide, and about 0.35% to about 1.15% by weight of magnesium stearate; wherein the film coating component comprises about 1.0% to about 8% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 60% to about 70% by weight of Compound 7, about 20% to about 30% by weight of microcrystalline cellulose, about 2.5% to about 3.5% by weight of sodium starch glycolate, and about 2.3% to about 3.3% by weight of a hydroxypropyl methylcellulose; wherein the extra-granular component comprises about 2.5% to about 3.5% by weight of a sodium starch glycolate, about 0.2% to about 0.3% by weight of colloidal silicon dioxide, and about 0.55% to about 0.95% by weight of magnesium stearate; wherein the film coating component comprises about 1.0% to about 8% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 60% by weight of Compound 7, about 30% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 65% by weight of Compound 7, about 25% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 70% by weight of Compound 7, about 20% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 75% by weight of Compound 7, about 15% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations comprising intra-granular components, extra-granular components, and film coating components, wherein the intra-granular component comprises about 80% by weight of Compound 7, about 10% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain other embodiments, provided herein are unit dosage forms that comprise between about 25 mg and about 2000 mg, about 50 mg and about 1500 mg, about 100 mg and about 1,200 mg, about 200 mg and about 1,000 mg, about 400 mg and about 800 mg, or about 450 mg and about 600 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-fluorophenyl)-3-hydroxypyridine-2-carbonyl]amino}acetic acid.

In certain other embodiments, provided herein are unit dosage forms that comprise about 10 mg, 15 mg, 20 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150, or even about 1,200 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-fluorophenyl)-3-hydroxypyridine-2-carbonyl]amino}acetic acid. In certain embodiments, the unit dosage form comprises about 25 mg, about 40 mg, about 120 mg, about 150 mg, about 185 mg, about 200 mg, about 250 mg, about 300 mg, or even about 315 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-fluorophenyl)-3-hydroxypyridine-2-carbonyl]amino}acetic acid). In certain such embodiments, the unit dosage form is a capsule comprising about 25 mg, about 40 mg, about 120 mg, about 185 mg, about 200 mg, about 200, about 250 mg, or even about 300 mg of the compound. In certain such embodiments, the unit dosage form is a tablet comprising about 150 mg of the compound. In certain such embodiments, the unit dosage form is a tablet comprising about 315 mg of the compound. In certain such embodiments, the unit dosage form is a tablet comprising about 25 mg of the compound. In certain such embodiments, the unit dosage form is a free acid in form of a pharmaceutically acceptable emulsion, microemulsion, solution, suspension, syrup, or elixir, comprising about 25 mg, about 40 mg, about 120 mg, about 185 mg, about 200 mg, about 200, about 250 mg, or even about 300 mg of the compound. In certain such embodiments, the unit dosage form is a free acid in form of a pharmaceutically acceptable emulsion, microemulsion, solution, suspension, syrup, or elixir, comprising about 150 mg of the compound. In certain such embodiments, the unit dosage form is a free acid in form of a pharmaceutically acceptable emulsion, microemulsion, solution, suspension, syrup, or elixir, comprising about 315 mg of the compound. In certain such embodiments, the unit dosage form is a free acid in form of a pharmaceutically acceptable emulsion, microemulsion, solution, suspension, syrup, or elixir, comprising about 25 mg of the compound.

5.3.3 Pharmaceutical Compositions

Pharmaceutical compositions may be used in the preparation of individual, single unit dosage forms. Pharmaceutical compositions and dosage forms provided herein comprise a compound as provided herein, or a pharmaceutically acceptable salt, solvate, or hydrate thereof (e.g., the parent compound). Pharmaceutical compositions and dosage forms can further comprise one or more excipients.

In certain embodiments, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25 NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's The Science and Practice of Pharmacy, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, insoluble diluents, binders, fillers, disintegrants, glidants, carriers, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methylcellulose, (e.g., Nos. 2208, 2906, 2910), microcrystalline cellulose, and mixtures thereof.

Examples of insoluble diluents and carriers suitable for use in the pharmaceutical compositions and dosage forms provided herein include, but are not limited to, dibasic calcium phosphate and microcrystalline cellulose. Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of diluents/fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, hydroxypropyl methylcellulose (e.g., Methocel E5 Premium LV) and mixtures thereof.

In certain embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof.

In certain embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate (e.g., Explotab®), potato or tapioca starch, other starches, pregelatinized starch, other starches, clays, other algins, other celluloses, gums, and mixtures thereof.

Glidants that can be used in pharmaceutical compositions and dosage forms include, but are not limited to fumed silica, magnesium carbonate, magnesium stearate, colloidal silicon dioxide (e.g., Aerosil, Cab-O-Sil), starch and talc.

Lubricants that can be used in pharmaceutical compositions and dosage forms include, but are not limited to, calcium stearate, magnesium stearate (e.g. Hyqual® 5712), mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic colloidal silicon dioxide product sold by Cabot Co. of Boston, Mass.), and mixtures thereof.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

5.4 Patient Populations

In certain embodiments, provided herein are methods for treating and/or preventing a anemia secondary to non-dialysis dependent chronic kidney disease, comprising administering a sufficient number of successive doses of a HIF prolyl hydroxylase inhibitor or a HIF-alpha stabilizer to a patient having anemia secondary to non-dialysis dependent chronic kidney disease wherein the patient has at least 2, 3, 4, 5 or all of (i) an estimated glomerular filtration rate (eGFR) of less than 60 mL/min/1.73 m$^2$, wherein the subject is not on dialysis and not expected to start dialysis within 3 months of beginning of treatment, (ii) a hemoglobin level of less than 10.0 g/dL prior to commencement of treatment, (iii) a ferritin level equal to or above 100 ng/mL within 4 weeks of commencement of treatment, (iv) a transferrin saturation (TSAT) level equal to or above 20% within 4 weeks commencement of treatment, (v) a folate measurement equal to or above the lower limit of normal within 4 weeks commencement of treatment, (vi) a vitamin B12 measurement equal to or above the lower limit of normal within 4 weeks commencement of treatment, and (vii) an age of at least 18 years.

In certain embodiments, provided herein are methods for treating and/or preventing a anemia secondary to non-dialysis dependent chronic kidney disease, comprising administering a sufficient number of successive doses of a HIF prolyl hydroxylase inhibitor or a HIF-alpha stabilizer to a patient having anemia secondary to non-dialysis dependent chronic kidney disease wherein the patient has at least 2, 3, 4, 5 or all of (i) an estimated glomerular filtration rate (eGFR) of less than 65 mL/min/1.73 m$^2$, wherein the subject is not on dialysis and not expected to start dialysis within 3 months of beginning of treatment, (ii) a hemoglobin level of less than 10.0 g/dL prior to commencement of treatment, (iii) a ferritin level equal to or above 50 ng/mL within 4 weeks of commencement of treatment, (iv) a transferrin saturation (TSAT) level equal to or above 15% within 4 weeks commencement of treatment, (v) a folate measurement equal to or above the lower limit of normal within 4 weeks commencement of treatment, (vi) a vitamin B12 measurement equal to or above the lower limit of normal within 4 weeks commencement of treatment, and (vii) an age of at least 18 years.

In certain embodiments, provided herein are methods for treating and/or preventing a anemia secondary to non-dialysis dependent chronic kidney disease, comprising administering a sufficient number of successive doses of a HIF prolyl hydroxylase inhibitor or a HIF-alpha stabilizer to a patient having anemia secondary to non-dialysis dependent chronic kidney disease wherein the patient is/has none of the following: (i) female who is pregnant or breast-feeding, or who is unable or unwilling to use an acceptable method of contraception, (ii) non-vasectomized male who is unable or unwilling to use an acceptable method of contraception, (iii) anemia due to a cause other than CKD; e.g., sickle cell disease, myelodysplastic syndromes, bone marrow fibrosis, hematologic malignancy, myeloma, hemolytic anemia, thalassemia, pure red cell aplasia, active bleeding, or recent blood loss, (iv) red blood cell transfusion within 4-8 weeks prior to commencement of any treatment, (v) intravenous iron within 4-8 weeks prior to commencement of treatment, (vi) any erythropoeisis-stimulating agent (e.g., rHuEPO; Procrit®, Eprex®, Neorecormon®, Epogen®, Aranesp™ [darbepoetin alfa]) within 8-12 weeks prior to commencement of any treatment, (vii) currently receiving intravenous antibiotic therapy for an acute infection, (viii) major surgery within 8-12 weeks prior to commencement of any treatment (excluding vascular access surgery), (ix) evidence of liver dysfunction (AST or ALT >3.0×ULN, or total bilirubin >2.0×ULN) at 4 weeks prior to commencement of any treatment, (x) uncontrolled hypertension (diastolic blood pressure >110 mmHg or systolic blood pressure >180 mmHg) at 4 weeks prior to commencement of any treatment, (xi) New York Heart Association Class IV congestive heart failure, (xii) Myocardial infarction, acute coronary syndrome, hospitalization for congestive heart failure, or stroke within 8-12 weeks prior to commencement of any treatment, (xiii) history of active malignancy in the previous 2 years prior to screening, except for curatively resected basal cell carcinoma of skin, squamous cell carcinoma of skin, cervical carcinoma in situ, or resected benign colonic polyps, (xiv) history of recent deep vein thrombosis (DVT) or pulmonary embolism within previous 12 weeks prior to screening requiring active treatment, (xv) history of hemosiderosis or hemochromatosis, (xvi) history of prior organ transplantation or scheduled organ transplant (kidney transplant wait-list are not excluded), or stem cell or bone marrow transplantation (corneal transplants are not excluded), (xvii) use of an investigational medication or participation in an investigational study within 30 days or 5 half-lives of the investigational medication (whichever is longer), prior to the 4 weeks prior to commencement of any treatment, (xviii) receipt of the compound in another study or previous participation in a study with another hypoxia-inducible factor prolyl-hydroxylase inhibitor (HIF-PHI), or (xix) any other reason, which in the opinion of the treating physician, would make the patient not suitable for treatment In certain embodiments, provided herein are methods for treating and/or preventing a anemia secondary to non-dialysis dependent chronic kidney disease, comprising administering a sufficient number of successive doses of a HIF prolyl hydroxylase inhibitor or a HIF-alpha stabilizer to a patient having anemia secondary to non-dialysis dependent chronic kidney disease wherein the patient is/has none of the following: (i) female who is pregnant or breast-feeding or woman of child-bearing potential who is unable or unwilling to use an acceptable method of contraception, (ii) non-vasectomized male who is unable or unwilling to use an acceptable method of contraception, (iii) a BMI >50.0 kg/m$^2$, (iv) anemia due to a cause other than Chronic Kidney Disease such as hemolysis (hemolytic anemia), active bleeding, or recent blood loss, (v) history of myelodysplastic syndrome or bone marrow fibrosis, (vi) red blood cell transfusion within 8 weeks prior to commencement of treatment, (vii) Intravenous iron within 4 weeks prior to commencement of treatment, (viii) any erythropoeisis-stimulating agent (such as rHuEPO; ProcritR, Eprex, Neorecormon, Epogen, Darbepoetin (aranesp)), within 10 weeks prior to commencement of treatment, (ix) evidence of active infection, unless the treating physician deems the subject is appropriate for treatment, (x) history of known chronic liver disease or evidence of liver dysfunction (AST or ALT >3.0×ULN, or total bilirubin >2.0×ULN) at 4 weeks prior commencement of treatment, (xi) uncontrolled hypertension (diastolic blood pressure >110 mmHg or systolic blood pressure >180 mmHg) at 4 weeks prior commencement of treatment, (xii) New York Heart Association Class IV congestive heart failure at 4 weeks prior commencement of treatment, (xiii) myocardial infarction, acute coronary syndrome, or stroke within 12 weeks prior to commencement of treatment, (xiv) any history of active malignancy or treatment of malignancy in the previous 2 years prior to commencement of treatment except for curatively resected basal cell carcinoma of skin, squamous cell carcinoma of skin, cervical carcinoma in situ, or resected benign colonic polyps, (xv) history of recent deep vein thrombosis (DVT) or pulmonary embolism within previous 12 weeks prior commencement of treatment requiring active treatment, (xvi) history of hemosiderosis, (xvii) history of prior organ transplantation or scheduled organ transplant (kidney transplant wait-list are not excluded), or stem cell or bone marrow transplantation (corneal transplants are not excluded), (xviii) use of an investigational medication or participation in an investigational study within 45 days or five half-lives of the investigational medication, whichever is longer, preceding the commencement of treatment, (xix) previous participation in this study or previous receipt of 5-(3-chlorophenyl)-3-hydroxypyridine-2-carbonyl]amino}acetic acid in another clinical study or previous receipt of another hypoxia-inducible factor prolyl-hydroxylase inhibitor (HIF-PHI), and (xx) other severe acute or chronic medical or psychiatric condition or laboratory abnormality that may increase the risk associated with treatment and, in the physician's judgment, would make the patient inappropriate for treatment.

In certain embodiments, provided herein are methods for treating anemia, such as anemia secondary to chronic kidney disease (CKD), comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to formulations and the dose and/or dosing regimen described herein in Section 5.3 and Section 5.7, wherein, the patient is at least 18 years old, at least 50 years old, at least 60 years old, at least 65 years old, at least 70 years old, or even at least 80 years old. In certain embodiments, the patient is a geriatric patient. In certain embodiments, the patient is less than 18 years old. In certain embodiments, the patient is a pediatric patient. In certain embodiment, the patient is at least 18 years old. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to chronic kidney disease (CKD), comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein, the patient is a member of a subpopulation selected from White, Hispanic, Black, and Asian. In certain embodiments, the patient is a member of a subpopulation selected from male and female. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to chronic kidney disease (CKD), comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein, the patient has an additional disease or condition selected from cancer, AIDS, congestive heart failure, left ventricular hypertrophy, diabetes, hypertension, dyslipidemia, chronic heart failure, stroke, fatigue, depression, and cognitive impairment, or any combination thereof. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl] amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient is refractory to treatment with an Erythropoiesis-stimulating agent ("ESA"), such as an erythropoietin mimetic. In certain embodiments the ESA is an rhEPO product, including, but not limited to, epoetin alfa, epoetin beta, darbepoetin, or peginesatide. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has a glomerular filtration rate of less than 85, less than 80, less than 75, less than 70, less than 65, less than 60, less than 55, or less than 50 mL/min/1.73 m$^2$. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has hemoglobin level of less than 15%, less than 10%, or even at least 5%. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has folate levels of equal to or above the lower limit of normal. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has vitamin B12 levels of equal to or above the lower limit of normal. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has a transferrin saturation (TSAT) of at least 15%, at least 18% or even at least 20%. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has a ferritin level of at least 50 ng/mL or even at least 100 ng/mL. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has a ferritin level of at least 50 ng/mL with transferrin saturation of at least 18%, or a ferritin level of at least 100 ng/mL with a transferrin saturation of at least 15%. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has a body mass index (BMI) of less than 42 kg/m$^2$ or less than 44 kg/m$^2$, or less than 50 kg/m$^2$. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating anemia, such as anemia secondary to CKD, comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7, wherein the patient has had a red blood cell transfusion within 11 weeks or 12 weeks of initiation of treatment with the compound. In certain alternative embodiments, the patient has not had a red blood cell transfusion within 11 weeks or 12 weeks of initiation of treatment with the compound. In certain such embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl] amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating non-severe anemia secondary to chronic kidney disease, non-severe anemia secondary to congestive heart failure, and idiopathic anemia of aging, comprising administering to a patient having anemia daily dose a compound disclosed herein, such as Compound 1, wherein the compound is administered continuously and/or indefinitely.

In certain embodiments, provided herein are methods for treating and/or preventing iron overload in a patient, said method comprising administering to the patient an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid). In certain embodiments, said administering step is performed according to the formulations and dose and/or dosing regimen described herein in Section 5.3 and Section 5.7.

5.5 Method of Treatment and Prevention

In certain embodiments, provided herein is a method for treating and/or preventing anemia in a subject as described in Section 5.4, such as anemia secondary to non-dialysis dependent chronic kidney disease, comprising administering to a patient having anemia an effective amount of a HIF prolyl hydroxylase inhibitor or a HIF-alpha stabilizer, such as a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2, or a pharmaceutically acceptable salt, solvate, or hydrate thereof, wherein a daily dose comprises about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 600 mg, or about 750 mg of the compound, pharmaceutically acceptable salt, solvate, or hydrate thereof. In certain such embodiments, the daily dose is about 150 mg, about 300 mg, about 450 mg, or about 600 mg. Specifically, such methods comprise administering to a patient a formulation as described in Section 5.3. Such daily doses may be administered orally, once daily, twice daily, or three times daily, preferably once daily. In certain embodiments, the daily dose is 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, or 4 mg/kg.

In certain embodiments, provided herein is a HIF prolyl hydroxylase inhibitor or a HIF-alpha stabilizer, such as a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2, or a pharmaceutically acceptable salt, solvate, or hydrate thereof, for use in a method of treating anemia, such as anemia secondary to chronic kidney disease, comprising administering the HIF prolyl hydroxylase inhibitor of HIF-alpha stabilizer at a daily dose of about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 600 mg, or about 750 mg of the compound, pharmaceutically acceptable salt, solvate, or hydrate thereof. In certain such embodiments, the daily dose is about 150 mg, about 300 mg, about 450 mg, or about 600 mg. Such daily doses may be administered orally, once daily, twice daily, or three times daily, preferably once daily. In certain embodiments, the daily dose is 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, or 4 mg/kg. In certain embodiments, the compound is {[5-(3-chlorophenyl)-3-hydroxypyridine-2-carbonyl]amino}acetic acid. In certain embodiments, the compound is a pharmaceutically acceptable salt of {[5-(3-chlorophenyl)-3-hydroxypyridine-2-carbonyl]amino}acetic acid. In certain embodiments, the compound is a solvate of {[5-(3-chlorophenyl)-3-hydroxypyridine-2-carbonyl]amino}acetic acid. In certain embodiments, the compound is a hydrate of {[5-(3-chlorophenyl)-3-hydroxypyridine-2-carbonyl]amino}acetic acid. In certain embodiments, the compound is 2-(5-(3-fluorophenyl)-3-hydroxypicolinamido)acetic acid. In certain embodiments, the compound is a pharmaceutically acceptable salt of 2-(5-(3-fluorophenyl)-3-hydroxypicolinamido)acetic acid. In certain embodiments, the compound is a solvate of 2-(5-(3-fluorophenyl)-3-hydroxypicolinamido)acetic acid. In certain embodiments, the compound is a hydrate of 2-(5-(3-fluorophenyl)-3-hydroxypicolinamido)acetic acid. In certain embodiments, the compound is administered in a formulation as described in Section 5.3.

In certain such embodiments, the daily dose comprises about 150 mg, about 300 mg, about 450 mg, or about 600 mg of the compound, pharmaceutically acceptable salt, solvate, or hydrate thereof. In certain embodiments, the daily dose comprises about 150 mg. In certain embodiments, the daily dose comprises about 300 mg. In certain embodiments, the daily dose comprises about 450 mg. In certain embodiments, the daily dose comprises about 600 mg.

In certain embodiments, the chronic kidney disease is stage 3, 4, or 5 chronic kidney disease. In certain such embodiments, the chronic kidney disease is pre-dialysis chronic kidney disease. In certain such embodiments, the chronic kidney disease is non-dialysis dependent chronic kidney disease. In certain embodiments, the patient has not been previously treated for anemia, such as anemia secondary to chronic kidney disease. In certain alternative embodiments, the patient has been previously treated for anemia, such as anemia secondary to chronic kidney disease. In certain embodiments, the patient is refractory to treatment with recombinant erythropoietin.

In certain embodiments, the daily dose is administered continuously. In certain embodiments, the daily dose is administered indefinitely, such as for more than 42 consecutive days, or even more than 90 consecutive days. In certain alternative embodiments, the daily dose is administered for at least one week and up to 30 consecutive days, up to 35 consecutive days, or even up to 40 consecutive days. In certain embodiments, the daily dose is administered orally, once daily. In certain embodiments, the daily dose is administered orally as a divided dose administered twice daily. In certain embodiments, the daily dose is administered at a specific time of day. In even more specific embodiments, the daily dose is administered in the early afternoon. In a specific embodiment, the patient has chronic kidney disease and the compound (see Section 5.2) is administered at the same time of day, specifically in the late morning, early afternoon, more specifically just before lunch, just after lunch, between lunch and 2 pm, between 10 am and 2 pm, at 10 am, 11 am, at 12 pm, at 1 pm, or at 2 pm. In certain embodiments, the dose is administered in a formulation as described in Section 5.3

In certain embodiments the daily dose is administered twice per week, three times per week, four times per week, five times per week, six times per week, every day, once every two weeks, once every three weeks, once every four weeks, or once every two months, or once every three months. In certain such embodiments, the dose is administered in a formulation as described in Section 5.3.

In certain embodiments, the hemoglobin levels of the patient are maintained at a level of 8.0 g/dL and at or below about 13.0 g/dL, at least about 8.5 g/dL and at or below 13.0 g/dL, at least about 9.0 g/dL and at or below 13.0 g/dL, at least about 9.5 g/dL and at or below 13.0 g/dL, or at least about 10.0 g/dL and at or below about 13.0 g/dL. In certain such embodiments, hemoglobin levels are maintained at a level of at least about 11.0 g/dL and at or below about 13.0 g/dL. In certain such embodiments, hemoglobin levels are maintained at a level of at least about 11.0 g/dL and at or below about 12.0 g/dL. In certain embodiments, these values are adjusted for altitude, gender, and age of the patient.

In certain embodiments, administration of a compound provided herein in a formulation as described in Section 5.3 results in an increase of the level of hemoglobin increases by at least about 0.1 g/dL, by at least about 0.2 g/dL, by at least about 0.3 g/dL, by at least about 0.4 g/dL, by at least about 0.5 g/dL, by at least about 0.6 g/dL, by at least about 0.7 g/dL, by at least about 0.8 g/dL, by at least about 0.9 g/dL, by at least about 1.0 g/dL, by at least about 1.1 g/dL, by at least about 1.2 g/dL, by at least about 1.3 g/dL, by at least about 1.4 g/dL, or by at least about 1.5 g/dL relative to a baseline hemoglobin level.

In certain embodiments, the compound is optionally administered in combination with another medicament. In certain such embodiments, the other medicament is an iron supplement, such as ferrous sulfate, ferrous gluconate, or ferrous fumarate, which may be administered at least two hours following administration of the compound. In certain embodiments, the iron supplement is administered in an amount such that ferritin is maintained at a level of between about 50 ng/mL and about 300 ng/mL. In certain embodiments, the iron supplement is administered orally at a daily dose about 50 mg of elemental iron. In certain embodiments, the iron supplement is administered on an as needed basis, whereas in certain alternative embodiments, the iron supplement is administered continuously and/or indefinitely. In certain embodiments, the compound is administered in a formulation as described in Section 5.3.

In certain embodiments, the other medicament is an erythropoiesis stimulating agent (ESA), such as an erythropoietin mimetic. In certain embodiments, the other medicament is an rhEPO product, such as epoetin alfa, epoetin beta, darbepoetin, or peginesatide. In certain embodiments, the ESA is administered as a rescue therapy, whereas in certain alternative embodiments, the ESA is administered continuously and/or indefinitely. In certain embodiments, the compound is administered in a formulation as described in Section 5.3.

In certain such embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof is adjusted during the course of treatment. Specifically, the treatment is monitored using routine tests such as for example blood pressure, hematocrit, hemoglobin levels, and/or red blood cell count. Depending on the result of these tests, the daily dose is adjusted, i.e., increased or decreased. In more specific embodiments, the treatment is started using a daily dose of about 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, or at a daily dose of about 450 mg of the compound, pharmaceutically acceptable salt, solvate, or hydrate thereof. In certain embodiments, the daily dose is increased subsequently by about 50 mg, 100 mg, 150 mg, or 200 mg. In certain embodiments, the daily dose is decreased subsequently by about 50 mg, 100 mg, 150 mg, or 200 mg. In certain embodiments, the compound is Compound 1 or a pharmaceutically acceptable salt, solvate, or hydrate thereof. In certain embodiments, the compound is Compound 7 or a pharmaceutically acceptable salt, solvate, or hydrate thereof. In certain embodiments, the compound is administered in a formulation as described in Section 5.3. In certain embodiments, the dose is adjusted as described in the Section 5.7.

In certain embodiments, provided herein are methods of treating anemia in a subject as described in Section 5.4 with a formulation as described in Section 5.3, such as anemia secondary to non-dialysis dependent chronic kidney disease, comprising administering to a patient having anemia a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof; measuring the hemoglobin level in the patient after an administration of the daily dose of the compound and then again a period of time later, wherein when the hemoglobin level in the patient is less than about 10.0 g/dL and the level of hemoglobin has decreased by less than about 0.5 g/dL as compared to the level measured the period of time earlier; or when the hemoglobin level in the patient is less than about 10.0 g/dL and the level of hemoglobin has changed by up to about 0.4 g/dL as compared to the level measured the period of time earlier; or when the hemoglobin level in the patient is between about 10.0 and about 10.9 g/dL and the level of hemoglobin has decreased by less than about 0.5 g/dL as compared to the level measured the period of time earlier; administering an adjusted daily dose of the compound that is 150 mg greater than the daily dose. In certain embodiments, the period of time is from about one week to about eight weeks, such as from about two weeks to about seven weeks, about three weeks to about six weeks, or about four weeks. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof.

In certain embodiments, provided herein are methods of treating anemia in a subject as described in Section 5.4, such as anemia secondary to non-dialysis dependent chronic kidney disease, comprising administering to a patient having anemia a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof; measuring the hemoglobin level in the patient after an administration of the daily dose of the compound and then again a period of time later, wherein when the hemoglobin level in the patient is less than about 10.0 g/dL and the level of hemoglobin has increased by greater than about 1.5 g/dL as compared to the level measured the period of time earlier; or when the hemoglobin level in the patient is between about 10.0 and about 10.9 g/dL and the level of hemoglobin has increased by greater than about 1.5 g/dL as compared to the level measured the period of time earlier; or when the hemoglobin level is between about 11.0 and about 12.2 g/dL and the level of hemoglobin has increased by between about 1.0 and about 1.4 g/dL as compared to the level measured the period of time earlier; or when the hemoglobin level is between about 12.3 and about 12.9 g/dL and the level of hemoglobin has decreased by up to about 0.4 g/dL or increased by up to about 0.4 g/dL as compared to the level measured the period of time earlier; or when the hemoglobin level in the patient is between about 12.3 and about 12.9 g/dL and the level of hemoglobin has increased by about 0.5 to about 0.9 g/dL as compared to the level measured the period of time earlier; administering an adjusted daily dose of the compound that is 150 mg less than the daily dose. In certain embodiments, the daily dose of the compound is about 450 mg. In certain embodiments, the compound is {[5-(3-chlorophenyl)-3-hydroxypyridine-2-carbonyl]amino}acetic acid. In certain embodiments, the compound is a pharmaceutically acceptable salt of {[5-(3-chlorophenyl)-3-hydroxypyridine-2-carbonyl]amino}acetic acid. In certain embodiments, the compound is a solvate of {[5-(3-chlorophenyl)-3-hydroxypyridine-2-carbonyl]amino}acetic acid. In certain embodiments, the compound is a hydrate of {[5-(3-chlorophenyl)-3-hydroxypyridine-2-carbonyl]amino}acetic acid. In certain embodiments, the compound is 2-(5-(3-fluorophenyl)-3-hydroxypicolinamido)acetic acid. In certain embodiments, the compound is a pharmaceutically acceptable salt of 2-(5-(3-fluorophenyl)-3-hydroxypicolinamido)acetic acid. In certain embodiments, the compound is a solvate of 2-(5-(3-fluorophenyl)-3-hydroxypicolinamido)acetic acid. In certain embodiments, the compound is a hydrate of 2-(5-(3-fluorophenyl)-3-hydroxypicolinamido)acetic acid. In certain embodiments, the compound is administered in a formulation as described in Section 5.3. In certain embodiments, the period of time is from about one week to about eight weeks, such as from about two weeks to about seven weeks, about three weeks to about six weeks, or about four weeks.

In certain embodiments, provided herein are methods of treating anemia in a subject as described in Section 5.4, such as anemia secondary to non-dialysis dependent chronic kidney disease, comprising administering to a patient having anemia a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof; measuring the hemoglobin level in the patient after an administration of the daily dose of the compound and then again a period of time later, wherein when the hemoglobin level in the patient is between about 11.0 and about 12.2 g/dL and the level of hemoglobin has increased by greater than about 1.5 g/dL as compared to the level measured the period of time earlier; or when the hemoglobin level in the patient is between about 12.3 and about 12.9 g/dL and the level of hemoglobin has increased by between about 1.0 and about 1.4 g/dL as compared to the level measured the period of time earlier; or when the hemoglobin level in the patient is between about 12.3 and about 12.9 g/dL and the level of hemoglobin has increased by greater than about 1.5 g/dL as compared to the level measured the period of time earlier; or administering an adjusted daily dose of the compound that is 300 mg less than the daily dose. In certain embodiments, the daily dose of the compound is about 450 mg. In certain embodiments, the compound is {[5-(3-chlorophenyl)-3-hydroxypyridine-2-carbonyl]amino}acetic acid. In certain embodiments, the compound is a pharmaceutically acceptable salt of {[5-(3-chlorophenyl)-3-hydroxypyridine-2-carbonyl]amino}acetic acid. In certain embodiments, the compound is a solvate of {[5-(3-chlorophenyl)-3-hydroxypyridine-2-carbonyl]amino}acetic acid. In certain embodiments, the compound is a hydrate of {[5-(3-chlorophenyl)-3-hydroxypyridine-2-carbonyl]amino}acetic acid. In certain embodiments, the daily dose of the compound is about 450 mg. In certain embodiments, the compound is 2-(5-(3-fluorophenyl)-3-hydroxypicolinamido)acetic acid. In certain embodiments, the compound is a pharmaceutically acceptable salt of 2-(5-(3-fluorophenyl)-3-hydroxypicolinamido)acetic acid. In certain embodiments, the compound is a solvate of 2-(5-(3-fluorophenyl)-3-hydroxypicolinamido)acetic acid. In certain embodiments, the compound is administered in a formulation as described in Section 5.3. In certain embodiments, the compound is a hydrate of 2-(5-(3-fluorophenyl)-3-hydroxypicolinamido)acetic acid. In certain embodiments, the period of time is from about one week to about eight weeks, such as from about two weeks to about seven weeks, about three weeks to about six weeks, or about four weeks.

In certain embodiments, the invention relates to a method for treating anemia in a subject as described in Section 5.4, such as anemia secondary to non-dialysis dependent chronic kidney disease, comprising administering to a patient having anemia a daily dose of a compound which is {[5-(3-chlorophenyl)-3-hydroxypyridine-2-carbonyl]amino}acetic acid or a pharmaceutically acceptable salt, solvate, or hydrate thereof, wherein the daily dose is about 450 mg. In certain embodiments, the compound is administered in a formulation as described in Section 5.3.

In certain such embodiments, the daily dose is increased by about 150 mg such that the daily dose of the compound is about 600 mg. In certain embodiments, the daily dose is decreased by about 150 mg, such that the daily dose of the compound is about 300 mg. In certain embodiments, the daily dose is decreased by about 300 mg, such that the daily dose of the compound is about 150 mg. In certain embodiments, the compound is administered in a formulation as described in Section 5.3.

In certain embodiments, the compound is {[5-(3-chlorophenyl)-3-hydroxypyridine-2-carbonyl]amino}acetic acid. In certain embodiments, the compound is a pharmaceutically acceptable salt of {[5-(3-chlorophenyl)-3-hydroxypyridine-2-carbonyl]amino}acetic acid. In certain embodiments, the compound is a solvate of {[5-(3-chlorophenyl)-3-hydroxypyridine-2-carbonyl]amino}acetic acid. In certain embodiments, the compound is a hydrate of {[5-(3-chlorophenyl)-3-hydroxypyridine-2-carbonyl]amino}acetic acid.

In certain embodiments, the compound is administered in a formulation as described in Section 5.3.

In certain embodiments, the chronic kidney disease is stage 3, 4, or 5 chronic kidney disease. In certain such embodiments, the chronic kidney disease is pre-dialysis chronic kidney disease. In certain such embodiments, the chronic kidney disease is non-dialysis dependent chronic kidney disease. In certain embodiments, the patient has not been previously treated for anemia, such as anemia secondary to chronic kidney disease. In certain alternative embodiments, the patient has been previously treated for anemia, such as anemia secondary to chronic kidney disease.

In certain embodiments, the invention relates to a method of treating anemia in a subject as described in Section 5.4, such as anemia secondary to non-dialysis dependent chronic kidney disease, comprising administering to a patient having anemia a daily dose of a compound which is {[5-(3-chlorophenyl)-3-hydroxypyridine-2-carbonyl]amino}acetic acid or a pharmaceutically acceptable salt, solvate, or hydrate thereof; measuring the hemoglobin level in the patient after an administration of the daily dose of the compound and then again a period of time later, wherein when the hemoglobin level in the patient is between about 11.0 and about 12.2 g/dL and the level of hemoglobin has increased by greater than about 1.5 g/dL as compared to the level measured the period of time earlier; or when the hemoglobin level in the patient is between about 12.3 and about 12.9 g/dL and the level of hemoglobin has increased by between about 1.0 and about 1.4 g/dL as compared to the level measured the period of time earlier; or when the hemoglobin level in the patient is between about 12.3 and about 12.9 g/dL and the level of hemoglobin has increased by greater than about 1.5 g/dL as compared to the level measured the period of time earlier; or administering an adjusted daily dose of the compound that is 300 mg less than the daily dose. In certain embodiments, the daily dose of the compound is about 450 mg. In certain embodiments, the compound is administered in a formulation as described in Section 5.3.

5.6 Diseases Associated with HIF Prolyl Hydroxylase Modulation

The formulations provided herein in Section 5.3 can be used in methods for treating and/or preventing and/or controlling in a patient, for example as described in Section 5.4, inter alia, Peripheral Vascular Disease (PVD); Coronary Artery Disease (CAD); heart failure; ischemia; anemia; wound healing; ulcers; ischemic ulcers; inadequate blood supply; poor capillary circulation; small artery atherosclerosis; venous stasis; atherosclerotic lesions (e.g., in coronary arteries); angina; myocardial infarction; diabetes; hypertension; Buerger's disease; diseases associated with abnormal levels of VEGF, GAPDH, and/or EPO; Crohn's disease; ulcerative colitis; psoriasis; sarcoidosis; rheumatoid arthritis; hemangiomas; Osler-Weber-vasculitis disease; hereditary hemorrhagic telangiectasia; solid or blood borne tumors and acquired immune deficiency syndrome; atrial arrhythmias; ischemic tissue damage in tissues such as: cardiac tissue, such as myocardium and cardiac ventricles, skeletal muscle, neurological tissue, such as from the cerebellum, internal organs, such as the stomach, intestine, pancreas, liver, spleen, and lung; and distal appendages such as fingers and toes. Specifically, provided herein are methods for treating and/or preventing and/or controlling, inter alia, Peripheral Vascular Disease (PVD); Coronary Artery Disease (CAD); heart failure; ischemia; anemia; wound healing; ulcers; ischemic ulcers; inadequate blood supply; poor capillary circulation; small artery atherosclerosis; venous stasis; atherosclerotic lesions (e.g., in coronary arteries); angina; myocardial infarction; diabetes; hypertension; Buerger's disease; diseases associated with abnormal levels of VEGF, GAPDH, and/or EPO; Crohn's disease; ulcerative colitis; psoriasis; sarcoidosis; rheumatoid arthritis; hemangiomas; Osler-Weber-vasculitis disease; hereditary hemorrhagic telangiectasia; solid or blood borne tumors and acquired immune deficiency syndrome; atrial arrhythmias; ischemic tissue damage in tissues such as: cardiac tissue, such as myocardium and cardiac ventricles, skeletal muscle, neurological tissue, such as from the cerebellum, internal organs, such as the stomach, intestine, pancreas, liver, spleen, and lung; and distal appendages such as fingers and toes, wherein the method comprises administering a pharmaceutically effective amount of a HIF prolyl hydroxylase inhibitor or a HIF-alpha stabilizer in a formulations provided herein in Section 5.3, wherein the pharmaceutically effective amount is suitable to reduce the severity or frequency of at least one symptom of these diseases while:

a) restoring or maintaining the diurnal pattern of EPO serum levels;
b) increasing the total iron binding capacity;
c) increasing the total iron binding capacity without increasing significantly the total iron levels; and/or
d) not significantly decreasing hepcidin levels.

Atherosclerotic PVD can present in three ways:
1) Asymptomatic PVD diagnosed on the basis of noninvasive testing (usually physical exam);
2) Intermittent claudication with symptoms of leg pain with exercise; and
3) Critical limb ischemia with leg pain at rest and limb-threatening ischemic changes (usually non-healing or infected cutaneous ulcerations).

The present disclosures also relate to methods for regulating blood flow, oxygen delivery and/or energy utilization in ischemic tissues, wherein the methods can comprise administering to a human an effective amount of one or more compounds or pharmaceutically acceptable salts or tautomers thereof disclosed herein.

The formulations recited herein in Section 5.3 can have a number of utilities, and address several unmet medical needs, inter alia:

1) Providing compositions effective as inhibitors of HIF prolyl hydroxylase, thereby stimulating an angiogenic response in human tissue, thereby providing a method for increasing blood flow, oxygen delivery and energy utilization in ischemic tissues;
2) Providing compositions effective as human protein HIF prolyl hydroxylase inhibitors, and thereby increasing the concentration of HIF-1alpha leading to greater activation and sustaining the of various biological pathways that are the normal response to cellular hypoxia;
3) Providing compositions effective in stimulating an EPO response in cells and thereby enhancing the maintenance of red blood cells by controlling the proliferation and differentiation of erythroid progenitor cells into red blood cells;
4) Providing compositions effective in stimulating an angiogenic response and thereby increasing the number and density of blood vessels and thus alleviating the adverse consequences of hypertension and diabetes, inter alia, claudication, ischemic ulcers, accelerated hypertension, and renal failure;
5) Providing compositions that activate Vascular Endothelial Growth Factor (VEGF) gene transcription in hypoxic cells thus increasing stimulus of important biological responses, inter alia, vasodilation, vascular permeability, and endothelial cell migration and proliferation.

6) Providing compositions that induce the production of soluble VEGF, an inhibitor of VEGF, in hypoxic cells thus increasing stimulus of important biological responses, inter alia, anti-angiogenic activities.

Therefore, these and other unmet medical needs are resolved by the HIF prolyl hydroxylase inhibitors of the present disclosure, which are capable of regulating blood flow, oxygen delivery and energy utilization in ischemic tissues that are caused by insufficient regulation of HIF prolyl hydroxylase. Those of skill in the art will also recognize that inhibition of HIF-1-alpha prolyl hydroxylase enzymes will have other positive medical effects on human tissue and the alleviation of symptoms and disease states other than those symptoms or diseases states that are specifically pointed out in the present disclosure. However, as greater details arise concerning disease states and conditions related to the angiogenic process, these yet undisclosed or yet unknown conditions will be positively affected by compositions which stimulate the body own response to hypoxia and other low blood oxygen conditions.

In certain embodiments, provided herein are methods for treating or preventing a disease or disorder ameliorated by modulation of HIF prolyl hydroxylase comprising administering to a patient having a disease ameliorated by modulation of HIF prolyl hydroxylase an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain such embodiments, the compound is administered from one to three, such as one, two or three times in the course of a 24 hour period. In certain such embodiments, provided herein are methods for treating or preventing a disease ameliorated by modulation of HIF prolyl hydroxylase comprising administering to a patient having a disease or disorder ameliorated by modulation of HIF prolyl hydroxylase an effective amount of {[5-(3-chlorophenyl)-3-hydroxypyridine-2-carbonyl]amino}acetic acid once daily. In certain such embodiments, the daily dose is about 150 mg, about 300 mg, about 450 mg, about 600 mg, or about 750 mg of {[5-(3-chlorophenyl)-3-hydroxypyridine-2-carbonyl] amino}acetic acid in a formulation as provided herein in Section 5.3. In certain such embodiments, provided herein are methods for treating or preventing a disease ameliorated by modulation of HIF prolyl hydroxylase comprising administering to a patient having a disease or disorder ameliorated by modulation of HIF prolyl hydroxylase an effective amount of 2-(5-(3-fluorophenyl)-3-hydroxypicolinamido)acetic acid once daily. In certain such embodiments, the daily dose is about 150 mg, about 300 mg, about 450 mg, about 600 mg, or about 750 mg of 2-(5-(3-fluorophenyl)-3-hydroxypicolinamido)acetic acid in a formulation as provided herein in Section 5.3. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of treating or preventing a disease or disorder in a patient, for example as described in Section 5.4, ameliorated by inhibiting HIF prolyl hydroxylase (e.g., PHD1, PHD2, and/or PHD3), comprising administering to a patient having a disease or disorder ameliorated by inhibiting HIF prolyl hydroxylase an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain such embodiments, provided herein are methods of treating or preventing a disease or disorder ameliorated by inhibiting PHD1, comprising administering to a patient having a disease or disorder ameliorated by inhibiting PHD1 an effective amount of 5-(3-chlorophenyl)-3-hydroxypyridine-2-carbonyl]amino}acetic acid according to the formulations and dose and/or dosing regimen described herein in Section 5.3 and Section 5.7. In certain such embodiments, provided herein are methods of treating or preventing a disease or disorder ameliorated by inhibiting PHD1, comprising administering to a patient having a disease or disorder ameliorated by inhibiting PHD1 an effective amount of 2-(5-(3-fluorophenyl)-3-hydroxypicolinamido)acetic acid according to the formulations and dose and/or dosing regimen described herein in Section 5.3 and Section 5.7. In certain such embodiments, provided herein are methods of treating or preventing a disease or disorder ameliorated by inhibiting PHD2, comprising administering to a patient having a disease or disorder ameliorated by inhibiting PHD2 an effective amount of 5-(3-chlorophenyl)-3-hydroxypyridine-2-carbonyl]amino}acetic acid according to the formulations and dose and/or dosing regimen described herein in Section 5.3 and Section 5.7. In certain such embodiments, provided herein are methods of treating or preventing a disease or disorder ameliorated by inhibiting PHD2, comprising administering to a patient having a disease or disorder ameliorated by inhibiting PHD2 an effective amount of 2-(5-(3-fluorophenyl)-3-hydroxypicolinamido)acetic acid according to the formulations and dose and/or dosing regimen described herein in Section 5.3 and Section 5.7. In certain such embodiments, provided herein are methods of treating or preventing a disease or disorder ameliorated by inhibiting PHD3, comprising administering to a patient having a disease or disorder ameliorated by inhibiting PHD3 an effective amount of 5-(3-chlorophenyl)-3-hydroxypyridine-2-carbonyl]amino}acetic acid according to the formulations and dose and/or dosing regimen described herein in Section 5.3 and Section 5.7. In certain such embodiments, provided herein are methods of treating or preventing a disease or disorder ameliorated by inhibiting PHD3, comprising administering to a patient having a disease or disorder ameliorated by inhibiting PHD3 an effective amount of 2-(5-(3-fluorophenyl)-3-hydroxypicolinamido)acetic acid according to the formulations and dose and/or dosing regimen described herein in Section 5.3 and Section 5.7.

In certain embodiments, provided herein are methods of treating or preventing a disease or disorder in a patient, for example as described in Section 5.4, ameliorated by stabilizing HIF-alpha (e.g., HIF-1-alpha, HIF-2-alpha, and/or HIF-3-alpha), comprising administering to a patient having a disease or disorder ameliorated by stabilizing HIF-alpha an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, or about 600 mg. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily. In certain such embodiments, provided herein are methods of treating or preventing a disease or disorder ameliorated by stabilizing HIF-1-alpha, comprising administering to a patient having a disease or disorder ameliorated by stabilizing HIF-1-alpha an effective amount of 5-(3-chlorophenyl)-3-hydroxypyridine-2-carbonyl]amino}acetic acid according to the formulations and dose and/or dosing regimen described herein in Section 5.3 and Section 5.7. In certain such embodiments, provided herein are methods of treating or preventing a disease or disorder ameliorated by stabilizing HIF-1-alpha, comprising administering to a patient having a disease or disorder ameliorated by stabilizing HIF-1-alpha an effective amount of 2-(5-(3-fluorophenyl)-3-hydroxypicolinamido)acetic acid according to the formulations and dose and/or dosing regimen described herein in Section 5.3 and Section 5.7. In certain such embodiments, provided herein are methods of treating or preventing a disease or disorder ameliorated by stabilizing HIF-2-alpha, comprising administering to a patient having a disease or disorder ameliorated by inhibiting HIF-2-alpha an effective amount of 5-(3-chlorophenyl)-3-hydroxypyridine-2-carbonyl]amino}acetic acid according to the formulations and dose and/or dosing regimen described herein in Section 5.3 and Section 5.7. In certain such embodiments, provided herein are methods of treating or preventing a disease or disorder ameliorated by stabilizing HIF-2-alpha, comprising administering to a patient having a disease or disorder ameliorated by inhibiting HIF-2-alpha an effective amount of 2-(5-(3-fluorophenyl)-3-hydroxypicolinamido)acetic acid according to the formulations and dose and/or dosing regimen described herein in Section 5.3 and Section 5.7.

In certain such embodiments, provided herein are methods of treating or preventing a disease or disorder in a patient, for example as described in Section 5.4, ameliorated by stabilizing HIF-3-alpha, comprising administering to a patient having a disease or disorder ameliorated by stabilizing HIF-3-alpha an effective amount of 5-(3-chlorophenyl)-3-hydroxypyridine-2-carbonyl]amino}acetic acid according to the formulations and dose and/or dosing regimen described herein in Section 5.3 and Section 5.7. In certain such embodiments, provided herein are treating or preventing a disease or disorder ameliorated by stabilizing HIF-3-alpha, comprising administering to a patient having a disease or disorder ameliorated by stabilizing HIF-3-alpha an effective amount of 2-(5-(3-fluorophenyl)-3-hydroxypicolinamido)acetic acid according to the formulations and dose and/or dosing regimen described herein in Section 5.3 and Section 5.7.

In certain embodiments, provided herein are methods of treating or preventing a disease or condition related to diminished endogenous production of erythropoietin (EPO) in a patient, for example as described in Section 5.4, comprising administering to a patient having a disease or disorder related to diminished endogenous production of EPO an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimens described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of treating or preventing anemia (e.g., anemia secondary to or associated with chronic kidney disease, anemia secondary to chronic heart disease, idiopathic anemia of aging, anemia of chronic disease, myelodysplastic syndrome, bone marrow fibrosis, other aplastic or dysplastic anemias, chemotherapy induced anemia (including chemotherapy for treating cancer, hepatitis C, or other chronic drug therapy that reduces bone marrow production), anemia resulting from blood loss, anemia resulting from iron deficiency, anemia resulting from vitamin B12 deficiency, sickle cell disease, or thalassemia), comprising administering to a patient having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain embodiments, provided herein are methods of treating anemia, such as anemia secondary to chronic kidney disease, comprising administering to a patient having anemia an effective amount of 5-(3-chlorophenyl)-3-hydroxypyridine-2-carbonyl]amino}acetic acid. In certain embodiments, provided herein are methods of treating anemia, such as anemia secondary to chronic kidney disease, comprising administering to a patient having anemia an effective amount of 2-(5-(3-fluorophenyl)-3-hydroxypicolinamido)acetic acid. In certain embodiments, provided herein are methods of treating anemia, such as anemia secondary to non-dialysis dependent chronic kidney disease, comprising administering to a patient having anemia an effective amount of 2-(5-(3-fluorophenyl)-3-hydroxypicolinamido)acetic acid. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are treating or preventing anemia secondary to chronic kidney disease (CKD), including non-dialysis dependent CKD, in a patient, for example as described in Section 5.4, comprising administering to a patient having anemia secondary to CKD an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily. In certain embodiments, the daily dose is administered once daily. In certain embodiments, the CKD is stage 1, 2, 3, 4, or 5 chronic kidney disease. In certain such embodiments, the CKD is stage 3, 4, or 5 chronic kidney disease. In certain embodiments, the CKD is stage 1 chronic kidney disease. In certain embodiments, the CKD is stage 2 chronic kidney disease. In certain embodiments, the CKD is stage 3 chronic kidney disease. In certain embodiments, the CKD is stage 4 chronic kidney disease. In certain embodiments, the CKD is stage 5 chronic kidney disease. In certain embodiments, the chronic kidney disease is pre-dialysis chronic kidney disease. In certain embodiments, the patient is a dialysis patient and these patients may be referred to as having end stage renal disease (ESRD). In certain such embodiments, the anemia, such as anemia secondary to CKD or ESRD may be refractory to treatment with an erythropoiesis stimulating agent, including a rhEPO product, such as, epoetin alfa, epoetin beta, darbepoetin, or peginesatide. In certain embodiments, the patient has been previously treated for anemia, while in certain alternative embodiments, the patient has not previously been treated for anemia.

In certain embodiments, provided herein are methods of treating or preventing an angiogenesis-related disease or disorder in a patient, for example as described in Section 5.4, comprising administering to a patient having angiogenesis-related disease or disorder an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain embodiments, provided herein are methods of regulating angiogenesis, comprising administering to a patient an effective amount of 5-(3-chlorophenyl)-3-hydroxypyridine-2-carbonyl]amino}acetic acid according to the dose and/or dosing regimen described herein. In certain embodiments, provided herein are methods of regulating angiogenesis, comprising administering to a patient an effective amount of 2-(5-(3-fluorophenyl)-3-hydroxypicolinamido)acetic acid according to the dose and/or dosing regimen described herein. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of treating or preventing disease or disorder affected by the level of VEGF or GAPDH in a patient, for example as described in Section 5.4, comprising administering to a patient having a disease or disorder affected by the level of VEGF or GADPH an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations dose and/or dosing regimen described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of promoting wound healing, comprising administering to a patient, for example as described in Section 5.4, having a wound an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of enhancing the revascularization of damaged tissue or increasing vasculature in a patient, for example as described in Section 5.4, comprising administering to a patient having damaged tissue an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain embodiments, provided herein are methods of vascularizing ischemic tissue, comprising administering to a patient having ischemic tissue an effective amount of 5-(3-chlorophenyl)-3-hydroxypyridine-2-carbonyl]amino}acetic acid according to the dose and/or dosing regimen described herein. In certain embodiments, provided herein are methods of vascularizing ischemic tissue, comprising administering to a patient having ischemic tissue an effective amount of 2-(5-(3-fluorophenyl)-3-hydroxypicolinamido)acetic acid according to formulations and the dose and/or dosing regimen described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of promoting the growth of skin graft replacements, comprising administering to a patient having a skin graft, for example as described in Section 5.4, an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of promoting tissue repair in the context of guided tissue regeneration (GTR), comprising administering to a patient, for example as described in Section 5.4, an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl]amino}acetic acid or 2-(5-(3-fluorophenyl)-3-hydroxypicolinamido)acetic acid) according to the formulations and dose and/or dosing regimen described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods of treating or preventing a disease or disorder selected from diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma post-laser complications, diseases associated with rubeosis, and proliferative vitreoretinopathy, Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors, acquired immune deficiency syndrome, skeletal muscle and myocardial ischemia, stroke, coronary artery disease, peripheral vascular disease, and coronary artery disease, comprising administering to a patient having such a disease or disorder an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, 5-(3-chlorophenyl)-3-hydroxypyridine-2-carbonyl] amino}acetic acid or 2-(5-(3-fluorophenyl)-3-hydroxypicolinamido)acetic acid) according to the formulations and/or dosages and/or dose and/or dosing regimens described herein in Section 5.3 and Section 5.7. In certain such embodiments, the daily dose is about 150 mg, about 300 mg, about 450 mg, about 600 mg, or about 750 mg of {[5-(3-chlorophenyl)-3-hydroxypyridine-2-carbonyl]amino}acetic acid. In certain such embodiments, the daily dose is about 150 mg, about 300 mg, about 450 mg, about 600 mg, or about 750 mg of 2-(5-(3-fluorophenyl)-3-hydroxypicolinamido)acetic acid. In certain such embodiments, the daily dose is about 150 mg, about 300 mg, about 450 mg, or about 600 mg. Such daily doses may be administered orally, once daily, twice daily, or three times daily, preferably once daily.

5.7 Doses and Dosing Regimens

The specific doses for uses of a HIF prolyl hydroxylase inhibitor or a HIF-alpha stabilizer described in this section can be administered in any manner known to the skilled artisan. Doses of the compounds described herein may be taken orally, topically or intravenously. Doses of the compounds described herein may be taken while fasting, together with fluids, or together with food of any kind. In specific embodiments, doses of the compounds described herein may be taken or 1, 2, 3, 4, 5, 6, 7, 8, 9, 10, 11, or 12 hours after a meal, or 1, 2, 3, 4, 5, 6, 7, 8, 9, 10, 11, or 12 hours before a meal. Doses of the compounds described herein may be taken at any time of day. In certain embodiments, repeat doses are administered at the same time during the day. In certain embodiments, the dose doses are administered in the morning, around mid-day, or in the evening. In certain embodiments, the doses are administered between 4.00 am and 2.00 pm. In certain embodiments, the doses are administered between 5.00 am and 1.00 pm. In certain embodiments, the doses are administered between 6.00 am and 12.00 noon. In certain embodiments, the doses are administered between 7.00 am and 11.00 am. In certain embodiments, the doses are administered between 8.00 am and 10.00 am. In certain embodiments, the doses are administered before, during, or after breakfast. Administration and dosing regimens may be adjusted as described herein.

In a specific embodiment, a subject is initially treated with 3 tablets of 150 mg of Compound 1 daily (450 mg/day). Dose levels of the compound include 150, 300, 450, and 600 mg. Thereafter, the medication is taken once daily during the course of treatment. The subject should take the study medication with 4 ounces of water or other oral beverage, regardless of food intake. The dose is taken at approximately the same time each day, preferably between 7 AM and 2 PM.

Various parameters are described herein to guide the dosing regimen of a HIF prolyl hydroxylase inhibitor or a HIF-alpha stabilizer for the prevention and/or treatment of various diseases and disorders as described in Section 5.6, such as anemia (e.g., anemia secondary to non-dialysis dependent chronic kidney disease). This section provides several specific doses for such uses of a HIF prolyl hydroxylase inhibitor or a HIF-alpha stabilizer. In certain embodiments, such a dose is the initial dose at the beginning of a treatment. In other embodiments, such a dose is the adjusted dose at a later time during the course of treatment. In certain embodiments, the HIF prolyl hydroxylase inhibitor or a HIF-alpha stabilizer is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof. In a specific embodiment, the compound is Compound 1 or a pharmaceutically acceptable salt, solvate, or hydrate thereof. In a specific embodiment, the compound is Compound 7 or a pharmaceutically acceptable salt, solvate, or hydrate thereof. In certain embodiments, the compound is administered in a formulation as described in Section 5.3.

Dose Formulations

In certain specific embodiments, the doses described in this Section 5.7 are doses in form of a formulation comprising intra-granular components, extra-granular components, and film coating components as described in Section 5.3. In a specific embodiment, the intra-granular component comprises about 60% by weight of Compound 1, about 20% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain specific embodiments, the doses described in this Section 5.7 are doses in form of a formulation comprising intra-granular components, extra-granular components, and film coating components as described in Section 5.3. In a specific embodiment, the intra-granular component comprises about 65% by weight of Compound 1, about 25% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain specific embodiments, the doses described in this Section 5.7 are doses in form of a formulation comprising intra-granular components, extra-granular components, and film coating components as described in Section 5.3. In a specific embodiment, the intra-granular component comprises about 70% by weight of Compound 1, about 20% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain specific embodiments, the doses described in this Section 5.7 are doses in form of a formulation comprising intra-granular components, extra-granular components, and film coating components as described in Section 5.3. In a specific embodiment, the intra-granular component comprises about 75% by weight of Compound 1, about 15% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain specific embodiments, the doses described in this Section 5.7 are doses in form of a formulation comprising intra-granular components, extra-granular components, and film coating components as described in Section 5.3. In a specific embodiment, the intra-granular component comprises about 80% by weight of Compound 1, about 10% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

5.7.1 Dosing Regimens

In certain embodiments, provided herein are methods for treating anemia, such as anemia secondary to non-dialysis dependent chronic kidney disease, comprising administering to a patient as described in Section 5.4 having anemia, a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) which is between about 100 mg and about 1,200 mg, about 200 mg and about 1,000 mg, about 400 mg and about 800 mg, or about 450 mg and about 600 mg, or about 300 mg and about 600 mg. In certain embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) is between about 150 mg and about 600 mg. In certain embodiments, the daily dose of the compound is between about 150 mg and about 300 mg, about 300 and about 600 mg, or between about 600 mg and about 750 mg. In certain embodiments, the daily dose is about 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150 mg, or even about 1,200 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain embodiments, the daily dose is at least about 300 mg, at least about 450 mg, or even at least about 600 mg. In certain specific embodiments, the dose is administered in a formulation as described in Section 5.3.

In certain embodiments, the daily dose is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain embodiments, the daily dose is about 150 mg, about 300 mg, about 450 mg, or about 600 mg. In certain embodiments, the daily dose is not 240 mg, 370 mg, 500 mg or 630 mg of Compound 1. In certain embodiments, the daily dose is about 240 mg, 370 mg, 500 mg or about 630 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain specific embodiments, the dose is administered in a formulation as described in Section 5.3.

In certain embodiments, provided herein are methods for treating anemia, such as anemia secondary to non-dialysis dependent chronic kidney disease, comprising administering to a patient having anemia daily dose of a compound which is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein the compound is administered continuously and/or indefinitely. In certain specific embodiments, the dose is administered in a formulation as described in Section 5.3.

In certain embodiments, provided herein are methods for treating anemia, such as anemia secondary to non-dialysis dependent chronic kidney disease, comprising administering to a patient as described in Section 5.4 having anemia a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein the daily dose is about 450 mg. In certain such embodiments, a daily dose of about 450 mg comprises three unit dosage forms, such as three tablets, each comprising about 150 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain embodiments, a daily dose of about 450 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be increased by about 150 mg such that the daily dose of the compound is about 600 mg. In certain embodiments, a daily dose of 450 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be decreased by about 150 mg, such that the daily dose of the compound is about 300 mg. In certain embodiments, a daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be decreased by about 300 mg, such that the daily dose of the compound is about 150 mg. In certain embodiments, the daily dose may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose may be increased or decreased by an amount between about 75 mg and about 250 mg, about 100 mg and about 225 mg, or about 125 mg and about 200 mg. In certain such embodiments, the daily dose does not exceed about 600 mg or about 750 mg. In certain specific embodiments, the dose is administered in a formulation as described in Section 5.3.

In certain embodiments, provided herein are methods for treating anemia, such as anemia secondary to non-dialysis dependent chronic kidney disease, comprising administering to a patient as described in Section 5.4 having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein the compound may be administered continuously and/or indefinitely, such as for more than 42 consecutive days. In certain such embodiments, a daily dose of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. In certain specific embodiments, the dose is administered in a formulation as described in Section 5.3.

In certain embodiments, provided herein are methods for treating anemia, such as anemia secondary to non-dialysis dependent chronic kidney disease, comprising administering to a patient as described in Section 5.4 having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein hemoglobin levels of a patient are maintained at a level of at least about 10.0 g/dL and at or below about 13.0 g/dL. In certain such embodiments, the hemoglobin levels are maintained at a level of at least about 11.0 g/dL and at or below about 13.0 g/dL. In certain such embodiments, the hemoglobin levels are maintained at a level of at least about 11.0 g/dL and at or below about 12.0 g/dL. In certain such embodiments, a daily dose of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. In certain specific embodiments, the dose is administered in a formulation as described in Section 5.3.

In certain embodiments, provided herein are methods for treating anemia, such as anemia secondary to non-dialysis dependent chronic kidney disease, comprising administering to a patient as described in Section 5.4 having anemia an effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid), wherein level of hemoglobin of a patient are increased at least about 1.2 g/dL relative to a baseline hemoglobin level. In certain such embodiments, a daily dose of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid). In certain such embodiments, the daily dose is about 150 mg, about 300 mg, about 450 mg, or about 600 mg. In certain specific embodiments, the dose is administered in a formulation as described in Section 5.3.

In certain embodiments, administration of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be suspended if the level of hemoglobin is at or above 13.0 g/dL. In certain such embodiments, administration of the compound may be resumed once the level of hemoglobin is at or below 12.5 g/dL. In certain specific embodiments, the compound is administered in a formulation as described in Section 5.3.

In certain embodiments, hemoglobin levels are monitored and the dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be adjusted based on the level of hemoglobin and/or the change in level of hemoglobin. In certain embodiments, the dose may be adjusted by either increasing or reducing the amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) by 150 mg or even by 300 mg. In certain specific embodiments, the dose is administered in a formulation as described in Section 5.3.

5.7.2 Dose Adjustment

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is less than about 10.0 g/dL and the level of hemoglobin has decreased by less than about 0.5 g/dL as compared to the level at the first measurement; or if the hemoglobin level in the patient at the second measurement is less than about 10.0 g/dL and the level of hemoglobin has changed by up to about 0.4 g/dL as compared to the level at the first measurement; or if the hemoglobin level in the patient at the second measurement is between about 10.0 and about 10.9 g/dL and the level of hemoglobin has decreased by less than about 0.5 g/dL as compared to the level at the first measurement; then administering an adjusted daily dose of the compound that is greater than the initial daily dose. In certain such embodiments, the adjusted daily dose of the compound is about 150 mg greater than the initial daily dose.

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is less than about 10.0 g/dL and the level of hemoglobin has increased by greater than about 1.5 g/dL as compared to the level at the first measurement; or if the hemoglobin level in the patient at the second measurement is between about 10.0 and about 10.9 g/dL and the level of hemoglobin has increased by greater than about 1.5 g/dL as compared to the level at the first measurement; or if the hemoglobin level in the patient at the second measurement is between about 11.0 and about 12.2 g/dL and the level of hemoglobin has increased by between about 1.0 and about 1.4 g/dL as compared to the level at the first measurement; or if the hemoglobin level in the patient at the second measurement is between about 12.3 and about 12.9 g/dL and the level of hemoglobin has decreased by up to about 0.4 g/dL or increased by up to about 0.4 g/dL as compared to the at the first measurement; or if the hemoglobin level in the patient at the second measurement is between about 12.3 and about 12.9 g/dL and the level of hemoglobin has increased by about 0.5 to about 0.9 g/dL as compared to the level at the first measurement; then administering an adjusted daily dose of the compound that is less than the initial daily dose. In certain such embodiments, the adjusted daily dose of the compound is about 150 mg less than the initial daily dose. In certain embodiments, the lowest dose level is 150 mg per day. Patients already on the lowest dose level will continue on 150 mg per day unless their Hgb increases to ≥13.0 g/dL.

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is between about 11.0 and about 12.2 g/dL and the level of hemoglobin has increased by greater than about 1.5 g/dL as compared to the level at the first measurement; or if the hemoglobin level in the patient at the second measurement is between about 12.3 and about 12.9 g/dL and the level of hemoglobin has increased by between about 1.0 and about 1.4 g/dL as compared to the level at the first measurement; or if the hemoglobin level in the patient at the second measurement is between about 12.3 and about 12.9 g/dL and the level of hemoglobin has increased by greater than about 1.5 g/dL as compared to the level at the first measurement; then administering an adjusted daily dose of the compound that is less than the initial daily dose. In certain such embodiments, the adjusted daily dose of the compound is about 300 mg less than the initial daily dose. In certain embodiments, the lowest dose level is 150 mg per day. Patients already on the lowest dose level will continue on 150 mg per day unless their Hgb increases to ≥13.0 g/dL.

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is equal to or above 13.0 g/dL, then administering an adjusted daily dose of the compound that is less than the initial daily dose. In certain such embodiments, dosing is suspended. In certain such embodiments, dosing will be suspended if Hgb rises to ≥13 g/dL, and will not be restarted until Hgb reduces to ≤12.5 g/dL. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt, solvate, or hydrate thereof, taking a first measurement of the hemoglobin level in the patient and subsequently taking a second measurement of the hemoglobin level in the patient, wherein if the hemoglobin level in the patient at the second measurement is equal to or above 12.5 g/dL, then administering an adjusted daily dose of the compound that is less than the initial daily dose. In certain such embodiments, dosing is suspended. In certain such embodiments, dosing will be suspended if Hgb rises to ≥12.5 g/dL, and will not be restarted until Hgb reduces to ≤12.0 g/dL. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt, solvate, or hydrate thereof; taking a first measurement of the hemoglobin level in the patient and subsequently taking a second measurement of the hemoglobin level in the patient, wherein if the hemoglobin level in the patient at the second measurement is equal to or above 13.0 g/dL if the patient is an adult male or 12.5 g/dL if the patient is an adult female, then administering an adjusted daily dose of the compound that is less than the initial daily dose. In certain such embodiments, dosing is suspended. In certain such embodiments, dosing will be suspended if Hgb rises to ≥13.0 g/dL if the patient is an adult male or to ≥12.5 g/dL if the patient is an adult female, and will not be restarted until Hgb reduces to ≤12.5 g/dL if the patient is an adult male or ≤12.0 g/dL if the patient is an adult female. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is less than about 9.5 to 10.5 g/dL or about 9.75 to 10.25 g/dL and the level of hemoglobin has decreased by less than about 0.2 to 0.8, about 0.3 to 0.7, or about 0.4 to 0.6 g/dL as compared to the level at the first measurement; or if the hemoglobin level in the patient at the second measurement is less than about 9.5 to 10.5 g/dL or about 9.75 to 10.25 g/dL and the level of hemoglobin has changed by up to about 0.1 to 0.7, about 0.2 to 0.6, or about 0.3 to 0.5 g/dL as compared to the level at the first measurement; or if the hemoglobin level in the patient at the second measurement is between about 9.5 to 10.5 g/dL or about 9.75 to 10.25 g/dL and about 10.4 to 11.4 g/dL or about 10.65 to 11.15 g/dL and the level of hemoglobin has decreased by less than about 0.2 to 0.8, about 0.3 to 0.7, or about 0.4 to 0.6 g/dL as compared to the level at the first measurement; then administering an adjusted daily dose of the compound that is greater than the initial daily dose. In certain such embodiments, the adjusted daily dose of the compound is about 150 mg greater than the initial daily dose.

In certain embodiments, the dose may be adjusted by administering to a patient having anemia an initial daily dose of a compound which is {[5-(3-chlorophenyl)-3-hydroxy-pyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is less than about 9.5 to 10.5 g/dL or about 9.75 to 10.25 g/dL and the level of hemoglobin has increased by greater than about 1.2 to 1.8, about 1.3 to 1.7, or about 1.4 to 1.6 g/dL as compared to the level at the first measurement; or if the hemoglobin level in the patient at the second measurement is between about 9.5 to 10.5 or about 9.75 to 10.25 g/dL and about 10.4 to 11.4 g/dL or about 10.65 to 11.15 g/dL and the level of hemoglobin has increased by greater than about 1.2 to 1.8, about 1.3 to 1.7, or about 1.4 to 1.6 g/dL as compared to the level at the first measurement; or if the hemoglobin level in the patient at the second measurement is between about 10.5 to 11.5 g/dL or about 10.75 to 11.25 g/dL and about 11.7 to 12.7 g/dL or about 11.95 to 12.45 g/dL g/dL and the level of hemoglobin has increased by between about 0.7 to 1.3, about 0.8 to 1.2, or about 0.9 to 1.1 g/dL and about 1.1 to 1.7, about 1.2 to 1.6, or about 1.3 to 1.5 g/dL as compared to the level at the first measurement; or if the hemoglobin level in the patient at the second measurement is between about 11.8 to 12.8 g/dL or about 12.05 to 12.55 g/dL and about 12.4 to 13.9 g/dL or about 12.65 to 13.15 g/dL g/dL and the level of hemoglobin has decreased by up to about 0.1 to 0.7, about 0.2 to 0.6, or about 0.3 to 0.5 g/dL or increased by up to about 0.1 to 0.7, about 0.2 to 0.6, or about 0.3 to 0.5 g/dL as compared to the at the first measurement; or if the hemoglobin level in the patient at the second measurement is between about about 11.8 to 12.8 g/dL or about 12.05 to 12.55 g/dL and about 12.4 to 13.9 g/dL or about 12.65 to 13.15 g/dL g/dL and the level of hemoglobin has increased by about 0.2 to 0.8, about 0.3 to 0.7, or about 0.4 to 0.6 to about 0.6 to 1.2, about 0.7 to 1.1, or about 0.8 to 1.0 g/dL as compared to the level at the first measurement; then administering an adjusted daily dose of the compound that is less than the initial daily dose. In certain such embodiments, the adjusted daily dose of the compound is about 150 mg less than the initial daily dose. In certain embodiments, the lowest dose level is 150 mg per day. Patients already on the lowest dose level will continue on 150 mg per day unless their Hgb increases to ≥12.0, 12.5, or 13.0 g/dL.

In certain embodiments, the dose may be adjusted by administering to a patient having anemia an initial daily dose of a compound which is {[5-(3-chlorophenyl)-3-hydroxy-pyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is between about 10.5 to 11.5 g/dL or about 10.75 to 11.25 g/dL and about 11.7 to 12.7 g/dL or about 11.95 to 12.45 g/dL g/dL and the level of hemoglobin has increased by greater than about 1.2 to 1.8, about 1.3 to 1.7, or about 1.4 to 1.6 g/dL as compared to the level at the first measurement; or if the hemoglobin level in the patient at the second measurement is between about 11.8 to 12.8 g/dL or about 12.05 to 12.55 g/dL and about 12.4 to 13.9 g/dL or about 12.65 to 13.15 g/dL g/dL and the level of hemoglobin has increased by between about 0.7 to 1.3, about 0.8 to 1.2, or about 0.9 to 1.1 g/dL and about 1.1 to 1.7, about 1.2 to 1.6, or about 1.3 to 1.5 g/dL as compared to the level at the first measurement; or if the hemoglobin level in the patient at the second measurement is between about 11.8 to 12.8 g/dL or about 12.05 to 12.55 g/dL and about 12.4 to 13.9 g/dL or about 12.65 to 13.15 g/dL g/dL and the level of hemoglobin has increased by greater than about 1.2 to 1.8, about 1.3 to 1.7, or about 1.4 to 1.6 g/dL as compared to the level at the first measurement; then administering an adjusted daily dose of the compound that is less than the initial daily dose. In certain such embodiments, the adjusted daily dose of the compound is about 300 mg less than the initial daily dose. In certain embodiments, the lowest dose level is 150 mg per day. Patients already on the lowest dose level will continue on 150 mg per day unless their Hgb increases to ≥12.0, 12.5, or 13.0 g/dL.

In certain embodiments, the dose may be adjusted by administering to a patient having anemia an initial daily dose of a compound which is {[5-(3-chlorophenyl)-3-hydroxy-pyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is equal to or above 11.0, 11.5, 12.0, 12.5, 13.0, 13.5, or 14.0 g/dL, then administering an adjusted daily dose of the compound that is less than the initial daily dose. In certain such embodiments, dosing is suspended. In certain such embodiments, dosing will be suspended if Hgb rises to ≥11.0, 11.5, 12.0, 12.5, 13.0, 13.5, or 14.0 g/dL, and will not be restarted until Hgb reduces to ≤10.5, 11.0, 11.5, 12.0, 12.5, 13.0, or 13.5 g/dL. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxy-pyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is equal to or above 10.5, 11.0, 11.5, 12.0, 12.5, 13.0, or 13.5 g/dL, then administering an adjusted daily dose of the compound that is less than the initial daily dose. In certain such embodiments, dosing is suspended. In certain such embodiments, dosing will be suspended if Hgb rises to ≥10.5, 11.0, 11.5, 12.0, 12.5, 13.0, or 13.5 g/dL, and will not be restarted until Hgb reduces to ≤10.0, 10.5, 11.0, 11.5, 12.0, 12.5, or 13.0 g/dL. Factors that may temporarily change the Hgb level should be considered before suspending the dose. Hgb is assessed every 2 weeks during this time period.

In certain embodiments, the dose may be adjusted by administering to a patient having anemia an initial daily dose of a compound which is {[5-(3-chlorophenyl)-3-hydroxypyridine-2-carbonyl]amino}acetic acid or a pharmaceutically acceptable salt, solvate, or hydrate thereof administered in a formulation as described in Section 5.3; taking a first measurement of the hemoglobin level in the patient and subsequently taking a second measurement of the hemoglobin level in the patient, wherein if the hemoglobin level in the patient at the second measurement is equal to or above 11.0, 11.5, 12.0, 12.5, 13.0, 13.5, or 14.0 g/dL if the patient is an adult male or 10.5, 11.0, 11.5, 12.0, 12.5, 13.0, or 13.5 g/dL if the patient is an adult female, then administering an adjusted daily dose of the compound that is less than the initial daily dose. In certain such embodiments, dosing is suspended. In certain such embodiments, dosing will be suspended if Hgb rises to ≥11.0, 11.5, 12.0, 12.5, 13.0, 13.5, or 14.0 g/dL if the patient is an adult male or to ≥10.5, 11.0, 11.5, 12.0, 12.5, 13.0, or 13.5 g/dL if the patient is an adult female, and will not be restarted until Hgb reduces to ≤10.5, 11.0, 11.5, 12.0, 12.5, 13.0, or 13.5 g/dL if the patient is an adult male or ≤10.0, 10.5, 11.0, 11.5, 12.0, 12.5, or 13.0 g/dL if the patient is an adult female. Factors that may temporarily change the Hgb level should be considered before suspending the dose. Hgb is assessed every 2 weeks during this time period. The dose adjustment methods described herein may be applied in treatment regimens using any compound described herein, or any combination thereof.

Dosing Algorithm

In certain embodiments, the dose may be adjusted by administering to a patient having anemia an initial daily dose of a compound as described in Section 5.2 administered in a formulation as described in Section 5.3 (specifically, Formulation 1 or 2; see Section 6.2), taking a first measurement of the hemoglobin level in the patient and subsequently taking a second measurement of the hemoglobin level in the patient, and adjusting the dose as described below. In certain embodiments, the first measurement is a baseline measurement. In certain embodiments, the dose may be adjusted by administering to a patient having anemia an initial daily dose of a compound which is Compound 1 administered in a formulation as described in Section 5.3, taking a first measurement of the hemoglobin level in the patient and subsequently taking a second measurement of the hemoglobin level in the patient, and adjusting the dose as described below.

In certain embodiments, hemoglobin levels can be determined and monitored, e.g., via a HemoCue® point of care Hgb monitoring system, throughout the study to determine if the dose of study medication will be adjusted. In certain embodiments, Hgb can be obtained via HemoCue® every 2 weeks for monitoring for dose adjustment. In certain embodiments, Hgb can be obtained via HemoCue® every 4 weeks, unless more frequent monitoring is clinically indicated or warranted based on dosing changes. In certain embodiments, Hgb can be obtained via HemoCue® every 4, 6, 8, 10, 12 or 16 weeks. In certain embodiments, hemoglobin can also be assessed with a complete blood count (CBC) through the central laboratory for efficacy and safety evaluations; however, dose adjustments are based on the local HemoCue® Hgb value. In certain embodiments, the aim is to increase and maintain a Hgb level of 10-11 g/dL. In certain embodiments, the aim is to increase and maintain a Hgb level of 10-12 g/dL. In certain embodiments, the aim is to increase and maintain a Hgb level of 10-13 g/dL.

In certain embodiments, Compound 1 is administered in a formulation as described in Section 5.3, specifically Formulation 1 or 2 (see Section 6.2), and is dosed according to the following dose-adjustment algorithm guidelines. When adjusting therapy, Hgb rate of rise, rate of decline, and variability is considered. A single Hgb excursion may not require a dosing change.

5.7.3 Dose Adjustment Procedure in Patients with Chronic Kidney Disease

In certain embodiments, the dosing of a Compound 1 is adjusted during the course of treatment of a patient as described below. In certain specific embodiments, the dose is adjusted to correct anemia in a patient. In certain specific embodiments, the patient has non-dialysis dependent chronic kidney disease (NDD-CKD). In a specific embodiment, Compound 1 is formulated as Formulation 1 or Formulation 2.

In certain embodiments, a baseline value is determined immediately prior to the first administration of Compound 1. In certain embodiments, the initial daily dose administered to the patients is 300 mg/day. In certain specific embodiments, the initial daily dose is administered in form of two tablets of 150 mg each. In certain embodiments, the initial daily dose administered to the patients is 450 mg/day. In certain specific embodiments, the initial daily dose is administered in form of three tablets of 150 mg each. In certain specific embodiments, the initial daily dose is administered in the morning. In certain specific embodiments, the initial daily dose is administered between 7 am and 2 pm.

In certain embodiments, the daily dose of Compound 1 is not increased more frequently than once every 4 weeks during the course of treatment. Decreases in daily dose can occur more frequently, but frequent dose adjustments are to be avoided.

In certain embodiments, if the Hgb has not increased by more than 0.5 g/dL above the baseline value after 4 weeks of treatment, the daily dose of the compound is increased by 150 mg/day. The daily dose is increased by 150 mg/day every 4 weeks until Hgb is above 10.0 g/dL (maximum dose is 600 mg/day). In certain specific embodiments, if the Hgb has not increased by more than 0.5 g/dL above the baseline value after 4 weeks of treatment of a NDD-CKD patient with a daily dose of Compound 1, the daily dose of the compound is increased by 150 mg/day. In certain specific embodiments, the daily dose of Compound 1 is increased by 150 mg/day every 4 weeks until Hgb in the NDD-CKD patient is above 10.0 g/dL (maximum dose is 600 mg/day).

In certain embodiments, if the Hgb rises rapidly during treatment (e.g., more than 1.0 g/dL in any 2-week period), the daily dose is reduced by 150 mg/day. In certain specific embodiments, if the Hgb in a NDD-CKD patient rises rapidly during treatment with a daily dose of Compound 1 (e.g., more than 1.0 g/dL in any 2-week period), the daily dose is reduced by 150 mg/day.

In certain embodiments, if the Hgb falls below 10.0 g/dL, the daily dose is increased by 150 mg/day. In certain specific embodiments, if the Hgb in a NDD-CKD patient falls below 10.0 g/dL during treatment with a dose of Compound 1, the daily dose is increased by 150 mg/day.

In certain embodiments, if the Hgb level exceeds 11.0 g/dL, treatment is interrupted until the Hgb decreases to 10.5 g/dL or less. Thereafter, dosing is resumed with a daily dose reduced by 150 mg/day. In certain specific embodiments, if the Hgb level in a NDD-CKD patient exceeds 11.0 g/dL, treatment with Compound 1 is interrupted until the Hgb decreases to 10.5 g/dL or less. Thereafter, dosing with Compound 1 is resumed with a daily dose reduced by 150 mg/day.

In certain embodiments, if the Hgb level exceeds 12.0 g/dL, the daily dose is reduced by 150 mg. In certain embodiments, if the Hgb level exceeds 13.0 g/dL, treatment is interrupted until the Hgb decreases to 12.5 g/dL or less. Thereafter, dosing is resumed with with a daily dose reduced by 150 mg/day. In certain specific embodiments, if the Hgb level in a NDD-CKD patient exceeds 12.0 g/dL during treatment with a daily dose of Compound 1, the dose is reduced by 150 mg/day. In certain specific embodiments, if the Hgb level in a NDD-CKD patient exceeds 13.0 g/dL, treatment with Compound 1 is interrupted until the Hgb decreases to 12.5 g/dL or less. Thereafter, dosing with Compound 1 is resumed with a daily dose reduced by 150 mg/day.

In certain embodiments, if a dose adjustment is required to maintain Hgb at the desired level, the daily dose is adjusted by 150 mg/day. In certain specific embodiments, if a dose adjustment of Compound 1 is required to maintain Hgb in a NDD-CKD patient at the desired level, the daily dose is adjusted by 150 mg/day.

In certain embodiments, the dosing of Compound 1, is adjusted during the course of treatment of a patient as described below. In certain specific embodiments, the daily dose is adjusted for the maintenance treatment of anemia in a patient. In certain specific embodiments, the patient has non-dialysis dependent chronic kidney disease (NDD-CKD). In a specific embodiment, Compound 1 is formulated as Formulation 1 or Formulation 2.

In certain embodiments, a baseline value is determined immediately prior to the first administration of Compound 1. In certain embodiments, the initial daily dose administered to the patients is 300 mg/day. In certain specific embodiments, the initial daily dose is administered in form of two tablets of 150 mg each. In certain embodiments, the initial daily dose administered to the patients is 450 mg/day. In certain specific embodiments, the initial daily dose is administered in form of three tablets of 150 mg each. In certain specific embodiments, the initial daily dose is administered in the morning. In certain specific embodiments, the initial daily dose is administered between 7 am and 2 pm.

In certain embodiments, the daily dose of Compound 1 administered in a formulation as described in Section 5.3 is not increased more frequently than once every 4 weeks during the course of treatment. Decreases in daily dose can occur more frequently, but frequent dose adjustments are to be avoided.

In certain embodiments, if dose adjustment is required to maintain Hgb at the desired level, the daily dose of the compound is adjusted by 150 mg/day (maximum daily dose is 600 mg/day). In certain specific embodiments, if dose adjustment is required to maintain Hgb at the desired level in a NDD-CKD patient, the daily dose of Compound 1 is adjusted by 150 mg/day (maximum dose is 600 mg/day).

In certain embodiments, if the Hgb falls below 10.0 g/dL, the daily dose is increased by 150 mg/day. In certain specific embodiments, if the Hgb in a NDD-CKD patient falls below 10.0 g/dL during treatment with a dose of Compound 1, the daily dose is increased by 150 mg/day.

In certain embodiments, if the Hgb level exceeds 11.0 g/dL, treatment is interrupted until the Hgb decreases to 10.5 g/dL or less. Thereafter, dosing is resumed with with a daily dose reduced by 150 mg/day. In certain specific embodiments, if the Hgb level in a NDD-CKD patient exceeds 11.0 g/dL, treatment with Compound 1 is interrupted until the Hgb decreases to 10.5 g/dL or less. Thereafter, dosing with Compound 1 is resumed with a daily dose reduced by 150 mg/day.

In certain embodiments, if the Hgb level exceeds 12.0 g/dL, the daily dose is reduced by 150 mg/day. In certain embodiments, if the Hgb level exceeds 13.0 g/dL, treatment is interrupted until the Hgb decreases to 12.5 g/dL or less. Thereafter, dosing is resumed with with a daily dose reduced by 150 mg/day. In certain specific embodiments, if the Hgb level in a NDD-CKD patient exceeds 12.0 g/dL during treatment with a daily dose of Compound 1, the daily dose is reduced by 150 mg/day. In certain specific embodiments, if the Hgb level in a NDD-CKD patient exceeds 13.0 g/dL, treatment with Compound 1 is interrupted until the Hgb decreases to 12.5 g/dL or less. Thereafter, dosing with Compound 1 is resumed with a daily dose reduced by 150 mg/day.

In certain embodiments, during the administration of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) or a pharmaceutically acceptable salt, solvate, or hydrate thereof administered in a formulation as described in Section 5.3, the dose may not be increased more than once every 4 weeks, but may be decreased more frequently while avoiding frequent dose adjustments. In certain embodiments, the dose may be adjusted by administering to a patient having anemia an initial daily dose of the compound, taking a first measurement of the hemoglobin level in the patient and subsequently taking a second measurement of the hemoglobin level in the patient 4 weeks thereafter, and if the Hgb has not increased by more than 0.5 g/dL above the first value after 4 weeks, then administering an adjusted daily dose of the compound that is higher than the initial daily dose, e.g., an adjusted dose that is 150 mg higher than the initial dose. In certain embodiments, the dose may be further adjusted by taking 1, 2, 3, 4, 5, or more subsequent measurements of the hemoglobin level in the patient, and if the Hgb has not increased by more than 0.5 g/dL above the previous value, administering to the patient a daily dose of the compound that is higher than the previous daily dose. In certain embodiments, this adjustment process is continued until Hgb is above 10.0 g/dL. In certain embodiments, this adjustment process is continued until Hgb is above 8.0 g/dL, 8.5, g/dL, 9.0 g/dL, 9.5 g/dL, 10.0 g/dL, 10.5 g/dL, 11.0 g/dL, 11.5 g/dL, 12.0 g/dL, 12.5 g/dL, 13.0 g/dL, 13.5 g/dL, or 14.0 g/dL. In certain embodiments, the maximum daily dose of the compound is 600 mg/day. In certain embodiments, the maximum daily dose of the compound is 400 mg/day, 450 mg/day, 500 mg/day, 550 mg/day, 600 mg/day, 650 mg/day, 700 mg/day, 750 mg/day, or 800 mg/day.

In certain embodiments, the dose may be adjusted by administering to a patient having anemia an initial daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) or a pharmaceutically acceptable salt, solvate, or hydrate thereof administered in a formulation as described in Section 5.3, taking a first measurement of the hemoglobin level in the patient and subsequently taking a second measurement of the hemoglobin level in the patient, and if the Hgb rises rapidly (e.g., by more than 1 g/dL in any 2-week period), then administering an adjusted daily dose of the compound that is lower than the initial daily dose, e.g., an adjusted dose that is 150 mg lower than the initial dose.

In certain embodiments, the dose may be adjusted by administering to a patient having anemia an initial daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) or a pharmaceutically acceptable salt, solvate, or hydrate thereof administered in a formulation as described in Section 5.3, taking a first measurement of the hemoglobin level in the patient and subsequently taking a second measurement of the hemoglobin level in the patient, and if the Hgb level exceeds 11.0 g/dL, then administering an adjusted daily dose of the compound that is lower than the initial daily dose. In certain embodiments, the dose may be adjusted by administering to a patient having anemia an initial daily dose of the compound, taking a first measurement of the hemoglobin level in the patient and subsequently taking a second measurement of the hemoglobin level in the patient, and if the Hgb level exceeds 11.0 g/dL, then interrupting administering the daily dose until Hgb decreases to 10.5 g/dL or less, then subsequently resuming treatment by administering an adjusted daily dose of the compound that is lower than the initial daily dose. In certain embodiments, the adjusted daily dose of the compound is 50 mg, 100 mg, 150 mg, 200 mg, 250 mg, 300 mg, 350 mg, 400 mg, 450 mg, 500 mg, 550 mg, or 600 mg. In certain embodiments, the adjusted daily dose is 1.5 times, 2 times, 2.5 times, 3 times, 3.5 times, 4 times, 4.5 times, or 5 times higher than the initial dose. In certain embodiments, the initial dose is 1.5 times, 2 times, 2.5 times, 3 times, 3.5 times, 4 times, 4.5 times, or 5 times higher than the adjusted dose.

In certain embodiments, the dose may be adjusted by administering to a patient having anemia an initial daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) or a pharmaceutically acceptable salt, solvate, or hydrate thereof administered in a formulation as described in Section 5.3, taking a first measurement of the hemoglobin level in the patient and subsequently taking a second measurement of the hemoglobin level in the patient, and if the Hgb level exceeds 12.0 g/dL, then administering an adjusted daily dose of the compound that is lower than the initial daily dose. In certain embodiments, the dose may be adjusted by administering to a patient having anemia an initial daily dose of the compound, taking a first measurement of the hemoglobin level in the patient and subsequently taking a second measurement of the hemoglobin level in the patient, and if the Hgb level exceeds 13.0 g/dL, then interrupting administering the daily dose until Hgb decreases to 12.5 g/dL or less, then subsequently resuming treatment by administering an adjusted daily dose of the compound that is lower than the initial daily dose. In certain embodiments, the adjusted daily dose is 50 mg, 100 mg, 150 mg, 200 mg, 250 mg, 300 mg, 350 mg, 400 mg, 450 mg, 500 mg, 550 mg, or 600 mg. In certain embodiments, the adjusted daily dose is 1.5 times, 2 times, 2.5 times, 3 times, 3.5 times, 4 times, 4.5 times, or 5 times higher than the initial dose. In certain embodiments, the initial dose is 1.5 times, 2 times, 2.5 times, 3 times, 3.5 times, 4 times, 4.5 times, or 5 times higher than the adjusted dose.

5.7.4 Daily Doses

In certain embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be increased after a period of time, beginning on the day a patient is given a daily dose of the compound. In certain embodiments, the period of time is from about one week to about eight weeks, such as from about two weeks to about seven weeks, about three weeks to about six weeks, or about four weeks. In certain specific embodiments, the compound is administered in a formulation as described in Section 5.3.

In certain embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) may be adjusted once in a period of time. In certain embodiments, the period of time is from about one week to about eight weeks, such as from about two weeks to about seven weeks, about three weeks to about six weeks, or about four weeks. In certain specific embodiments, the compound is administered in a formulation as described in Section 5.3.

In certain embodiments, the daily dose of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) is not increased if the level of hemoglobin has increased by more than 1.2 g/dL relative to a baseline hemoglobin level. In certain specific embodiments, the compound is administered in a formulation as described in Section 5.3.

5.7.5 Dosing and Methods for Treating Anemia

In certain embodiments, provided herein are methods for treating anemia, such as anemia secondary to non-dialysis dependent chronic kidney disease, comprising administering to a patient having anemia a daily dose of a compound which is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid); measuring the hemoglobin level in the patient after an administration of the daily dose of the compound and then again a period of time later, wherein when the hemoglobin level in the patient is less than about 10.0 g/dL and the level of hemoglobin has decreased by less than about 0.5 g/dL as compared to the level measured the period of time earlier; or when the hemoglobin level in the patient is less than about 10.0 g/dL and the level of hemoglobin has changed by up to about 0.4 g/dL as compared to the level measured the period of time earlier; or when the hemoglobin level in the patient is between about 10.0 and about 10.9 g/dL and the level of hemoglobin has decreased by less than about 0.5 g/dL as compared to the level measured the period of time earlier; administering an adjusted daily dose of the compound that is about 150 mg greater than the daily dose. In certain such embodiments, the compound is administered once daily and may be administered orally. In certain embodiments, the daily dose is about 450 mg, such that when the daily dose is increased by about 150 mg, the adjusted daily dose is about 600 mg. In certain embodiments, the period of time is from about one week to about eight weeks, such as from about two weeks to about seven weeks, about three weeks to about six weeks, or about four weeks. In certain embodiments, the daily dose may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose may be increased or decreased by an amount between about 75 mg and about 250 mg, about 100 mg and about 225 mg, or about 125 mg and about 200 mg. In certain embodiments, the adjusted daily dose does not exceed 600 mg or 750 mg. In certain specific embodiments, the dose is administered in a formulation as described in Section 5.3.

In certain embodiments, provided herein are methods for treating anemia, such as anemia secondary to non-dialysis dependent chronic kidney disease, comprising administering to a patient having anemia a daily dose of a compound which is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid); measuring the hemoglobin level in the patient after an administration of the daily dose of the compound and then again a period of time later, wherein when the hemoglobin level in the patient is less than about 10.0 g/dL and the level of hemoglobin has increased by greater than about 1.5 g/dL as compared to the level measured the period of time earlier; or when the hemoglobin level in the patient is between about 10.0 and about 10.9 g/dL and the level of hemoglobin has increased by greater than about 1.5 g/dL as compared to the level measured the period of time earlier; or when the hemoglobin level in the patient is between about 11.0 and about 12.2 g/dL and the level of hemoglobin has increased by between about 1.0 and about 1.4 g/dL as compared to the level measured the period of time earlier; or when the hemoglobin level in the patient is between about 12.3 and about 12.9 g/dL and the level of hemoglobin has decreased by up to about 0.4 g/dL or increased by up to about 0.4 g/dL as compared to the level measured the period of time earlier; or when the hemoglobin level in the patient is between about 12.3 and about 12.9 g/dL and the level of hemoglobin has increased by about 0.5 to about 0.9 g/dL as compared to the level measured the period of time earlier administering an adjusted daily dose of the compound that is 150 mg less than the daily dose. In certain such embodiments, the compound is administered once daily and may be administered orally. In certain embodiments, the daily dose is about 450 mg, such that when the daily dose is decreased by about 150 mg, the adjusted daily dose is about 300 mg. In certain embodiments, the period of time is from about one week to about eight weeks, such as from about two weeks to about seven weeks, about three weeks to about six weeks, or about four weeks. In certain embodiments, the daily dose may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose may be increased or decreased by an amount between about 75 mg and about 250 mg, about 100 mg and about 225 mg, or about 125 mg and about 200 mg. In certain embodiments, the adjusted daily dose does not exceed 600 mg or 750 mg. In certain specific embodiments, the dose is administered in a formulation as described in Section 5.3.

In certain embodiments, provided herein are methods of treating anemia, such as anemia secondary to non-dialysis dependent chronic kidney disease, comprising administering to a patient having anemia a daily dose of a compound which is a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid); measuring the hemoglobin level in the patient after an administration of the daily dose of the compound and then again a period of time later, wherein when the hemoglobin level in the patient is between about 11.0 and about 12.2 g/dL and the level of hemoglobin has increased by greater than about 1.5 g/dL as compared to the level measured the period of time earlier; or when the hemoglobin level in the patient is between about 12.3 and about 12.9 g/dL and the level of hemoglobin has increased by between about 1.0 and about 1.4 g/dL as compared to the level measured the period of time earlier; or when the hemoglobin level in the patient is between about 12.3 and about 12.9 g/dL and the level of hemoglobin has increased by greater than about 1.5 g/dL as compared to the level measured the period of time earlier administering an adjusted daily dose of the compound that is about 300 mg less than the daily dose. In certain embodiments, the compound is administered once daily and may be administered orally. In certain embodiments, the daily dose is 450 mg, such that when the initial daily dose is decreased by about 300 mg, the adjusted daily dose is about 150 mg. In certain embodiments, the period of time is from about one week to about eight weeks, such as from about two weeks to about seven weeks, about three weeks to about six weeks, or about four weeks. In certain embodiments, the daily dose may be increased or decreased by about 75 mg, about 100 mg, about 125 mg, about 150 mg, about 175 mg, about 200 mg, about 225 mg, about 250 mg, about 275 mg, or about 300 mg. In certain embodiments, the daily dose may be increased or decreased by an amount between about 75 mg and 300 mg, about 100 mg and about 300 mg, about 125 mg and about 300 mg, about 150 mg and about 300 mg, about 175 mg and about 300 mg, about 200 mg and about 300 mg, about 225 mg and about 300 mg, about 250 mg and about 300 mg, or about 275 mg and about 300 mg. In certain embodiments, the daily dose may be increased or decreased by an amount between about 75 mg and about 250 mg, about 100 mg and about 225 mg, or about 125 mg and about 200 mg. In certain embodiments, the adjusted daily dose does not exceed 600 mg or 750 mg. In certain specific embodiments, the dose is administered in a formulation as described in Section 5.3.

In certain embodiments, provided herein are methods for treating anemia related to CKD in a patient as described in Section 5.4 undergoing hemodialysis, wherein said method comprises administering to the patient a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 at about 8 hours, 7 hours, 6 hours, 5 hours, 4 hours, 3 hours, 2 hours, or 1 hour, or at about between 7 hours to 8 hours, 6 hours to 7 hours, 5 hours to 6 hours, 4 hours to 5 hours, 3 hours to 4 hours, 2 hours to 3 hours, 1 hour to 2 hours, or up to about 1 hour prior to starting a hemodialysis session. In certain specific embodiments, the compound is administered in a formulation as described in Section 5.3.

In certain embodiments, provided herein are methods for treating anemia related to CKD in a patient as described in Section 5.4 undergoing hemodialysis, wherein said method comprises administering to the patient a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 twice per week, three times per week, four times per week, five times per week, six times per week, every day, once every two weeks, once every three weeks, once every four weeks, or once every two months, or once every three months. In certain specific embodiments, the compound is administered in a formulation as described in Section 5.3.

In certain embodiments, provided herein are methods for treating anemia related to CKD in a patient as described in Section 5.4 undergoing hemodialysis, wherein said method comprises administering to the patient a pharmaceutically effective amount of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 at about 8 hours, 7 hours, 6 hours, 5 hours, 4 hours, 3 hours, 2 hours, or 1 hour, or at about between 7 hours to 8 hours, 6 hours to 7 hours, 5 hours to 6 hours, 4 hours to 5 hours, 3 hours to 4 hours, 2 hours to 3 hours, 1 hour to 2 hours, or up to about 1 hour after completing a hemodialysis session. In certain specific embodiments, the compound is administered in a formulation as described in Section 5.3.

In certain embodiments, a method provided herein further comprises a monitoring step wherein the serum concentration of a metabolite of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 is determined. In more specific embodiments, the serum concentration of the phenolic-glucuronide and/or the acyl-glucuronide of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 is determined. In even more specific embodiments, the serum concentration of the phenolic-glucuronide and/or the acyl-glucuronide of Compound 1, i.e., Metabolite 1 or Metabolite 2 is determined. In certain even more specific embodiments, the daily dose is adjusted in accordance with the serum concentration of the metabolite. In certain specific embodiments, the dose is administered in a formulation as described in Section 5.3.

5.8 Combination Therapy

In certain embodiments, provided herein are methods for treating anemia, such as anemia secondary to chronic kidney disease, in a patient as described in Section 5.4 comprising administering a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) in a formulation described herein in Section 5.3 in combination with another medicament. Such combination therapy may be achieved by way of the simultaneous, sequential, or separate dosing of the individual components of the treatment. Additionally, when administered as a component of such combination therapy, the compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) in a formulation described herein in Section 5.3 and the other medicament may be synergistic, such that the daily dose of either or both of the components may be reduced as compared to the dose of either component that would normally be given as a monotherapy. Alternatively, when administered as a component of such combination therapy, the compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) in a formulation described herein in Section 5.3 and the other medicament may be additive, such that the daily dose of each of the components is similar or the same as the dose of either component that would normally be given as a monotherapy.

In certain embodiments, provided herein are methods for treating in a patient as described in Section 5.4, non-severe anemia secondary to chronic kidney disease, secondary to non-dialysis dependent chronic kidney disease, non-severe anemia secondary to congestive heart failure, and idiopathic anemia of aging, comprising administering to a patient having anemia daily dose a HIF prolyl hydroxylase inhibitor or a HIF-alpha stabilizer, such as a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, compound disclosed herein, such as Compound 1) in a formulation described herein in Section 5.3, wherein the compound is administered continuously and/or indefinitely, and wherein the compound is administered with another medicament.

In certain embodiments, provided herein are methods for treating in a patient as described in Section 5.4, anemia, such as anemia secondary to chronic kidney disease, comprising administering a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) in a formulation described herein in Section 5.3 to a patient having anemia, wherein the compound is optionally administered in combination with an iron supplement, such as ferrous sulfate, ferrous gluconate, or ferrous fumarate. In certain such embodiments, the iron supplement is administered at least one hour, at least two hours, at least three hours, at least four hours, or even at least six hours following administration of the compound. In certain embodiments, the iron supplement is administered in an amount such that ferritin is maintained at a level of between about 50 ng/mL and about 300 ng/mL. In certain embodiments, the iron supplement is administered orally at a daily dose of at least about 50 mg of elemental iron. In certain embodiments, the iron supplement is administered orally at a dose of about 50 mg of elemental iron. In certain embodiments, the iron supplement is administered intravenously. In certain embodiments, the iron supplement is administered continuously and/or indefinitely, such as for more than 42 consecutive days. In certain alternative embodiments, the iron supplement is administered on an as needed basis such that ferritin is maintained at a level of between about 50 ng/mL and about 300 ng/mL. In certain such embodiments, the daily dose of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) in a formulation described herein in Section 5.3. In certain such embodiments, the daily dose is about 150 mg, about 300 mg, about 450 mg, or about 600 mg. Such daily doses may be administered orally, once daily, twice daily, or three times daily, preferably once daily.

In certain embodiments, provided herein are methods for treating in a patient as described in Section 5.4, anemia, such as anemia secondary to chronic kidney disease, comprising administering a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) in a formulation described herein in Section 5.3 to a patient as described in Section 5.4 having anemia, wherein the compound is optionally administered in combination with an erythropoiesis stimulating agent (ESA), such as an erythropoietin mimetic. In certain such embodiments, the ESA is an rhEPO product, including, but not limited to, epoetin alfa, epoetin beta, darbepoetin, or peginesatide. In certain such embodiments, the ESA is administered as a rescue therapy. In certain alternative embodiments, the ESA is administered continuously and/or indefinitely, such as for more than 42 consecutive days. In certain such embodiments, the daily dose is of the compound is about 150 mg, about 300 mg, about 450 mg, about 600 mg, or about 750 mg of a compound having a structure of Formula (I), Formula (II), Formula (III), Formula (IV), or of Formula (V), or a compound selected from Compound 1, Compound 2, Compound 3, Compound 4, Compound 5, Compound 6, Compound 7, Compound 8, Compound 9, Compound 10, Compound 11, Compound 12, Compound 13, Metabolite 1, or Metabolite 2 or a pharmaceutically acceptable salt, solvate, or hydrate thereof (specifically, {[5-(3-chlorophenyl)-3-hydroxypyridine-2-carbonyl]amino}acetic acid or 2-(5-(3-fluorophenyl)-3-hydroxypicolinamido)acetic acid) in a formulation described herein in Section 5.3. In certain such embodiments, the daily dose is about 150 mg, about 300 mg, about 450 mg, or about 600 mg. Such daily doses may be administered orally, once daily, twice daily, or three times daily, preferably once daily.

6 EXAMPLES

6.1 Example 1: Compound 1 for the Correction of Anemia in Subjects with Non-Dialysis-Dependent Chronic Kidney Disease This example describes a phase 3, randomized, open-label, active-controlled study to evaluate the efficacy and safety of oral Compound 1 for the correction of anemia in subjects with Non-Dialysis-Dependent Chronic Kidney Disease (NDD-CKD) in approximately 1000 subjects. Efficacy and safety of Compound 1 is compared to darbepoetin alfa for the correction and maintenance of Hgb in subjects with anemia secondary NDD-CKD.

The study population consists of subjects ≥18 years of age with NDD-CKD, estimated glomerular filtration rate (eGFR) ≤60 mL/min/1.73 m$^2$, and hemoglobin (Hgb) <10.0 g/dL, who are not being treated with an erythropoiesis-stimulating agent (ESA).

Following a screening period of up to 4 weeks, subjects who meet all inclusion and no exclusion criteria described below are randomized 1:1 to Compound 1 or darbepoetin alfa. Randomization is stratified by Geographic region (United States [US] vs. European Union [EU] vs. Rest of World [ROW]).
New York Heart Association congestive heart failure (CHF) Class 0 or I vs II or III.
Study entry Hgb (<9.5 vs ≥9.5 g/dL).

Following randomization, there are 4 periods during the study:

Correction Period (Weeks 0-23): initial period on study treatment for the correction of Hgb.
Maintenance Period (Weeks 24-52): period on study treatment during which efficacy is assessed (primary evaluation period: Weeks 24-36; secondary evaluation period: Weeks 40-52).
Long-term Treatment Period (Weeks 53-End of Treatment) continued study treatment to assess long-term safety.
Follow-up Period (End of Treatment+4 weeks): post-treatment visit (either in person or via telephone) for safety.

Estimated time to full enrollment of approximately 1000 randomized subjects is 20 months, and average follow-up duration is expected to be 1.8 years. All subjects remain in the study until approximately 631 major adverse cardiovascular events (MACE) occur across 2 separate NDD-CKD studies, at which time subjects are scheduled for a final visit and the study is closed. Sites are notified of the global study end date approximately 3 months prior to study closure (based on accrual of MACE across the 2 studies) and inform active subjects of the global study end date thereafter.

Selection and Withdrawal of Subjects

Subjects are selected for the study based on the following inclusion and exclusion criteria.

Inclusion Criteria.

Subjects must meet all of the following inclusion criteria to be eligible:

1. Over 18 years of age, inclusive;
2. Diagnosis of Chronic Kidney Disease with an estimated glomerular filtration rate (eGFR) ≤60 mL/minute/1.73 m$^2$ at the Screening visit, using the 2009 Chronic Kidney Disease Epidemiology Collaboration (CKD-EPI) creatinine equation at screening and not expected to start dialysis within 6 months of screening;
3. Mean screening Hgb <10.0 g/dL as determined by the average of 2 Hgb values measured by the central laboratory during screening;
4. Serum Ferritin ≥100 ng/mL with transferrin saturation (TSAT) ≥20% during screening;
5. Folate and vitamin $B_{12}$ measurement ≥lower limit of normal during screening;
6. Understands the procedures and requirements of the study and provides written informed consent and authorization for protected health information disclosure.

Exclusion Criteria.

Subjects presenting with any of the following do not qualify for entry into the study:

1. Anemia due to a cause other than CKD or subjects with active bleeding or recent blood loss;
2. Subjects with sickle cell disease, myelodysplastic syndromes, bone marrow fibrosis, hematologic malignancy, myeloma, hemolytic anemia, thalassemia, or pure red cell aplasia;
3. Red blood cell (RBC) transfusion within 4 weeks prior to or during screening.
4. Intravenous (IV) iron within 4 weeks prior to screening;
5. Any ESA (e.g., recombinant human erythropoietin [rhEPO] or darbepoetin alfa) within 6 weeks prior to screening;
6. Aspartate aminotransferase (AST)/serum glutamic oxaloacetic transaminase (SGOT), alanine aminotransferase (ALT)/serum glutamic pyruvic transaminase (SGPT), or total bilirubin >2.0×upper limit of normal (ULN) at screening. Subjects with a history of Gilbert's syndrome are not excluded;
7. Uncontrolled hypertension (confirmed diastolic blood pressure >110 mmHg or systolic blood pressure >180 mmHg) at screening;
8. Severe heart failure at screening (New York Heart Association Class IV);
9. Acute coronary syndrome (hospitalization for unstable angina or myocardial infarction), urgent coronary revascularization, hospitalization for CHF, or stroke within 12 weeks prior to screening;
10. History of active malignancy within 2 years prior to screening, except for curatively resected basal cell carcinoma of skin, squamous cell carcinoma of skin, cervical carcinoma in situ, or resected benign colonic polyps;
11. History of deep vein thrombosis (DVT) or pulmonary embolism (PE) requiring active treatment within 8 weeks prior to screening;
12. History of hemosiderosis or hemochromatosis;

13. History of prior organ transplantation or scheduled organ transplant (subjects on kidney transplant wait-list are not excluded), or prior stem cell or bone marrow transplant (corneal transplants are not excluded);
14. Use of an investigational medication or participation in an investigational study within 30 days or 5 half-lives of the investigational medication (whichever is longer), prior to the screening visit;
15. Previous participation in this study, receipt of Compound 1 in another study, or previous participation in a study with another hypoxia-inducible factor prolyl hydroxylase inhibitor (HIF PHI);
16. Females who are pregnant or breast-feeding. Women of childbearing potential who are unable or unwilling to use an acceptable method of contraception;
17. Non-vasectomized male subjects who are unable or unwilling to use an acceptable method of contraception;
18. Any other reason that in the opinion of the investigator would make the subject not suitable for participation in the study.

Efficacy Endpoints
Efficacy endpoints for this study are defined as follows:
Primary
Mean change in Hgb between baseline (mean pretreatment Hgb) and the primary evaluation period (mean Hgb from weeks 24-36).
Key Secondary
Mean change in Hgb between baseline (mean pretreatment Hgb) and the primary evaluation period (mean Hgb from Weeks 24-36);
Proportion of subjects with mean Hgb between 10.0 and 12.0 g/dL (inclusive) during the primary evaluation period (weeks 24-36);
Mean weekly dose of intravenous (IV) elemental iron administered from baseline to Week 52;
Proportion of subjects receiving RBC transfusion(s) from baseline to Week 52.
Other Secondary
Progression of CKD based on change in GFR;
Proportion of Hgb values within the target range during the maintenance period (Weeks 24-52);
Hgb increase of >1.0 g/dL from baseline;
Confirmed Hgb values <10.0 or >12.0 g/dL;
ESA rescue;
Dose adjustments;
Maintenance of iron sufficiency (defined as ferritin ≥100 ng/mL and TSAT ≥20%);
Receiving IV iron therapy.
Safety Endpoints
Safety endpoints for this study are defined as follows:
MACE, defined as all-cause mortality, non-fatal myocardial infarction, or non-fatal stroke;
Individual components of MACE;
  all-cause mortality;
  non-fatal myocardial infarction;
  non-fatal stroke;
Thromboembolic events: arterial thrombosis, DVT, PE, or vascular access thrombosis;
Hgb >12.0 g/dL, >13.0 g/dL, or >14.0 g/dL;
Hgb increase >1.0 g/dL within any 2-week interval or >2.0 g/dL within any 4-week interval;
Adverse events (AEs) and serious adverse events (SAEs);
Vital signs and clinical laboratory values.
Treatment of Subjects
Subjects are randomized 1:1 to either
Compound 1 starting dose: 2 tablets once daily (300 mg/day); or
Darbepoetin alfa (SC) starting dose: based on the approved local product label
Dose Adjustment Guidelines—all Treatment Groups
Dosing is initiated at the baseline visit, and the first dose of study medication (Compound 1 or darbepoetin alfa) is administered at the investigative site after other baseline procedures have been completed. Hemoglobin is monitored via HemoCue® point of care device throughout the study to determine if the dose of study medication (Compound 1 or darbepoetin alfa) will be adjusted or suspended. From Weeks 0 to 12, Hgb is measured via HemoCue® every 2 weeks for monitoring for dose adjustment. From Week 12 to Week 52, Hgb is monitored via HemoCue® every 4 weeks. From Week 53 through the end of the study, Hgb is continued to be monitored via HemoCue® to determine if the dose of study medication will be adjusted or suspended. Hemoglobin is also assessed with a complete blood count (CBC) through the central laboratory for efficacy and safety evaluations; however, dose adjustments should be based on the local HemoCue® Hgb value.

The aim is to increase and maintain a Hgb level of 10-11 g/dL in the US, and 10-12 g/dL outside the US throughout the study.

Adjustments to doses are guided by an interactive web response (IWR) system based on Hgb concentration and programmed Dose Adjustment Algorithms. The programmed Dose Adjustment Algorithm for Compound 1 follows the Dose Adjustment Guidelines (see below). The programmed Dose Adjustment Algorithm for darbepoetin alfa is based on the local product label.

When adjusting therapy, Hgb rate of rise, rate of decline, and variability as well as the subject's clinical condition (i.e., recent illness, volume depletion, volume overload, etc) are considered. In cases of extenuating clinical circumstances, the Investigator may elect to dose outside the IWR system dosing recommendation to maintain the Hgb within the target range. In such cases, the clinical circumstances must be documented in the subject's record and collected in the case report form (CRF)

Correction Period (Weeks 0-23)
Compound 1 is dosed according to the following dose-adjustment algorithm guidelines:
Dose Adjustment algorithm for US:
Do not increase the dose more frequently than once every 4 weeks. Decreases in dose can occur more frequently. Avoid frequent dose adjustments.
If the Hgb has not increased by more than 0.5 g/dL above the baseline value after 4 weeks, increase the Compound 1 dose by 1 tablet per day. Increase dose by 1 tablet every 4 weeks until Hgb is above 10.0 g/dL (maximum daily dose of Compound 1 is 600 mg/day [4 tablets]).
If the Hgb rises rapidly (e.g., more than 1 g/dL in any 2-week period), reduce the dose of Compound 1 by 1 tablet per day.
If the Hgb falls below 10.0 g/dL, increase the dose of Compound 1 by 1 tablet per day.
If the Hgb level exceeds 11.0 g/dL, interrupt Compound 1 until Hgb decreases to 10.5 g/dL or less, then resume dosing of Compound 1 with 1 fewer tablet per day.
If a dose adjustment is required to maintain Hgb at the desired level, the Compound 1 dose is adjusted by 1 tablet per day.
Dose Adjustment algorithm for Ex-US:
Do not increase the dose more frequently than once every 4 weeks. Decreases in dose can occur more frequently. Avoid frequent dose adjustments.

If the Hgb has not increased by more than 0.5 g/dL above the baseline value after 4 weeks, increase the Compound 1 dose by 1 tablet per day. Increase dose by 1 tablet per day every 4 weeks until Hgb is above 10.0 g/dL (maximum daily dose of Compound 1 is 600 mg/day [4 tablets]).

If the Hgb rises rapidly (e.g., more than 1 g/dL in any 2-week period), reduce the dose of Compound 1 by 1 tablet per day.

If the Hgb falls below 10.0 g/dL, increase the dose of Compound 1 by 1 tablet per day.

If the Hgb level exceeds 12.0 g/dL, reduce the dose of Compound 1 by 1 tablet per day. If the Hgb level exceeds 13.0 g/dL, interrupt Compound 1 until Hgb decreases to 12.5 g/dL or below, then resume dosing of Compound 1 with 1 fewer tablet per day.

If a dose adjustment is required to maintain Hgb at the desired level, the Compound 1 dose is adjusted by 1 tablet per day.

Subjects who are randomized to receive darbepoetin alfa are dosed using an IWR system implementing a Dose Adjustment Algorithm based on the approved darbepoetin alfa local product label. Darbepoetin alfa dosing is independent of the visit schedule, and the dosing schedule may shift per local standard of care and country-specific darbepoetin dosing guidelines.

Maintenance Period (Weeks 24-52) and Long-Term Treatment Period (Weeks 53 EOT):

Compound 1 should continue to be dosed according to the dose adjustment algorithm guidelines as described above.

Following the Correction Period, subsequent darbepoetin alfa doses may be adjusted in individual subjects based on the approved darbepoetin alfa local product label specific for maintenance of treatment. Local standard of care and regional/national guidelines should be taken into consideration for treatment.

Dosing Instructions
Compound 1

All subjects start with 2 tablets daily (300 mg/day). Dose levels of Compound 1 include 150, 300, 450, and 600 mg (available tablet strength is 150 mg). Each subject takes his/her first dose of study medication at the investigative site at the baseline visit. Thereafter, study medication is taken once daily on an outpatient basis. Subjects may take Compound 1 with or without food. The dose should be taken at approximately the same time each day, preferably between 7 AM and 2 PM. The subject should be instructed to take any oral iron supplements at least 2 hours before or 2 hours after the dose of Compound 1.

Darbepoetin Alfa

Darbepoetin alfa is administered, stored, and dispensed according to the approved local product label.

Iron Supplementation

Investigators should prescribe iron supplementation as needed during the study to maintain ferritin ≥100 ng/mL and TSAT ≥20%. In general, only oral iron should be used for therapy. Intravenous iron use is restricted and should only be administered to subjects who have documented intolerance to oral iron and iron deficiency (e.g., ferritin <100 ng/mL and/or TSAT <20%). Discontinuation of IV iron is required once the subject is no longer iron deficient (ferritin ≥100 ng/mL and TSAT ≥20%). Important: Because of the potential for oral iron to reduce the bioavailability of Compound 1, the study medication should not be administered concurrently with an oral iron supplement (including multivitamins containing iron). The subject should be instructed to take any oral iron supplements at least 2 hours before or 2 hours after the dose of Compound 1.

Rescue Therapy Guidelines

To ensure the safety of study subjects and to standardize the use of rescue in the study, the following rescue therapy guidelines are provided:

1. ESA Rescue: Starting at Week 6, subjects in both treatment arms are allowed (although are not required) to have their Hgb rescued with ESA therapy, per the local standard of care. When possible, a subject on Compound 1 should be on the maximum dose of Compound 1 for 2 weeks prior to ESA rescue. A subject on darbepoetin alfa may rescue with another ESA per the standard of care. To qualify for ESA rescue, a subject must fulfill ALL of the following:

The subject has experienced a clinically significant worsening of their anemia or symptoms of anemia (e.g., fatigue, weakness, shortness of breath, chest pain, confusion, or dizziness) compared to baseline;

The subject's Hgb is <9.0 g/dL; and

Reducing the risk of alloimmunization and/or other RBC transfusion related risks is a goal.

ESA rescue therapy should be administered per the local institution's guidelines and per the package insert or SmPC. While receiving ESA rescue therapy, subjects must discontinue taking study medication. Hemoglobin monitoring are performed per the criteria in the "Dosage and Regimens" section of the trial protocol. ESA rescue treatment should be stopped when Hgb is ≥9 g/dL. Treatment with study medication should be resumed after the following intervals:

2 days after last dose of epoetin rescue;

7 days after last dose of darbepoetin alfa rescue;

14 days after last dose of methoxy polyethylene glycol-epoetin beta rescue.

Following ESA rescue, the study medication should be resumed at the same dose as previously used and adjusted according to the Dose Adjustment Guidelines ("Dosage and Regimens" section).

2. RBC Transfusion: Investigators should use their local institution's transfusion guidelines when determining whether to transfuse a study subject. In general, in the event of an acute or severe loss of blood, a RBC transfusion should be administered as clinically indicated. In less severe instances but where there may be worsening of anemia or moderate to severe symptoms of anemia, RBC transfusions are permitted at the discretion of the Investigator given the medical necessity. Study medication (Compound 1 or darbepoetin alfa) may be continued during the transfusion period.

6.2 Example 2: Compound 1 for the Maintenance Treatment of Anemia in Subjects with Non-Dialysis-Dependent Chronic Kidney Disease This example describes a phase 3, randomized, open-label, active-controlled study to evaluate the efficacy and safety of oral Compound 1 for the maintenance treatment of anemia in subjects with Non-Dialysis-Dependent Chronic Kidney Disease (NDD-CKD) in approximately 2100 subjects. Efficacy and safety of Compound 1 is compared with darbepoetin alfa for the maintenance treatment of anemia in subjects with NDD-CKD after conversion from current ESA therapy.

The study population consists of subjects ≥18 years of age with NDD-CKD, estimated glomerular filtration rate (eGFR) ≤60 mL/min/1.73 m$^2$, and hemoglobin (Hgb) between 8.0 and 11.0 g/dL (inclusive) in the United States (US), and between 9.0 and 12.0 g/dL (inclusive) outside of the US, who are currently treated with an erythropoiesis stimulating agent (ESA) for anemia.

Following a screening period of up to 4 weeks, subjects who meet all inclusion and no exclusion criteria described below are randomized 1:1 to Compound 1 or darbepoetin alfa.

Randomization is stratified by
Geographic region (United States [US] vs. European Union [EU] vs. Rest of World [ROW]).
New York Heart Association congestive heart failure (CHF) Class 0 or I vs II or III.
Study entry Hgb (<10.0 vs ≥10.0 g/dL).

Following randomization, there are 3 periods during the study:
Conversion and Maintenance Period (Weeks 24-52): conversion to study treatment for maintaining Hgb (Weeks 0 23), primary efficacy evaluation (Weeks 24 36), and secondary efficacy evaluation (Weeks 40 52).
Long-term Treatment Period (Weeks 53-End of Treatment) continued study treatment to assess long-term safety.
Follow-up Period (End of Treatment+4 weeks): post-treatment visit (either in person or via telephone) for safety.

Estimated time to full enrollment of approximately 2100 randomized subjects is 20 months, and average follow-up duration is expected to be 1.8 years. All subjects remain in the study until approximately 631 major adverse cardiovascular events (MACE) occur across 2 separate NDD CKD studies, at which time subjects are scheduled for a final visit and the study is closed. Sites are notified of the global study end date approximately 3 months prior to study closure (based on accrual of MACE across the 2 studies) and inform active subjects of the global study end date thereafter.

Selection and Withdrawal of Subjects
Subjects are selected for the study based on the following inclusion and exclusion criteria.

Inclusion Criteria.
Subjects must meet all of the following inclusion criteria to be eligible:
1. Over 18 years of age, inclusive;
2. Diagnosis of Chronic Kidney Disease with an estimated glomerular filtration rate (eGFR) ≤60 mL/minute/1.73 m² at the Screening visit, using the 2009 Chronic Kidney Disease Epidemiology Collaboration (CKD-EPI) creatinine equation at screening and not expected to start dialysis within 6 months of screening;
3. Currently maintained on ESA therapy, with the last dose received within 8 weeks prior to screening;
4. Mean Screening Hgb between 8.0 and 11.0 g/dL (inclusive) in the US and between 9.0 and 12.0 g/dL (inclusive) outside of the US, as determined by the average of 2 Hgb values measured by the central laboratory during screening;
5. Serum Ferritin ≥100 ng/mL with transferrin saturation (TSAT) ≥20% during screening;
6. Folate and vitamin $B_{12}$ measurement ≥lower limit of normal during screening;
7. Understands the procedures and requirements of the study and provides written informed consent and authorization for protected health information disclosure.

Exclusion Criteria.
Subjects presenting with any of the following do not qualify for entry into the study:
1. Anemia due to a cause other than CKD or subjects with active bleeding or recent blood loss;
2. Subjects with sickle cell disease, myelodysplastic syndromes, bone marrow fibrosis, hematologic malignancy, myeloma, hemolytic anemia, thalassemia, or pure red cell aplasia;
3. Red blood cell (RBC) transfusion within 4 weeks prior to or during screening.
4. Aspartate aminotransferase (AST)/serum glutamic oxaloacetic transaminase (SGOT), alanine aminotransferase (ALT)/serum glutamic pyruvic transaminase (SGPT), or total bilirubin >2.0×upper limit of normal (ULN) at screening. Subjects with a history of Gilbert's syndrome are not excluded;
5. Uncontrolled hypertension (confirmed diastolic blood pressure >110 mmHg or systolic blood pressure >180 mmHg) at screening;
6. Severe heart failure at screening (New York Heart Association Class IV);
7. Acute coronary syndrome (hospitalization for unstable angina or myocardial infarction), urgent coronary revascularization, hospitalization for CHF, or stroke within 12 weeks prior to screening;
8. History of active malignancy within 2 years prior to screening, except for curatively resected basal cell carcinoma of skin, squamous cell carcinoma of skin, cervical carcinoma in situ, or resected benign colonic polyps;
9. History of deep vein thrombosis (DVT) or pulmonary embolism (PE) requiring active treatment within 8 weeks prior to screening;
10. History of hemosiderosis or hemochromatosis;
11. History of prior organ transplantation or scheduled organ transplant (subjects on kidney transplant wait-list are not excluded), or prior stem cell or bone marrow transplant (corneal transplants are not excluded);
12. Use of an investigational medication or participation in an investigational study within 30 days or 5 half-lives of the investigational medication (whichever is longer), prior to the screening visit;
13. Previous participation in this study, receipt of Compound 1 in another study, or previous participation in a study with another hypoxia-inducible factor prolyl hydroxylase inhibitor (HIF PHI);
14. Females who are pregnant or breast-feeding. Women of childbearing potential who are unable or unwilling to use an acceptable method of contraception;
15. Non-vasectomized male subjects who are unable or unwilling to use an acceptable method of contraception;
16. Any other reason that in the opinion of the Investigator would make the subject not suitable for participation in the study.

Efficacy Endpoints
Efficacy endpoints for this study are defined as follows:
Primary
Mean change in Hgb between baseline (mean pretreatment Hgb) and the primary evaluation period (mean Hgb from weeks 24-36).
Key Secondary
Mean change in Hgb between baseline (mean pretreatment Hgb) and the primary evaluation period (mean Hgb from Weeks 24-36);
Proportion of subjects with mean Hgb between 10.0 and 12.0 g/dL (inclusive) during the primary evaluation period (weeks 24-36);
Mean weekly dose of intravenous (IV) elemental iron administered from baseline to Week 52;
Proportion of subjects receiving RBC transfusion(s) from baseline to Week 52.

Other Secondary
Progression of CKD based on change in GFR;
Proportion of Hgb values within the target range during the maintenance period (Weeks 24-52);
Confirmed Hgb values <10.0 or >12.0 g/dL;
ESA rescue;
Dose adjustments;
Maintenance of iron sufficiency (defined as ferritin ≥100 ng/mL and TSAT ≥20%);
Receiving IV iron therapy.
Safety Endpoints
Safety endpoints for this study are defined as follows:
MACE, defined as all-cause mortality, non-fatal myocardial infarction, or non-fatal stroke;
Individual components of MACE;
  all-cause mortality;
  non-fatal myocardial infarction;
  non-fatal stroke;
Thromboembolic events: arterial thrombosis, DVT, PE, or vascular access thrombosis;
Hgb >12.0 g/dL, >13.0 g/dL, or >14.0 g/dL;
Hgb increase >1.0 g/dL within any 2-week interval or >2.0 g/dL within any 4-week interval;
Adverse events (AEs) and serious adverse events (SAEs);
Vital signs and clinical laboratory values.
Treatment of Subjects
Subjects are randomized 1:1 to either
Compound 1 starting dose: 2 tablets once daily (300 mg/day); or
Darbepoetin alfa (SC) initial dose is as follows:
  For subjects already on darbepoetin, the initial dosing regimen in the study should be based on the prior dosing regimen.
  For subjects taking other ESAs, the initial dose of darbepoetin should be based on the approved local product label.
  For all subjects, it is recommended that no additional ESA doses be administered after Screening visit 2 (SV2) and prior to the Randomization visit.
    Dose Adjustment Guidelines—all Treatment Groups
    Dosing is initiated at the baseline visit, and the first dose of study medication (Compound 1 or darbepoetin alfa) is administered at the investigative site after other baseline procedures have been completed. For all subjects, it is recommended that no additional ESA doses be administered after SV2 and prior to the Randomization visit. Hemoglobin is monitored via HemoCue® point of care device throughout the study to determine if the dose of study medication (Compound 1 or darbepoetin alfa) will be adjusted or suspended. From Weeks 0 to 12, Hgb is measured via HemoCue® every 2 weeks for monitoring for dose adjustment. From Week 12 to Week 52, Hgb is monitored via HemoCue® every 4 weeks. From Week 53 through the end of the study, Hgb is continued to be monitored via HemoCue® to determine if the dose of study medication will be adjusted or suspended. Hemoglobin is also assessed with a complete blood count (CBC) through the central laboratory for efficacy and safety evaluations; however, dose adjustments should be based on the local HemoCue® Hgb value.
    The aim is to maintain a Hgb level of 10-11 g/dL in the US, and 10-12 g/dL outside the US throughout the study.
    Adjustments to doses are guided by an interactive web response (IWR) system based on Hgb concentration and programmed Dose Adjustment Algorithms. The programmed Dose Adjustment Algorithm for Compound 1 follows the Dose Adjustment Guidelines (see below). The programmed Dose Adjustment Algorithm for darbepoetin alfa is based on the local product label.
    When adjusting therapy, Hgb rate of rise, rate of decline, and variability as well as the subject's clinical condition (i.e., recent illness, volume depletion, volume overload, etc) are considered. In cases of extenuating clinical circumstances, the Investigator may elect to dose outside the IWR system dosing recommendation to maintain the Hgb within the target range. In such cases, the clinical circumstances must be documented in the subject's record and collected in the case report form (CRF)
    Compound 1 is dosed according to the following dose-adjustment algorithm guidelines:
    Dose Adjustment algorithm for US:
    Do not increase the dose more frequently than once every 4 weeks. Decreases in dose can occur more frequently. Avoid frequent dose adjustments.
    If a dose adjustment is required to maintain Hgb at the desired level, the Compound 1 dose is adjusted by 1 tablet per day (minimum dose of Compound 1 is 150 mg/day [1 tablet]; maximum daily dose of Compound 1 is 600 mg/day [4 tablets]).
    If the Hgb rises rapidly (e.g., >1 g/dL in any 2-week period), reduce the dose of Compound 1 by 1 tablet per day.
    If the Hgb falls below 10.0 g/dL, increase the dose of Compound 1 by 1 tablet per day.
    If the Hgb level exceeds 11.0 g/dL, interrupt Compound 1 until Hgb decreases to 10.5 g/dL or less, then resume dosing of Compound 1 with 1 fewer tablet per day.
    Dose Adjustment algorithm for Ex-US:
    Do not increase the dose more frequently than once every 4 weeks. Decreases in dose can occur more frequently. Avoid frequent dose adjustments.
    If a dose adjustment is required to maintain Hgb at the desired level, the Compound 1 dose is adjusted by 1 tablet per day (minimum daily dose of Compound 1 is 150 mg/day [1 tablet]; maximum daily dose of Compound 1 is 600 mg/day [4 tablets]).
    If the Hgb rises rapidly (e.g., more than 1 g/dL in any 2-week period), reduce the dose of Compound 1 by 1 tablet per day.
    If the Hgb falls below 10.0 g/dL, increase the dose of Compound 1 by 1 tablet per day.
    If the Hgb level exceeds 12.0 g/dL, reduce the dose of Compound 1 by 1 tablet per day. If the Hgb level exceeds 13.0 g/dL, interrupt Compound 1 until Hgb decreases to 12.5 g/dL or below, then resume dosing of Compound 1 with 1 fewer tablet per day.
    For subjects randomized to darbepoetin alfa, the initial dose is determined as follows:
      For subjects already on darbepoetin, the initial dosing regimen in the study should be based on the prior dosing regimen.
      For subjects taking other ESAs, the initial dose of darbepoetin should be based on the approved local product label.
    Following the dose conversion, darbepoetin alfa is dosed SC, with dose adjustments guided by an IWR system implementing a Dose Adjustment Algorithm based on the approved darbepoetin alfa local product label. Darbepoetin alfa dosing is independent of the visit schedule, and the dosing schedule may shift per local standard of care and country specific darbepoetin dosing guidelines.

Dosing Instructions

Compound 1

All subjects start with 2 tablets daily (300 mg/day). Dose levels of Compound 1 include 150, 300, 450, and 600 mg (available tablet strength is 150 mg). Each subject takes his/her first dose of study medication at the investigative site at the baseline visit. Thereafter, study medication is taken once daily on an outpatient basis. Subjects may take Compound 1 with or without food. The dose should be taken at approximately the same time each day, preferably between 7 AM and 2 PM. The subject should be instructed to take any oral iron supplements at least 2 hours before or 2 hours after the dose of Compound 1.

Darbepoetin Alfa

Darbepoetin alfa is administered, stored, and dispensed according to the approved local product label.

Iron Supplementation

Investigators should prescribe iron supplementation as needed during the study to maintain ferritin ≥100 ng/mL and TSAT ≥20%. In general, only oral iron should be used for therapy. Intravenous iron use is restricted and should only be administered to subjects who have documented intolerance to oral iron and iron deficiency (e.g., ferritin <100 ng/mL and/or TSAT <20%). Discontinuation of IV iron is required once the subject is no longer iron deficient (ferritin ≥100 ng/mL and TSAT ≥20%). Important: Because of the potential for oral iron to reduce the bioavailability of Compound 1, the study medication should not be administered concurrently with an oral iron supplement (including multivitamins containing iron). The subject should be instructed to take any oral iron supplements at least 2 hours before or 2 hours after the dose of Compound 1.

Rescue Therapy Guidelines

To ensure the safety of study subjects and to standardize the use of rescue in the study, the following rescue therapy guidelines are provided:

1. ESA Rescue: Starting at Week 6, subjects in both treatment arms are allowed (although will not be required) to have their Hgb rescued with ESA therapy, per the local standard of care. When possible, a subject on Compound 1 should be on the maximum dose of Compound 1 for 2 weeks prior to ESA rescue. A subject on darbepoetin alfa may rescue with another ESA per the standard of care. To qualify for ESA rescue, a subject must fulfill ALL of the following:

The subject has experienced a clinically significant worsening of their anemia or symptoms of anemia (e.g., fatigue, weakness, shortness of breath, chest pain, confusion, or dizziness) compared to baseline;

The subject's Hgb is <9.0 g/dL; and

Reducing the risk of alloimmunization and/or other RBC transfusion related risks is a goal.

ESA rescue therapy should be administered per the local institution's guidelines and per the package insert or SmPC. While receiving ESA rescue therapy, subjects must discontinue taking study medication. Hemoglobin monitoring will be performed per the criteria in the "Dosage and Regimens" section of the trial protocol. ESA rescue treatment should be stopped when Hgb is ≥9 g/dL. Treatment with study medication should be resumed after the following intervals:

2 days after last dose of epoetin rescue;

7 days after last dose of darbepoetin alfa rescue;

14 days after last dose of methoxy polyethylene glycol-epoetin beta rescue.

Following ESA rescue, the study medication should be resumed at the same dose as previously used and adjusted according to the Dose Adjustment Guidelines ("Dosage and Regimens" section).

2. RBC Transfusion: Investigators should use their local institution's transfusion guidelines when determining whether to transfuse a study subject. In general, in the event of an acute or severe loss of blood, a RBC transfusion should be administered as clinically indicated.

In less severe instances but where there may be worsening of anemia or moderate to severe symptoms of anemia, RBC transfusions are permitted at the discretion of the Investigator given the medical necessity. Study medication (Compound 1 or darbepoetin alfa) may be continued during the transfusion period.

6.3 Study Procedures, Schedules and Data Analysis for Examples 1 and 2

6.3.1 Statistical Considerations

Primary Efficacy Endpoint Analysis

The primary efficacy endpoint is defined as the mean Hgb change from baseline (mean pretreatment Hgb) to the mean Hgb from Weeks 24-36 (inclusive). The primary analysis uses an analysis of variance (ANOVA), stratified by the randomization strata with strata weighted by the stratum size. A 2-sided, 95% confidence interval is calculated for the difference between the Compound 1 group and control group. Noninferiority of Compound 1 is established if the lower limit of this confidence interval is ≥0.5 g/dL.

MACE Analysis

The MACE endpoint (adjudicated result) is analyzed as the time from first dose of study medication to first MACE. Subjects who have not experienced an adjudicated MACE by study closure are censored as of their last assessment time.

Major adverse cardiovascular events are analyzed using a stratified Cox proportional hazards model with a model containing treatment group. The randomization strata are used in this analysis. The primary MACE analysis takes place at study conclusion and is based upon all subjects in the safety population. The hazard ratio (Compound 1/control) is estimated, together with its 95% confidence interval. As this individual study has not been powered to provide a stand alone estimate of the hazard ratio for MACE, this interval is considered as descriptive. The time to first MACE is also graphically presented using Kaplan Meier curves.

The primary analysis for MACE is performed using the safety population. These analyses are repeated with censoring occurring 4 weeks following early discontinuation of study medication. An independent statistical analysis center performs analyses in support of the Independent Data Monitoring Committee (IDMC).

6.3.2 Study Procedures and Evaluations

Clinical Evaluations

The following clinical evaluations are conducted during the course of the study:

Medical history, demographic information, and physical examination (including height) are collected at SV2. After SV2, an abbreviated, symptom-directed physical examination should be performed at the discretion of the Investigator as clinically indicated. Vital signs including heart rate and blood pressure are collected at SV1, SV2, baseline, during study visits, and EOT, and should be taken prior to blood draws when possible. Weight is collected for all subjects at SV2, at Weeks 12, 24, 36, and 52, yearly thereafter, and at the EOT visit. For subjects on darbepoetin alfa, subjects are weighed for dosing per the local standard of care. 12-Lead electrocardiogram (ECG): is performed at baseline and are reviewed by the Investigator for the presence of rhythms of potential clinical concern. At each post-randomization study visit, the subject must specifically be questioned regarding the occurrence of any potential MACE endpoint event since the last study visit. Beginning with the first dose of study medication (Compound 1 or darbepoetin alfa) and through the global study end (Follow-up visit), the Investigator and study personnel review each subject's laboratory and clinical evaluation findings and query the subject directly regarding Adverse Events. All medications (both prescription and non prescription, and including vitamins, herbals, topicals, inhaled, and intranasal) taken within 30 days prior to the start of study medication (Compound 1 or darbepoetin alfa) and through the EOT visit should be recorded.

Laboratory Evaluations

The following laboratory evaluations are conducted during the course of the study: A serum pregnancy test is performed at SV2 for females of childbearing potential and must be available and must be negative before the subject takes the first dose of study medication. A CBC with differential is performed at baseline and twice annually at Weeks 28, 52, 76, 104, 128, 156, 180, 208. At all other noted visits, including SV1 and SV2, a CBC without differential is performed. The CBC with differential includes: Hgb, hematocrit, RBCs, mean corpuscular volume (MCV), mean corpuscular hemoglobin (MCH), mean corpuscular hemoglobin concentration (MCHC), red cell distribution width (RDW), white blood cell (WBC) count with differential (neutrophils, lymphocytes, monocytes, eosinophils, basophils), and platelets. Hemoglobin assessed by central laboratory CBC is used for evaluations of efficacy and safety, but should not be used for dose adjustments. Rather, Hgb levels assessed by HemoCue® should be used for dose adjustments.

For eligibility purposes for the study in Example 1, if Hgb at SV1 is 10.0-10.5 g/dL, 1 retest CBC should be performed prior to SV2. If retest Hgb is >10.0 g/dL, the subject should not proceed with SV2. If the Hgb at SV1 is >10.5 g/dL, the subject should not proceed with any further screening at this time.

For eligibility purposes for the study in Example 2, if Hgb at SV1 is 11.1-11.5 g/dL in the US or 12.1 12.5 g/dL outside of the US, 1 retest CBC should be performed prior to SV2. If retest Hgb is >11.0 g/dL in the US or >12.0 g/dL outside the US, the subject should not proceed with SV2. If the Hgb at SV1 is >11.5 g/dL in the US or >12.5 g/dL outside of the US, the subject should not proceed with any further screening at this time.

Using HemoCue®, Hgb is monitored throughout the study to determine if the dose of study medication (Compound 1 or darbepoetin alfa) are adjusted or suspended as described in the Dosing and Dose Adjustment Guidelines. An automated reticulocyte count (both absolute and percent) is performed at baseline and at Weeks 4, 12, 28, and 52. Blood samples are drawn at baseline to assess the prothrombin time (PT), partial thromboplastin time (PTT), and international normalized ratio (INR). A blood sample is drawn at SV2 to assess the folate and Vitamin B12 levels. A random urine spot sample should be collected at the investigative site during the baseline visit to provide the urine albumin to creatinine ratio (uACR). A blood sample for C-reactive protein is collected at the baseline visit.

Serum Chemistry: Blood samples to assess serum chemistry are collected at SV2 [Example 2 only], baseline, and twice annually at Weeks 28, 52, 76, 104, 128, 156, 180, 208. At all other noted visits: Serum creatinine and eGFR are performed. The serum chemistry includes the following assays: sodium, potassium, bicarbonate, chloride, calcium, magnesium, phosphorus, glucose, creatinine, blood urea nitrogen (BUN), creatine phosphokinase (CPK), uric acid, albumin, and total protein. Note: When a ≥50% decline in eGFR from the baseline value is observed, a repeat central laboratory measure should be performed within 30 to 60 days.

Blood samples to assess liver function are collected at SV2, baseline, every 4 weeks through Week 28, every 8 weeks from Week 28 to Week 52, and twice annually from Week 53 through the end of the study. Blood samples are also collected at the EOT visit. Liver function tests include: total bilirubin, alkaline phosphatase, ALT/SGPT, AST/SGOT, and lactate dehydrogenase (LDH).

Blood samples to assess the iron indices are collected at SV1, baseline, every 4 weeks through Week 12, every 8 weeks from Week 12 to Week 52, and every 12 weeks from Week 53 through the end of the study. Blood samples are also collected at the EOT visit. Assessments include the following indices: ferritin, iron, TIBC, and TSAT.

Blood samples are collected at the baseline, Week 28, and Week 52 visits to assess the cholesterol levels and are tested for the following types of lipids: total cholesterol, low-density lipoprotein (LDL), high-density lipoprotein (HDL), and triglycerides. Samples for biomarker analysis (hepcidin, vascular endothelial growth factor [VEGF]) are drawn at the baseline, Week 12, Week 28, and EOT visits. Blood samples for EPO analysis are obtained at baseline and at Weeks 4, 12, 28, and 52.

Plasma samples for PK evaluation are collected to analyze for both the parent compound (Compound 1) and its metabolites only. Collection time points for PK include Weeks 4, 12, 28, and 52.

Additional blood and urine samples are collected at baseline and Week 28 which may be used for exploratory measurement of biomarkers (e.g., factors relating to the activation of the HIF pathway). Subjects are also asked to provide optional consent to obtain and store a blood sample for future genetic analyses (e.g., DNA, mRNA).

For Example 2 only: An ACTH (cosyntropin) stimulation test is performed at baseline and at Weeks 12 and 52 (or at the EOT visit if the subject permanently discontinues study medication early prior to the Week 52 study visit) in a subset of 200 subjects in the EU. During the stimulation test, serum cortisol is measured prior to cosyntropin administration, and again 30 and 60 minutes after cosyntropin administration. Cosyntropin is administered 0.25 mg (full vial) IV push. Depending on the results of the test, early morning cortisol and ACTH measurements may be required to confirm the clinical significance of the results in individual subjects.

6.3.3 Schedule of Activities

Every effort should be made to adhere to this procedure schedule and all assessments should be completed at each study visit.

Pre-Screening Visit

To minimize Screen failures, there is an optional Pre-Screening visit which enables the subject to have a HemoCue® Hgb prior to proceeding with full Screening. For the study in Example 1, if the Pre-Screen HemoCue® Hgb is <10.0 g/dL, the investigative site may proceed with SV1, which preferably will occur on the same day as pre-screening. For the study in Example 2, if the Pre-Screen HemoCue® Hgb is between 8.0 and 11.0 g/dL (inclusive) in the US or between 9.0 and 12.0 g/dL (inclusive) outside the US, the investigative site may proceed with SV1, which preferably will occur on the same day as pre-screening.

Screening Visits

The screening period is a maximum of 28 days in duration. Two screening visits (SV1 and SV2) must be performed within 28 days prior to dosing (baseline visit or Day 1). There must be a minimum of 4 days between the 2 screening visits and a minimum of 4 days between SV2 and the baseline visit.

Screening Visit 1 (SV1):

At SV1, the following activities/procedures are performed:

Informed consent. For the study in Example 2: Also includes an additional optional consent for a substudy of adrenal function in a subset of 200 subjects in the EU.);

Review of eligibility criteria;

Vital signs including heart rate and blood pressure (assessed in seated position after 5 minutes of rest and prior to blood draws);

Laboratory procedures: CBC (without differential); Iron indices.

For the study in Example 1, if the Hgb at SV1 is 10.0-10.5 g/dL, 1 retest CBC should be performed prior to SV2. If the retest Hgb is >10.0 g/dL, the subject should not proceed with SV2. If the Hgb at SV1 is >10.5 g/dL, the subject should not proceed with any further Screening at this time.

For the study in Example 2, if the Hgb at SV1 is 11.1-11.5 g/dL in the US or 12.1 12.5 g/dL outside of the US, 1 retest CBC should be performed prior to SV2. If the retest Hgb is >11.0 g/dL in the US or >12.0 g/dL outside the US, the subject should not proceed with SV2. If the Hgb at SV1 is >11.5 g/dL in the US or >12.5 g/dL outside of the US, the subject should not proceed with any further screening at this time.

Screening Visit 2 (SV2):

At SV2, the following activities/procedures are performed:

Review of eligibility criteria;

Physical examination;

Demographics and medical history;

Vital signs including heart rate and blood pressure (assessed in seated position after 5 minutes of rest and prior to blood draws), as well as height and weight;

Laboratory procedures: Folate and vitamin B12 levels; CBC (without differential), Serum chemistry including serum creatinine and eGFR; Liver function tests; Serum pregnancy test for females of childbearing potential (eligible subjects will be advised to use an adequate contraceptive method);

Prior and current medication use.

For the study in Example 1, the mean of 2 Hgb values from the central laboratory must be <10.0 g/dL to qualify for inclusion into the trial. If the subject's Hgb does not qualify after SV1 and/or SV2+/−one retest Hgb, the subject should be considered a screen failure.

For the study in Example 2, the mean of 2 Hgb values from the central laboratory must be between 8.0 and 11.0 g/dL (inclusive) in the US or between 9.0 and 12.0 g/dL (inclusive) outside the US to qualify for inclusion into the trial. If the subject's Hgb does not qualify after SV1 and/or SV2+/−one retest Hgb, the subject should be considered a screen failure.

Subject Retesting

Subjects who initially fail to qualify for the study based on laboratory test results may be retested once within the 28 day Screening period, per Investigator discretion.

Subject Rescreening:

Subjects who fail to meet the qualifying criteria for Hgb or eGFR during the Screening period may be considered for rescreening at the discretion of the Investigator if it is felt that the subject's status has progressed and that the subject may now qualify for the study. Additionally, subjects who fail to qualify for the study based on low TSAT, ferritin, folate, or B12 values may be considered for rescreening after receiving replacement therapy. Screening is limited to 3 attempts (Screening and 2 additional rescreening attempts).

Baseline Visit (Day 1):

The baseline visit must be performed within 28 days of the 2 screening visits (SV1 and SV2) and a minimum of 4 days must elapse between the last Screening visit (SV2) and the baseline visit.

At the baseline visit, the following activities/procedures are performed:

Randomization;

12-lead ECG (prior to vital sign assessments and blood draws);

Vital signs including heart rate and blood pressure (assessed in seated position after 5 minutes of rest and prior to blood draws);

Laboratory Procedures: Random spot urine sample for uACR; Coagulation Tests; C-reactive protein; CBC (including differential); Reticulocyte count; Serum chemistry and eGFR; Liver function tests; Iron indices; Lipid profile; EPO; Biomarkers (hepcidin, VEGF); Exploratory samples; For the study in Example 2 only: ACTH (cosyntropin) stimulation test (for a subset of subjects in the EU)

Review of medical history for new conditions since screening visit;

Medication use since screening visit;

Study medication assessments and procedures:

Subject will take their first dose of study medication at the investigative site during the baseline visit;

Hgb by HemoCue® for dose initiation;

Compound 1 dispensing;

Darbepoetin alfa dispensing (per local product label);

Oral iron supplementation as needed to maintain ferritin ≥100 ng/mL and TSAT ≥20% (per local product label; see Section 8.4.6, Iron Supplementation);

AE assessment as needed (after receiving the first dose of study medication).

Year 1 Treatment Period Visits (Day 2 through Week 52):

During the Year 1 Treatment Period visits at Weeks 2, 4, 6, 8, 10, 12, 16, 20, 24, 28, 32, 36, 40, 44, 48, and 52, the following activities/procedures are performed:

Vital signs including heart rate and blood pressure (assessed in seated position after 5 minutes of rest and prior to blood draws);

Weight (Weeks 12, 24, 36, and 52);

Laboratory procedures: CBC (Weeks 2, 4, 6, 8, 10, 12, 16, 20, 24, 28, 32, 36, 40, 44, 48, and 52; differential at Weeks 28 and 52); Reticulocyte count (Weeks 4, 12, 28, and 52); Serum chemistry (Weeks 28 and 52); Serum creatinine and eGFR (Weeks 4, 8, 12, 20, 36, and 44; also at Weeks 28 and 52 as part of the serum chemistry); Liver function tests (Weeks 4, 8, 12, 16, 20, 24, 28, 36, 44, and 52); Iron indices (Weeks 4, 8, 12, 20, 28, 36, 44, and 52); Lipid profile (Weeks 28 and 52); EPO (Weeks 4, 12, 28, and 52); Biomarkers (Weeks 12 and 28); PK (Weeks 4, 12, 28, and 52; samples to be drawn only for subjects randomized to Compound 1); Exploratory samples (Week 28); For the study in Example 2 only: ACTH (cosyntropin) stimulation test (Weeks 12 and 52 for a subset of subjects in the EU);

Record date and time of subject's last dose of Compound 1 prior to the PK sample (Weeks 4, 12, 28, and 52);

Safety assessments: AE assessment; RBC transfusions and ESA rescue collection; Therapeutic phlebotomy collection; MACE endpoint questionnaire; Medication assessments and procedures: Review of concomitant medications; Hgb by HemoCue® for dose adjustment; Drug reconciliation—Study medication (Compound 1 or darbepoetin alfa) reconciliation will be conducted per the pharmacy manual instructions; Compound 1 dispensing as needed; Darbepoetin alfa dispensing (per local product label); Iron supplementation as needed to maintain ferritin ≥100 ng/mL and TSAT ≥20% (per local product label).

Year 2 Treatment Period Visits (Weeks 53 through 104)

During the Year 2 Treatment Period visits at Weeks 64, 76, 88, and 104, the following activities/procedures are performed:

Vital signs including heart rate and blood pressure (assessed in seated position after 5 minutes of rest and prior to blood draws);

Weight (Week 104);

Laboratory Procedures: CBC (Weeks 64, 76, 88, and 104; differential at Weeks 76 and 104); Serum chemistry including serum creatinine and eGFR (For the study in Example 1: Weeks 64, 76 and 104. For the study in Example 2: Weeks 76 and 104); Liver function tests (Weeks 76 and 104); Iron indices (Weeks 64, 76, 88, and 104);

Safety assessments: AE assessment; RBC transfusions and ESA rescue collection; Therapeutic phlebotomy collection; MACE endpoint questionnaire;

Medication assessments and procedures: Review of concomitant medications; Hgb by HemoCue® for dose adjustment; Drug reconciliation: Study medication (Compound 1 or darbepoetin alfa) reconciliation will be conducted per the pharmacy manual instructions; Compound 1 dispensing as needed; Darbepoetin alfa dispensing (per local product label); Iron supplementation to maintain ferritin ≥100 ng/mL and TSAT ≥20% (per local product label);

Year 3/4 Treatment Period Visits (Weeks 116 through 208)

During the Year 3/4 Treatment Period visits at Weeks 116, 128, 140, 156, 168, 180, 192, and 208, the following activities/procedures are performed:

Vital signs including heart rate and blood pressure (assessed in seated position after 5 minutes of rest and prior to blood draws);

Weight (Weeks 156 and 208);

Laboratory Procedures: CBC (Weeks 116, 128, 140, 156, 168, 180, 192, and 208; differential at Weeks 128, 156, 180, and 208); Serum chemistry including serum creatinine and eGFR (Weeks 128, 156, 180, and 208); Liver function tests (Weeks 128, 156, 180, and 208); Iron indices (Weeks 116, 128, 140, 156, 168, 180, 192, and 208);

Safety assessments: AE assessment; RBC transfusions and ESA rescue collection; Therapeutic phlebotomy collection; MACE endpoint questionnaire;

Medication assessments and procedures: Review of concomitant medications; Hgb by HemoCue® for dose adjustment; Drug reconciliation—Study medication (Compound 1 or darbepoetin alfa) reconciliation will be conducted per the pharmacy manual instructions; Compound 1 dispensing as needed; Darbepoetin alfa dispensing (per local product label); Iron supplementation to maintain ferritin ≥100 ng/mL and TSAT ≥20% (per local product label);

End of Treatment Visit

End of treatment evaluations are performed when the study is ended. Subjects who prematurely discontinue study medication for any reason should attend all subsequent protocol defined study visits and be continually monitored according to a Schedule of Activities for the duration of the study.

At the EOT visit, the following activities/procedures are performed:

Vital signs including heart rate and blood pressure (assessed in seated position after 5 minutes of rest and prior to blood draws), as well as weight;

Laboratory Procedures: CBC (without differential); Serum creatinine and eGFR; Liver function tests; Iron indices; Biomarkers (hepcidin, VEGF); For the study in Example 2 only: ACTH (cosyntropin) stimulation test (the test will only be performed at the EOT visit for subjects who are part of the adrenal function substudy and who have permanently discontinued study medication early prior to the Week 52 study visit);

Safety assessments: AE assessment; RBC transfusions and ESA rescue collection; Therapeutic phlebotomy collection; MACE endpoint questionnaire;

Recording of concomitant medications;

Drug reconciliation: Study medication (Compound 1 or darbepoetin alfa) reconciliation will be conducted per the pharmacy manual instructions;

Follow-Up Visit

The Follow-up visit will be conducted in person or via the telephone 4 weeks after the EOT visit. The following activities/procedures are performed:

AE assessment;

RBC transfusions and ESA rescue collection;

Therapeutic phlebotomy collection;

MACE endpoint questionnaire.

6.3.4 Data Analysis

Efficacy Analyses

The primary efficacy endpoint as well as all key and other secondary endpoints are summarized using descriptive statistics by treatment group, as well as by study visit and/or analysis period as appropriate. Mean values of Hgb as well as selected other efficacy parameters are plotted across study visits/periods by treatment group.

Analysis of Primary Efficacy Endpoint

The primary efficacy endpoint is defined as the mean Hgb change from baseline (mean pretreatment Hgb) to the mean Hgb from Weeks 24 36 (inclusive).

Primary Analysis of Primary Efficacy Endpoint

The primary analysis uses an analysis of variance (ANOVA) stratified by the randomization strata. Within this model the strata-specific differences between the treatments is combined using weights proportionate to the stratum size. A 2-sided 95% confidence interval for the difference between the Compound 1 group and the darbepoetin alfa group is obtained from this model. Noninferiority of Compound 1 to darbepoetin alfa is established by comparing the lower limit of the 95% confidence interval for the difference between treatment groups (Compound 1 minus darbepoetin alfa) obtained from this model to the noninferiority margin of −0.5 g/dL.

The primary analysis is performed using the full analysis population and the assigned treatment. All data collected during the study for subjects included in the full analysis population at the time of analysis, including data collected at any point after the initiation of rescue therapy as well as after early discontinuation of study medication treatment, is used for the primary analysis. Missing data is handled by using a return to baseline imputation (Example 1), or the Hgb data closest to the evaluation period (Example 2).

In geographies where regulatory approval does not require a formal analysis of MACE, efficacy and safety analyses may be performed upon the completion of 52 weeks of post randomization follow up in a sufficient number of subjects to support registration in that geography. Details are provided in a geography-specific SAP.

Analysis of Key Secondary Efficacy Endpoints

Secondary efficacy endpoints analyses are performed using the randomized and full analysis populations and the assigned treatment. Analysis for the key secondary efficacy endpoints are repeated using the PP population with the actual treatment received. In order to control the overall Type I error rate, hierarchical testing procedures are applied to the primary and secondary efficacy endpoints, and details are provided in the SAP.

Analysis of Mean Change in Hgb Value between baseline (Mean Pretreatment Hgb) and the Secondary Evaluation Period (Weeks 40-52): This endpoint is analyzed using the same methodology as specified for the primary efficacy endpoint, including the same method of imputation in absence of any measurements during the secondary evaluation period (Weeks 40 52). Sensitivity analyses similar to those of the primary efficacy endpoint are performed and details are provided in the SAP.

Analysis of Proportion of Subjects with Mean Hgb within the Target Range during the Primary Evaluation Period (Weeks 24-36): Each subject is classified using a binary variable ("yes"/"no") for the analysis of this endpoint. A classification of "yes" is assigned to any subject with a mean Hgb within the target range during the primary evaluation period (Weeks 24-36). All other subjects, including those with no available values during the primary evaluation period, are classified to the "no" category. The between-treatment difference is summarized with a confidence interval which uses Cochran Mantel Haenszel (CMH) weighting.

Analysis of Mean Weekly Dose of IV Elemental Iron Administered from baseline to Week 52: For each subject a mean weekly dose (mg) of IV elemental iron administered at any time starting on Day 1 through Week 52 is calculated based upon observed data. It is calculated as a total cumulative dose (mg) of IV elemental iron administered from Day 1 through Week 52 divided by the number of weeks the subject remained in the study up to the Week 52 visit. The between treatment difference is summarized with a confidence interval similar to those used for the primary endpoint.

Analysis of Proportion of Subjects Receiving RBC Transfusion(s) from baseline to Week 52: Each subject is classified using a binary variable ("yes"/"no") for the analysis of this endpoint. A classification of "yes" is assigned to any subject receiving RBC transfusion(s) at any time starting on Day 1 through Week 52. All other subjects are classified to the "no" category. The between-treatment difference is summarized with a confidence interval which uses CMH weighting. Time to first RBC transfusion is also summarized.

Analysis of Additional Secondary Efficacy Endpoints: Descriptive summaries of all secondary efficacy endpoints are presented using observed data without imputation. Analyses consist of the presentation of descriptive statistics by treatment group along with the presentation of 2-sided 95% confidence intervals for the treatment differences. The descriptive summaries of the secondary endpoints are made without stratification.

Safety Analyses

Analysis of MACE

The primary safety endpoint, time to the first adjudicated MACE, is analyzed as [date of the first MACE—the date of first dose of study medication]. A MACE is defined as all cause mortality, non-fatal myocardial infarction, or non-fatal stroke. Subjects who have not experienced a MACE by study closure are censored on the date of their last study assessment. The hazard ratio (Compound 1/darbepoetin alfa) and its 95% confidence interval are obtained from a stratified Cox proportional hazards model. As this study has not been designed to provide a standalone assessment of MACE, this analysis is considered a descriptive analysis. A similar analysis as described for the primary analysis of the MACE endpoint is performed with censoring of subjects 4 weeks following discontinuation of study treatment if they did not have a MACE prior to that time.

The primary MACE analysis is based upon all events that accrue over 2 separately planned NDD-CKD studies (Example 1 and Example 2).

Analysis of Adverse Events

Adverse events are summarized using the number and percentage of subjects with AEs for all subjects in the safety population. All AEs are coded using MedDRA. Treatment-emergent and post-treatment AEs are summarized by System Organ Class and Preferred Term for each treatment group. Adverse events are also summarized by their maximum severity. Summaries are also provided for the following types of AEs:

SAEs

Related AEs (including all categories for relationship to study medication other than "Unrelated", as determined by the Investigator)

AEs leading to early discontinuation of study medication

Remaining Safety Endpoints

The following safety endpoints are analyzed using time to event methods:

Individual components (death, myocardial infarction, stroke) of MACE

Thromboembolic events (defined as arterial thrombosis, DVT, PE, or vascular access thrombosis)

For these endpoints the incidence ("yes"/"no") of the endpoint are presented for each treatment arm. Kaplan-Meier curves are presented for each endpoint as the time of endpoint free survival (i.e., time until endpoint or death). The analysis of proportion of subjects with Hgb >12.0 g/dL, >13.0 g/dL, or >14.0 g/dL post baseline classify a subject as a "yes" if:

Any value Hgb >12.0 g/dL at any time after Day 1

Any confirmed value Hgb >12.0 g/dL at any time after Day 1

Any value Hgb >13.0 g/dL at any time after Day 1

Any confirmed value Hgb >13.0 g/dL at any time after Day 1

Any value Hgb >14.0 g/dL at any time after Day 1

Any confirmed value Hgb >14.0 g/dL at any time after Day 1

A Hgb value above a set threshold is considered as confirmed if there are 2 consecutive values above that threshold. The second of the 2 consecutive assessments should be done at most 12 weeks after the first assessment. Subjects with no available data post baseline are excluded from this analysis. All other subjects are classified to the "no" category.

The analysis of proportion of subjects with any Hgb increase >1.0 g/dL within any 2-week interval or >2.0 g/dL within any 4-week interval post baseline classify a subject as a "yes" if at least 1 of the following criteria at any point after Day 1 is met:

Hgb increase >1.0 g/dL within any 2-week interval

Hgb increase >2.0 g/dL within any 4-week interval

Subjects with no available data post baseline are excluded from this analysis. All other subjects are classified to the "no" category.

Observed values of continuous and categorical parameters and changes from baseline for continuous parameters to each study visit are summarized descriptively for vital signs and clinical laboratory results. Graphical displays of selected laboratory parameters are also provided.

Additional Assessments

Concomitant Medications:

Prior and concomitant medications are coded using World Health Organization (WHO) Drug dictionary. Prior medications are defined as any medications that were taken before the date of the first dose of study medication. Concomitant medications are defined as any medications taken at any time from the date of the first dose of study medication through the date of the last dose of the study medication. The total number of transfusions, ESA rescue therapies, and therapeutic phlebotomy collections are summarized by period as well as post baseline overall.

Biomarkers: Biomarkers (hepcidin and VEGF) are summarized descriptively at baseline and by visit post baseline.

Pharmacokinetics: Descriptive and graphical summaries are generated for PK measurements.

CKD-EPI Creatinine Equation

The estimated glomerular filtration rate (eGFR) is calculated from serum creatinine (isotope dilution mass spectrometry [IDMS] calibrated in mg/dL) using the Chronic Kidney Disease Epidemiology Collaboration (CKD EPI) creatinine equation (Levey et al. 2009).

The CKD-EPI creatinine equation is:

$$eGFR=141\times min(SCr/k,1)\alpha\times max(SCr/k,1)-1.209\times 0.993Age\times[1.018 \text{ if female}]\times[1.159 \text{ if black}],$$

where:

SCr is serum creatinine (in mg/dL)

k=0.7 for females k=0.9 for males $\alpha$=−0.329 for females $\alpha$=−0.411 for males min=the minimum of SCr/k or 1 max=the maximum of SCr/k or 1

ACTH (Cosyntropin) Stimulation Test for Adrenal Function Monitoring

The adrenocorticotropic hormone (ACTH) stimulation test assesses the function of the adrenal glands and their ability to respond to ACTH. Adrenocorticotropic hormone is a hormone produced in the pituitary gland that stimulates the adrenal glands to release cortisol. Cosyntropin is a synthetic form of ACTH. The ACTH stimulation test is recognized as the gold standard assay of adrenal insufficiency.

Sequential ACTH (cosyntropin) stimulation tests are conducted at European Union (EU) sites in the first 200 subjects randomized and who agree to participate in the testing (approximately 100 subjects per treatment arm). Testing is performed at the baseline (predose), Week 12, and Week 52 study visits, or at the end of treatment (EOT) visit if the subject permanently discontinues study medication early prior to the Week 52 study visit. Female subjects who have taken estrogens within 30 days of the first dose of study medication should be excluded from the adrenal function monitoring substudy.

Test details:

Obtain blood sample for pretest serum cortisol measurement (collected prior to administering cosyntropin)

Administer 0.25 mg cosyntropin via intravenous (IV) push

Obtain blood samples for serum cortisol measurements at 30 minutes and 60 minutes after dosing of cosyntropin.

6.4 Example 3: Pharmacokinetics of Selected Formulations

A study was carried out to assess the pharmacokinetic profile of two tablet formulations of Compound 1 as described herein. Formulation 1 was a tablet that comprised the following intra-granular components: 150 mg Compound 1, 158.4 mg microcrystalline cellulose, 9.53 mg isomalt, 10.70 mg sodium starch glycolate, 3.57 mg sodium lauryl sulfate, and 8.92 mg povidone. Formulation 1 further comprised the following extra-granular components: 14.28 mg sodium starch glycolate; 0.89 mg colloidal silicon dioxide, and 0.71 mg magnesium stearate. Formulation 2 was a tablet that comprised the following intra-granular components: 150 mg Compound 1, 57.46 mg microcrystalline cellulose, 6.90 mg sodium starch glycolate, and 6.44 mg hydroxypropyl methylcellulose. Formulation 2 further comprised the following extra-granular components: 6.9 mg sodium starch glycolate, 0.575 mg colloidal silicon dioxide, and 1.725 mg magnesium stearate, and a film coating component of about 2.0% to about 6.0% by weight of Opadry®. Formulation 2 is used in the examples described above, while Formulation 1 was used in previous clinical studies.

Primary objectives of this study were to assess the single-dose bioavailability of Formulation 2 relative to the reference Formulation 1 given under fasted conditions, and to assess the effect of a subject's diet (fed vs. fasted) on the single-dose bioavailability of a Formulation 2. Secondary objectives of the study were to characterize the pharmacokinetic parameters of Formulations 1 and 2 administered under fed (Formulation 2) and fasted (Formulations 1 and 2) conditions; and to monitor the safety and tolerability of a single dose of Compound 1.

The study was an open-label, single-dose, randomized, relative bioavailability study in healthy volunteers, utilizing a three-period, six-sequence crossover design. There was a washout period of at least 3 days between successive dose administrations. Subjects were randomly assigned to the following treatments:

Treatment A: Formulation 1 given in the fasted state.

Treatment B: Formulation 2 given in the fasted state.

Treatment C: Formulation 2 given in the fed state.

The subjects in the fed group were given the following high-fat meal prior to dose administration: 2 eggs fried in butter, 2 strips of pork bacon, 2 slices of toast with butter, 4 ounces of hash brown potatoes, and 8 ounces of whole milk. Dose administration occurred within 5 minutes of completing the high-fat meal.

Serial blood samples (6 mL each) were collected at 0 hours (pre-dose) and at 0.5, 1, 1.5, 2, 3, 4, 5, 6, 8, 12, 16 and 24 hours after each dose administration. Blood samples were centrifuged to separate plasma, and the plasma was stabilized with a solution of citric acid, and was stored frozen at or below −70° C. until shipped to a bioanalytical laboratory. Samples were analyzed for Compound 1 using a validated HPLC/MS-MS method at WIL Research Laboratories, Ashland, Ohio.

The following pharmacokinetic parameters for Compound 1 were estimated from the plasma concentrations using standard methods of non-compartmental analysis:

$C_{max}$—maximum observed plasma concentration $T_{max}$—time to maximum plasma concentration AUC$_{(0-t)}$—area under the concentration-time curve from time zero to the last quantifiable concentration, calculated using the linear trapezoidal rule AUC$_{(0-inf)}$—area under the concentration-time curve extrapolated to infinity T$_{1/2}$—Terminal exponential half-life Statistical analysis included the ratio of geometric means of test and reference products for C$_{max}$, AUC$_{(0-t)}$ and AUC$_{(0-inf)}$. The parameters were log-transformed prior to analysis.

A total of 18 subjects completed the study (12 males and 6 females). The doses were well tolerated and no significant adverse events were reported. FIG. 1A and FIG. 1B show the plasma concentration of Compound 1 delivered as Formulation 1 and 2 under fasted conditions. Both formulations showed similar profiles. Analogously, the key pharmacokinetic parameters exhibited no statistically significant difference between groups, as shown in Table 1 (Ratios and confidence intervals are expressed as percentages).

TABLE 1

| Compound 1 Parameter | Least Squares (LS) Geometric Means | | Geometric Mean Ratio (T/R) | 90% Confidence Interval for Ratio of LS Means |
|---|---|---|---|---|
| | Formulation 1, Fasted (R) | Formulation 2, Fasted (T) | | |
| AUC$_{(0-inf)}$ (h · µg/mL) | 99.1 | 110 | 111 | 103-119 |
| AUC$_{(0-t)}$ (h · µg/mL) | 95.8 | 106 | 111 | 103-119 |
| C$_{max}$ (µg/mL) | 19.0 | 20.6 | 108 | 97.4-120 |

FIG. 2A and FIG. 2B show the plasma concentration of Compound 1 delivered as Formulation 2 under fasted and under fed conditions. The concentration curves under the two conditions exhibited a high degree of similarity. Key pharmacokinetic parameters, however, exhibited statistically significant differences between groups, as shown in Table 2 (Ratios and confidence intervals are expressed as percentages). AUC was approximately 20% lower and and C$_{max}$ was 28% lower for Formulation 2 when administered immediately following a high-fat breakfast compared to fasted conditions. This indicates that the pharmacokinetics of Compound 1 administered as Formulation 2 are significantly affected by the subject's diet.

TABLE 2

| Compound 1 Parameter | Least Squares (LS) Geometric Means | | Geometric Mean Ratio (T/R) | 90% Confidence Interval for Ratio of LS Means |
|---|---|---|---|---|
| | Formulation 2, Fasted (R) | Formulation 2, Fed (T) | | |
| AUC$_{(0-inf)}$ (h · µg/mL) | 110 | 87.4 | 79.8 | 74.3-85.6 |
| AUC$_{(0-t)}$ (h · µg/mL) | 106 | 85.0 | 80.1 | 74.8-85.9 |
| C$_{max}$ (µg/mL) | 20.6 | 14.8 | 72.0 | 64.9-79.9 |

All of the dosing conditions were well tolerated and no significant adverse events were reported. Overall, Formulation 2 demonstrated general bioequivalence to Formulation 1. AUC and C$_{max}$ were significantly reduced when a single oral 150 mg dose of Formulation 2 tablets was administered with food compared to the test tablet formulation administered under fasting conditions.

The invention claimed is:

1. A tablet formulation comprising an intra-granular component, an extra-granular component, and a film coating component, wherein the intra-granular component comprises
about 60% to about 70% by weight of {[5-(3-chlorophenyl)-3-hydroxypyridine-2-carbonyl]amino}acetic acid,

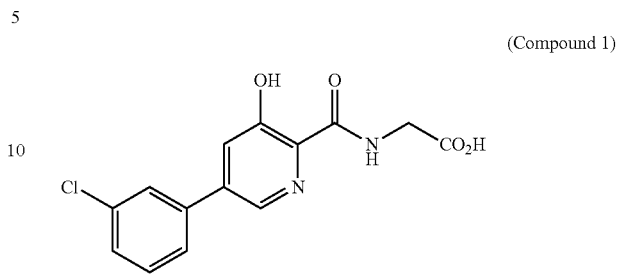

(Compound 1)

or a pharmaceutically acceptable salt thereof,
about 20% to about 30% by weight of microcrystalline cellulose,
about 2.5% to about 3.5% by weight of sodium starch glycolate, and
about 2.3% to about 3.3% by weight of a hydroxypropyl methylcellulose;
wherein the extra-granular component comprises
about 2.5% to about 3.5% by weight of a sodium starch glycolate,
about 0.2% to about 0.3% by weight of colloidal silicon dioxide, and
about 0.55% to about 0.95% by weight of magnesium stearate; and
wherein the film coating component comprises about 1.0% to about 8% by weight of a tablet coating.

2. The tablet formulation of claim 1,
wherein the intra-granular component comprises
about 65% by weight of Compound 1,
about 25% by weight of microcrystalline cellulose,
about 3% by weight of sodium starch glycolate, and
about 2.8% by weight of a hydroxypropyl methylcellulose.

3. The tablet formulation of claim 1, comprising about 150 mg Compound 1.

4. The tablet formulation of claim 1, comprising about 300 mg Compound 1.

5. The tablet formulation of claim 1, comprising about 450 mg Compound 1.

6. The tablet formulation of claim 1, comprising about 600 mg Compound 1.

7. The tablet formulation of claim 1, wherein the intra-granular component comprises:
   about 150 mg Compound 1,
   about 57.46 mg microcrystalline cellulose,
   about 6.90 mg sodium starch glycolate, and
   about 6.44 mg hydroxypropyl methylcellulose; and
   wherein the total weight of the intra-granular and extra-granular components is about 230 mg.

8. The tablet formulation of claim 7, wherein the extra-granular component comprises:
   about 6.9 mg sodium starch glycolate,
   about 0.575 mg colloidal silicon dioxide, and
   about 1.725 mg magnesium stearate.

* * * * *